(12) United States Patent
Anversa

(10) Patent No.: US 11,534,466 B2
(45) Date of Patent: Dec. 27, 2022

(54) PANCREATIC STEM CELLS AND USES THEREOF

(71) Applicant: AAL Scientifics, Inc., New York, NY (US)

(72) Inventor: Piero Anversa, New York, NY (US)

(73) Assignee: AAL SCIENTIFICS, INC., New York, NY (US)

( * ) Notice: Subject to any disclaimer, the term of this patent is extended or adjusted under 35 U.S.C. 154(b) by 0 days.

(21) Appl. No.: 15/452,338

(22) Filed: Mar. 7, 2017

(65) Prior Publication Data

US 2017/0258853 A1 Sep. 14, 2017

Related U.S. Application Data

(60) Provisional application No. 62/457,710, filed on Feb. 10, 2017, provisional application No. 62/305,736, filed on Mar. 9, 2016.

(51) Int. Cl.
*A61K 35/39* (2015.01)
*C12N 5/071* (2010.01)
*A61K 35/28* (2015.01)

(52) U.S. Cl.
CPC .............. *A61K 35/39* (2013.01); *A61K 35/28* (2013.01); *C12N 5/0676* (2013.01); *C12N 5/0678* (2013.01); *C12N 2501/105* (2013.01); *C12N 2501/115* (2013.01); *C12N 2501/12* (2013.01); *C12N 2501/125* (2013.01); *C12N 2501/14* (2013.01); *C12N 2533/52* (2013.01)

(58) Field of Classification Search
CPC ...... A61K 35/39; A61K 35/28; C12N 5/0678; C12N 2501/125; C12N 2501/105; C12N 2501/12; C12N 5/0676; C12N 2501/115; C12N 2501/14; C12N 2533/52; A61P 1/18; A61P 3/10; A61P 43/00
See application file for complete search history.

(56) References Cited

U.S. PATENT DOCUMENTS

| | | | |
|---|---|---|---|
| 5,843,780 A | 12/1998 | Thomson | |
| 5,945,577 A | 8/1999 | Stice et al. | |
| 5,994,619 A | 11/1999 | Stice et al. | |
| 6,200,806 B1 | 3/2001 | Thomson | |
| 6,235,970 B1 | 5/2001 | Stice et al. | |
| 7,547,674 B2 | 6/2009 | Anversa et al. | |
| 7,875,451 B2 | 1/2011 | Murry et al. | |
| 8,425,928 B2 | 4/2013 | Martinson et al. | |
| 9,132,226 B2 | 9/2015 | Martinson et al. | |
| 9,534,204 B2 | 1/2017 | Anversa et al. | |
| 9,808,489 B2 | 11/2017 | Anversa et al. | |
| 2001/0013134 A1 | 8/2001 | Sarvetnick et al. | |
| 2004/0158289 A1 | 8/2004 | Girouard et al. | |
| 2005/0053588 A1 | 3/2005 | Yin | |
| 2005/0187607 A1 | 8/2005 | Akhtar et al. | |
| 2005/0208029 A1* | 9/2005 | Umezawa | A61K 35/39 435/366 |
| 2006/0177453 A1 | 8/2006 | Mather et al. | |
| 2006/0239983 A1 | 10/2006 | Anversa et al. | |
| 2007/0031434 A1 | 2/2007 | Aguet | |
| 2007/0116691 A1 | 5/2007 | Gambler et al. | |
| 2007/0134254 A1 | 6/2007 | Kinch et al. | |
| 2007/0166288 A1 | 7/2007 | Murry et al. | |
| 2008/0019944 A1 | 1/2008 | Terzic et al. | |
| 2008/0241067 A1 | 10/2008 | Zimmerman et al. | |
| 2008/0267921 A1 | 10/2008 | Marban et al. | |
| 2008/0292677 A1 | 11/2008 | Cortiella et al. | |
| 2009/0018061 A1 | 1/2009 | Williams et al. | |
| 2009/0148421 A1 | 6/2009 | Anversa et al. | |
| 2009/0162329 A1 | 6/2009 | Anversa et al. | |
| 2009/0180998 A1 | 7/2009 | Anversa et al. | |
| 2010/0143345 A1 | 6/2010 | Kinch et al. | |
| 2010/0260749 A1 | 10/2010 | Kinch et al. | |
| 2011/0091428 A1 | 4/2011 | Anversa et al. | |
| 2011/0158691 A1* | 6/2011 | Foster | G03G 15/2053 399/329 |
| 2012/0020913 A1* | 1/2012 | Burkly | A61P 1/18 424/85.1 |
| 2012/0128638 A1 | 5/2012 | Gaussin et al. | |
| 2012/0288481 A1 | 11/2012 | Anversa et al. | |
| 2012/0321595 A1 | 12/2012 | Anversa et al. | |

(Continued)

FOREIGN PATENT DOCUMENTS

| EP | 1135153 B1 | 4/2005 |
|---|---|---|
| KR | 10-2009-0019078 A | 2/2009 |

(Continued)

OTHER PUBLICATIONS

Ma et al. Isolation of Pancreatic Progenitor Cells with the Surface Marker of Hematopoietic Stem Cells. International Journal of Endocrinology (2012), Article ID 948683, 8 pages (Year: 2012).*
Zhang et al. Proteomic Analysis for the Assessment of Different Lots of Fetal Bovine Serum as a Raw Material for Cell Culture. Part IV. Application of Proteomics to the Manufacture of Biological Drugs. Biotechnol. Prog. (2006), v22, p. 1294-1300. (Year: 2006).*
Quesada et al. Physiology of the pancreatic a-cell and glucagon secretion: role in glucose homeostasis and diabetes. Journal of Endocrinology (2008), v199, p. 5-19. (Year: 2008).*
Lusis et al. Isolation of clonogenic, long-term self renewing embryonic renal stem cells. Stem Cell Research (2010), v5, p. 23-39. (Year: 2010).*

(Continued)

*Primary Examiner* — Sean C. Barron
(74) *Attorney, Agent, or Firm* — Dunlap Bennett & Ludwig, PLLC; Anna L. Kinney

(57) ABSTRACT

The disclosure relates to stem cells and their therapeutic use in the treatment and/or prevention of pancreatic diseases or disorders. Provided herein are compositions comprising c-kit positive pancreatic stem cells and methods of preparing and using c-kit positive pancreatic stem cells for the treatment and/or prevention of pancreatic diseases or disorders.

11 Claims, 39 Drawing Sheets
(39 of 39 Drawing Sheet(s) Filed in Color)
Specification includes a Sequence Listing.

(56) References Cited

U.S. PATENT DOCUMENTS

| | | |
|---|---|---|
| 2013/0216508 A1 | 8/2013 | Anversa et al. |
| 2014/0093519 A1* | 4/2014 | Burkly .............. A61K 39/3955 424/172.1 |
| 2016/0220614 A1 | 8/2016 | Anversa et al. |
| 2017/0165301 A1 | 6/2017 | Anversa et al. |

FOREIGN PATENT DOCUMENTS

| | | |
|---|---|---|
| WO | 03/026584 A2 | 4/2003 |
| WO | WO 2005/026332 A1 | 3/2005 |
| WO | WO 2006/047638 A2 | 5/2006 |
| WO | WO 2006/052925 A2 | 5/2006 |
| WO | WO 2007/073499 A2 | 6/2007 |
| WO | WO 2007/124594 A1 | 11/2007 |
| WO | WO 2007/141309 A2 | 12/2007 |
| WO | WO 2007/149447 A2 | 12/2007 |
| WO | WO 2008/010101 A2 | 1/2008 |
| WO | WO 2009/008901 A2 | 1/2009 |
| WO | WO 2009/062143 A2 | 5/2009 |
| WO | WO 2009/073518 A1 | 6/2009 |
| WO | WO 2011/057249 A2 | 5/2011 |
| WO | WO 2011/057251 A2 | 5/2011 |
| WO | WO 2012/047951 A2 | 4/2012 |
| WO | WO 2017/156076 A1 | 9/2017 |

OTHER PUBLICATIONS

Ishkitiev et al. Pancreatic differentiation of human dental pulp CD117+ stem cells. Regen. Med. (2013) v8(5), p. 597-612. (Year: 2013).*
Kruse et al. Pluripotency of adult stem cells derived from human and rat pancreas. Appl. Phys. A. (2004), v79, p. 1617-1624. (Year: 2004).*
Meier et al. Differentiation potential of human pancreatic stem cells for epithelial-and endothelial-like cell types. Ann. Anat. (2009), v191, p. 70-82. (Year: 2009).*
Kunisada et al. Small molecules induce efficient differentiation into insulin-producing cells from human induced pluripotent stem cells. Stem Cell Research (2012), 8(2), 274-284. (Year: 2012).*
Gong et al. Migration path of stem cells involved in the repair of damaged pancreatic tissue caused by pancreatitis. Int J Clin Exp Pathol 2014;7(5):2438-2445. (Year: 2014).*
Suzuki et al. Prospective Isolation of Multipotent Pancreatic Progenitors Using Flow-Cytometric Cell Sorting. Diabetes (2004), 53, 2413-2152. (Year: 2004).*
Wang et al. Sphere-Forming Assays for Assessment of Benign and Malignant Pancreatic Stem Cells. Ch. 15 in Methods in Molecular Biology (2013), 980, 281-290. (Year: 2013).*
Davani et al. Human Islet-Derived Precursor Cells Are Mesenchymal Stromal Cells That Differentiate and Mature to Hormone-Expressing Cells In Vivo. Stem Cells (2007), 25, 3215-3222. (Year: 2007).*
International Search Report and Written Opinion in International Application No. PCT/US2017/021290 dated Jun. 7, 2017, 15 pages.
Ma, Fengxia, et al. "Isolation of Pancreatic Progenitor Cells with the Surface Marker of Hematopoietic Stem Cells." International Journal of Endocrinology (2012); vol. 2012, Article ID 948683, 8 pages.
Wu, Yuexiu, et al. "c-Kit and stem cell factor regulate PANC-1 cell differentiation into insulin- and glucagon-producing cells." Laboratory Investigation (2010); 90.9: 1373-1384.
"Late-Breaking Basic Science Abstracts From the American Heart Association's Scientific Sessions 2009, Orlando, Florida, Nov. 14-18, 2009", Circulation Research (2009); 105(12): e55-e62.
Anversa and Olivetti. "Cellular basis of physiological and pathological myocardial growth." In: Handbook of Physiology, Section 2, The Heart. (2011); (eds. Page, et al., New York Oxford University Press, pp. 75-144.
Arda, H. Efsun, et al. "Gene regulatory networks governing pancreas development." Developmental Cell (2013); 25.1: 5-13.

Bader, Erik, et al. "Identification of proliferative and mature β-cells in the islets of Langerhans." Nature (2016); 535.7612: 430-434.
Baker et al., "Role of Insulin-like Growth Factors in Embryonic and Postnatal Growth." Cell (1993); 75:73-82.
Bearzi et al., "Human cardiac stem cells." PNAS (2007); 104(35):14068-14073.
Beltrami et al., "Adult Cardiac Stem Cells are Multipotent and Support Myocardial Regeneration." Cell (2003); 114:763-776.
Bender-Kim et al. "Identification of bronchioalveolar stem cells in normal lung and lung cancer." Cell (2005); 121(6): 823-835.
Blaauw et al., "Stretch-induced hypertrophy of isolated adult rabbit cardiomyocytes." Am J Physiol Heart Circ Physiol (2010); 299:H780-H787.
Bonner-Weir, Susan, and Aguayo-Mazzicato, Christina. "Physiology: Pancreatic β-cell heterogeneity revisited." Nature (2016); 535.7612: 365-366.
Boudina, Sihem, et al. "Diabetic cardiomyopathy revisited." Circulation (2007); 115.25: 3213-3223.
Brown and Schneyer. "Emerging roles for the TGFβ family in pancreatic β-cell homeostasis." Trends Endocrinol Metab. (2010); 21(7): 441-448.
Buja and Vela, "Cardiomyocyte death and renewal in the normal and diseased heart." Cardiovascular Pathology (2008); 17.6: 349-374.
Cairns, Linda A., et al. "Kit regulatory elements required for expression in developing hematopoietic and germ cell lineages." Blood (2003); 102.12: 3954-3962.
Chimenti et al., "Senescence and Death of Primitive Cells and Myocytes Lead to Premature Cardiac Aging and Heart Failure." Circ Res. (2003); 93:604-613.
Christie et al., "The registry of the international society for heart and lung transplantation: twenty-sixth official adult lung and heart-lung transplantation report—2009." J Heart Lung Transplant (2009); 28:1031-1049.
Cortiella, et al. "Tissue-Engineered Lung: An In Vivo and In Vitro Comparison of Polyglycolic Acid and Pluronic F-127 Hydrogel/Somatic Lung Progenitor Cell Constructs to Support Tissue Growth." Tissue Engineering (2006); 12: 1213-1225.
De Gasperi, Rita, et al. "The IRG mouse: A two-color fluorescent reporter for assessing Cre-mediated recombination and imaging complex cellular relationships in situ." Genesis (2008); 46.6: 308-317.
Dirice, Ercument, et al. "Soluble factors secreted by T cells promote β-cell proliferation." Diabetes (2014); 63.1: 188-202.
Dor, Yuval, and Glaser, Benjamin, "β-cell dedifferentiation and type 2 diabetes." New England Journal of Medicine (2013); 368.6: 572-573.
Dor, Yuval, et al. "Adult pancreatic β-cells are formed by self-duplication rather than stem-cell differentiation." Nature (2004); 429.6987: 41-46.
Dorrell, Craig, et al. "Human islets contain four distinct subtypes of [beta] cells." Nature communications (2016); 7: 11756.
Ellison, Georgina M., et al. "Adult c-kit pos cardiac stem cells are necessary and sufficient for functional cardiac regeneration and repair." Cell (2013); 154.4: 827-842.
Erbay et al., "IGF-II transcription in skeletal myogenesis is controlled by mTOR and nutrients." The Journal of Cell Biology (2003); 163(5):931-936.
Esposito, Irene, et al. "The stem cell factor-c-kit system and mast cells in human pancreatic cancer." Laboratory Investigation (2002); 82.11: 1481-1492.
Extended European Search Report in European Patent Application No. 10829273.1 dated Oct. 2, 2013, 9 pages.
Extended European Search Report in European Patent Application No. 10829275.6 dated Nov. 26, 2013, 7 pages.
Extended European Search Report in European Patent Application No. 11831492.1 dated Mar. 7, 2014, 6 pages.
Feng, Zhi-Chao, et al. "A survival kit for pancreatic beta cells: stem cell factor and c-Kit receptor tyrosine kinase." Diabetologia (2015); 58.4: 654-665.
Ferreira-Martins, Joãao, et al. "Cardiomyogenesis in the Developing Heart Is Regulated by C-Kit—Positive Cardiac Stem Cells." Circulation Research (2012); 110.5: 701-715.

(56) References Cited

OTHER PUBLICATIONS

Geiss, Gary K., et al. "Direct multiplexed measurement of gene expression with color-coded probe pairs." Nature Biotechnology (2008); 26.3: 317-325.

Geissler, Edwin N., et al. "The dominant-white spotting (W) locus of the mouse encodes the c-kit proto-oncogene." Cell (1988); 55.1: 185-192.

Gomez, Danielle L., et al. "Neurogenin 3 expressing cells in the human exocrine pancreas have the capacity for endocrine cell fate." PLOS One (2015); 10.8: e0133862.

Gong, JiaQing, et al. "Islet-derived stem cells from adult rats participate in the repair of islet damage." Journal of Molecular Histology (2012); 43.6: 745-750.

Gonzalez et al., "Activation of Cardiac Progenitor Cells Reverses the Failing Heart Senescent Phenotype and Prolongs Lifespan." Circ Res. (2008); 102:597-606.

Goodell, Margaret A., et al. "Somatic stem cell heterogeneity: diversity in the blood, skin and intestinal stem cell compartments." Nature Reviews Molecular Cell Biology (2015); 16.5: 299-309.

Goss, Garrett M., et al. "Differentiation potential of individual olfactory c-Kit+ progenitors determined via multicolor lineage tracing." Developmental Neurobiology (2016); 76.3: 241-251.

Gradwohl, Gáćú érard, et al. "Neurogenin3 is required for the development of the four endocrine cell lineages of the pancreas." Proceedings of the National Academy of Sciences (2000); 97.4: 1607-1611.

Gu, Guoqiang, et al. "Direct evidence for the pancreatic lineage: NGN3+ cells are islet progenitors and are distinct from duct progenitors." Development (2002); 129.10: 2447-2457.

Hadi, Hadi A.R., and Suwaidi, Jassim Ai. "Endothelial dysfunction in diabetes mellitus." Vascular Health and Risk Management (2007); 3.6: 853-876.

Hare et al., "A Randomized, Double-Blind, Placebo-Controlled, Dose-Escalation Study of Intravenous Adult Human Mesenchymal Stem Cells (Prochymal) After Acute Myocardial Infarction." Journal of the American College of Cardiology (2009); 54(24): 2277-2286.

Hatzistergos, Konstantinos E., et al. "cKit+cardiac progenitors of neural crest origin." Proceedings of the National Academy of Sciences (2015); 112.42: 13051-13056.

Heger, Klaus, et al. "CreERT2 expression from within the c-Kit gene locus allows efficient inducible gene targeting in and ablation of mast cells." European Journal of Immunology (2014); 44.1: 296-306.

Himanen, Juha P., et al. "Ligand recognition by A-class Eph receptors: crystal structures of the EphA2 ligand-binding domain and the EphA2/ephrin-A1 complex." EMBO Reports (2009); 10.7: 722-728.

Hosoda, Toru, et al. "Clonality of mouse and human cardiomyogenesis in vivo." Proceedings of the National Academy of Sciences (2009); 106.40: 17169-17174.

Hsu, Ya-Chieh, and Fuchs, Elaine. "A family business: stem cell progeny join the niche to regulate homeostasis." Nature Reviews Molecular Cell Biology (2012); 13.2: 103-114.

HU et al., "An analysis of the effects of stretch on IGF-1 secretion from rat ventricular fibroblasts." Am J Physiol Heart Circ Physiol (2007); 293:H677-H683.

Hua, Jinlian, et al. "Characterization of mesenchymal stem cells (MSCs) from human fetal lung: potential differentiation of germ cells." Tissue and Cell (2009); 41.6: 448-455.

Hua, Xiu-feng, et al. "Pancreatic insulin-producing cells differentiated from human embryonic stem cells correct hyperglycemia in SCID/NOD mice, an animal model of diabetes." PLOS One (2014); 9.7: e102198.

International Search Report and Written Opinion in International Application No. PCT/US2010/055993 dated Aug. 2, 2011, 10 pages.

International Preliminary Reporton Patentability in International Patent Application No. PCT/US2010/055993 dated May 15, 2012, 6 pages.

International Search Report and Written Opinion in International Application No. PCT/US2010/055999 dated Aug. 2, 2011, 10 pages.

International Preliminary Reporton Patentability in International Application No. PCT/US2010/055999 dated May 15, 2012, 6 pages.

International Search Report and Written Opinion in International Application No. PCT/US2011/054849 dated Apr. 26, 2012, 11 pages.

International Preliminary Report on Patentability in International Application No. PCT/US2011/054849 dated Apr. 9, 2013, 7 pages.

Itzhaki-Alfia et al., "Patient Characteristics and Cell Source Determine the Number of Isolated Human Cardiac Progenitor Cells." Circulation (2009); 120:2559-2566.

Jennings, Rachel E., et al. "Human pancreas development." Development (2015); 142.18: 3126-3137.

Jiang and Morahan. "Pancreatic stem cells: from possible to probable." Stem Cell Reviews and Reports (2012); 8.3: 647-657.

Kajstura et al., "Evidence for human lung stem cells." N Engl J Med, 364(19): 1795-1806 (2011).

Kajstura et al., "IGF-1 Overexpression Inhibits the Development of Diabetic Cardiomyopathy and Angiotensin 11-Mediated Oxidative Stress." Diabetes (2001), 50:1414-1424.

Kawamoto et al., "CD34-Positive Cells Exhibit Increased Potency and Safety for Therapeutic Neovascularization After Myocardial Infarction Compared With Total Mononuclear Cells." Circulation (2006); 114:2163-2169.

Keenan, Hillary A., et al. "Residual insulin production and pancreatic β-cell turnover after 50 years of diabetes: Joslin Medalist Study." Diabetes (2010); 59.11: 2846-2853.

Kikawa et al., "Regulation of the EphA2 kinase by the low molecular weight tyrosine phospatase induces transformation." J. Biol. Chem. (2002); 277(42): 39274-39279.

Klein, Sabine, et al. "Interstitial cells of Cajal integrate excitatory and inhibitory neurotransmission with intestinal slow-wave activity." Nature Communications (2013); 4: 1630.

Kollet et al., "HGF, SDF-1, and MMP-9 are involved in stress-induced human CD34+stem cell recruitment to the liver." The Journal of Clinical Investigation (2003); 112(2):160-169.

Kotton et al. "Lung stem cells." Cell Tissue Res (2008); 331(1):145-156.

Kotton et al., "Lung stem cells: new paradigms." Experimental Hematology (2004); 32(4): 340-343.

Kretzschmar and Watt. "Lineage tracing." Cell (2012); 148.1: 33-45.

Krishnamurthy, Mansa, et al. "c-Kit in Early Onset of Diabetes: A Morphological and Functional Analysis of Pancreatic β-Cells in c-Kit Wv Mutant Mice." Endocrinology (2007); 148.11: 5520-5530.

Kroon, Evert, et al. "Pancreatic endoderm derived from human embryonic stem cells generates glucose-responsive insulin-secreting cells in vivo." Nature Biotechnology (2008); 26.4: 443-452.

Le Roith, "Regulation of proliferation and apoptosis by the insulin-like growth factor I receptor." Growth Hormone & IGF Research (2000); Supplement A:S12-S13.

Lemper, Marie, et al. "Reprogramming of human pancreatic exocrine cells to β-like cells." Cell Death & Differentiation (2015); 22.7: 1117-1130.

Leri et al., "Cardiac Stem Cells and Mechanisms of Myocardial Regeneration." Physiol Rev (2005); 85:1373-1416.

Leri, Annarosa, and Anversa, Piero. "Complexity of Tracking the Fate of Adult Progenitor Cells." Circulation Research (2016); 119.10: 1067-1070.

Leri, Annarosa, et al. "Origin of cardiomyocytes in the adult heart." Circulation Research (2015); 116.1: 150-166.

Linke et al., "Stem cells in the dog heart are self-renewing, clonogenic, and multipotent and regenerate infarcted myocardium, improving cardiac function." PNAS (2005); 102(25):8966-8971.

Liu, Qiaozhen, et al. "c-kit+cells adopt vascular endothelial but not epithelial cell fates during lung maintenance and repair." Nature Medicine (2015); 21.8: 866-868.

Liu, Xiaoli, et al. "Rescue of neonatal cardiac dysfunction in mice by administration of cardiac progenitor cells in utero." Nature Communications (2015); 6: 8825.

(56) References Cited

OTHER PUBLICATIONS

Losordo et al., "Intramyocardial Transplantation of Autologous CD34+ Stem Cells for Intractable Angina: A Phase Iiiia Double-Blind, Randomized Controlled Trial." Circulation (2007); 115:3165-3172.
Lu, Jingwei, et al. "A novel technology for hematopoietic stem cell expansion using combination of nanofiber and growth factors." Recent Patents on Nanotechnology (2010); 4.2: 125-134.
Maeng et al., "Endothelial progenitor cell homing: prominent role of the IGF2-IGF2R-PLC beta2 axis." Blood (2009); 113:233-243.
Manoranjan, Branavan, et al. "Foxg1 interacts with bmi1 to regulate self-renewal and tumorigenicity of medulloblastoma stem cells." Stem Cells (2013); 31.7: 1266-1277.
McBride, Jennifer L., and Ruiz, Joseph C. "Ephrin-A1 is expressed at sites of vascular development in the mouse." Mechanisms of Development (1998); 77.2: 201-204.
McDevitt et al., "Proliferation of cardiomyocytes derived from human embryonic stem cells is mediated via the IGF/PI 3-kinase/Akt signaling pathway." Journal of Molecular and Cellular Cardiology (2005); 39:865-873.
Menge, Bjoern A., et al. "Long-term recovery of β-cell function after partial pancreatectomy in humans." Metabolism (2012); 61.5: 620-624.
Mezza, Teresa, and Kulkarni, Rohit N. "The regulation of pre-and post-maturational plasticity of mammalian islet cell mass." Diabetologia (2014); 57.7: 1291-1303.
Miao et al., "Activation of EphA2 kinase suppresses integrin function and causes focal-adhesion-kinase dephosphorylation", Nature Cell Biology (2000); 2: 62-69.
Murasawa et al., "Niche-Dependent Translineage Commitment of Endothelial Progenitor Cells, Not Cell Fusion in General, Into Myocardial Lineage Cells." Arterioscler Thromb Vase Biol. (2005); 25:1388-1394.
Murtaugh and Melton. "Genes, signals, and lineages in pancreas development." Annual Review of Cell and Developmental Biology (2003); 19.1: 71-89.
Muzumdar, Mandar Deepak, et al. "A global double-fluorescent Cre reporter mouse." Genesis (2007); 45.9: 593-605.
Nadal-Ginard, Bernardo, et al. "Absence of Evidence Is Not Evidence of Absence Pitfalls of Cre Knock-Ins in the c-Kit Locus." Circulation Research (2014); 115.4: 415-418.
Ogita, Hisakazu, et al. "EphA4-mediated Rho activation via Vsm-RhoGEF expressed specifically in vascular smooth muscle cells." Circulation Research (2003); 93.1: 23-31.
Oram, Richard A., et al. "The majority of patients with long-duration type 1 diabetes are insulin microsecretors and have functioning beta cells." Diabetologia (2014); 57.1: 187-191.
Orioli et al., "The Eph receptor family: axonal guidance by contact repulsion", TIG (1997); 13(9): 354-359.
Orlic et al., "Bone marrow cells regenerate infarcted myocardium." Nature (2001); 410:701-705.
Orlic, D., et al. "Purification and characterization of heterogeneous pluripotent hematopoietic stem cell populations expressing high levels of c-kit receptor." Blood (1993); 82.3: 762-770.
Padin-Iruegas et al., "Cardiac Progenitor Cells and Biotinylated Insulin-Like Growth Factor-1 Nanofibers Improve Endogenous and Exogenous Myocardial Regeneration After Infarction." Circulation (2009); 120:876-887.
Pandey et al., "Activation of the Eck Receptor Protein Tyrosine Kinase Stimulates Phosphatidylinositol 3-Kinase Activity", The Journal of Biological Chemistry (1994); 269(48): 30154-30157.
Parri, Matteo, et al. "EphrinAI activates a Src/focal adhesion kinase-mediated motility response leading to rho-dependent actino/myosin contractility." Journal of Biological Chemistry (2007); 282.27: 19619-19628.
Pasquale, E.B. "The Eph family of receptors", Current Opinion in Cell Biology (1997); 9: 608-615.
Perl, S., et al. "Significant human β-cell turnover is limited to the first three decades of life as determined by in vivo thymidine analog incorporation and radiocarbon dating." The Journal of Clinical Endocrinology & Metabolism 95.10 (2010): E234-E239.
Peters, Katharina, et al. "Expression of stem cell markers and transcription factors during the remodeling of the rat pancreas after duct ligation." Virchows Archiv (2005); 446.1: 56-63.
Petley et al., "Variation Among Cell Types in the Signaling Pathways by which IGF-1 Stimulates Specific Cellular Responses." Horm Metab Res (1999), 31:70-76.
Philippou et al., "Type I insulin-like growth factor receptor signaling in skeletal muscle regeneration and hypertrophy." J Musculoskelet Neuronal Interact (2007); 7(3):208-218.
Pratt et al., "Activation of the EphA2 tyrosine kinase stimulates the MAP/ERK kinase signaling cascade", Oncogene (2002); 21: 7690-7699, 2002.
Quesenberry, Peter J., et al. "Perspective: fundamental and clinical concepts on stem cell homing and engraftment: a journey to niches and beyond." Experimental Hematology (2005); 33.1: 9-19.
Qu, Xiaoling, et al. "Notch-mediated post-translational control of Ngn3 protein stability regulates pancreatic patterning and cell fate commitment." Developmental Biology (2013); 376.1: 1-12.
Rosen et al., "Specific, Temporally Regulated Expression of the Insulin-Like Growth Factor II Gene During Muscle Cell Differentiation." Endocrinology (1993); 133(2):474-481.
Rosenthal et al., "Regulation of Insulin-like Growth Factor (IGF) I Receptor Expression During Muscle Cell Differentiation." J. Clin. Invest. (1991), 87:1212-1219.
Rosu-Myles et al., "A unique population of bone marrow cells migrates to skeletal muscle via hepatocyte growth factor/c-met axis." Journal of Cell Science (2005), 118:4343-4352.
Rota et al., "Local Activation or Implantation of Cardiac Progenitor Cells Rescues Scarred Infarcted Myocardium Improving Cardiac Function." Circ Res. (2008); 103:107-116.
Rota, Marcello, et al. "Bone marrow cells adopt the cardiomyogenic fate in vivo." Proceedings of the National Academy of Sciences (2007); 104.45: 17783-17788.
Saisho, Yoshifumi. "Importance of beta cell function for the treatment of type 2 diabetes." Journal of Clinical Medicine (2014); 3.3: 923-943.
Sanada, Fumihiro, et al. "c-Kit—Positive Cardiac Stem Cells Nested in Hypoxic Niches Are Activated by Stem Cell Factor Reversing the Aging Myopathy." Circulation Research (2014); 114.1: 41-55.
Sandstedt et al., "C-kit+ CD45—cells found in the adult human heart represent a population of endothelial progenitor cells." Basic Res Cardiol (2010); 105(4):545-556.
Schächinger et al., "Intracoronary Bone Marrow-Derived Progenitor Cells in Acute Myocardial Infarction." The New England Journal of Medicine (2006); 355:1210-1221.
Seymour, Philip A. "Sox9: a master regulator of the pancreatic program." The Review of Diabetic Studies: RDS (2014); 11.1: 51-83.
Sherr, Jennifer L., et al. "Characterization of residual β cell function in long-standing type 1 diabetes." Diabetes/Metabolism Research and Reviews (2014); 30.2: 154-162.
Shih, Hung Ping, et al. "A Notch-dependent molecular circuitry initiates pancreatic endocrine and ductal cell differentiation." Development (2012); 139.14: 2488-2499.
Smith et al., "Regenerative Potential of Cardiosphere-Derived Cells Expanded From Percutaneous Endomyocardial Biopsy Specimens." Circulation (2007); 115:896-908.
Smukler, Simon R., et al. "The adult mouse and human pancreas contain rare multipotent stem cells that express insulin." Cell Stem Cell (2011); 8.3: 281-293.
Soyer, Josselin, et al. "Rfx6 is an Ngn3-dependent winged helix transcription factor required for pancreatic islet cell development." Development (2010); 137.2: 203-212.
Stephen, Lesley J., et al. "A critical role for the EphA3 receptor tyrosine kinase in heart development." Developmental Biology (2007); 302.1: 66-79.
Talhouk, Aline, et al. "Single-patient molecular testing with NanoString nCounter data using a reference-based strategy for batch effect correction." PLOS One (2016); 11.4: e0153844.
Ten Dijke, Peter, and Iwata, Kenneth K. "Growth factors for wound healing." Nature Biotechnology (1989); 7.8: 793-798.

(56) References Cited

OTHER PUBLICATIONS

Tiemann, Katharina, et al. "Expression of transcription factors and precursor cell markers during regeneration of β cells in pancreata of rats treated with streptozotocin." Virchows Archiv (2007); 450.3: 261-266.

Torella et al., "Cardiac Stem Cell and Myocyte Aging, Heart Failure, and Insulin-Like Growth Factor-1 Overexpression." Circulation Research (2004); 94:514-524.

Urbanek et al., "Cardiac Stem Cells Possess Growth Factor-Receptor Systems That After Activation Regenerate the Infarcted Myocardium, Improving Ventricular Function and Long-Term Survival." Circ Res. (2005); 97:663-673.

Urbanek et al., "Intense myocyte formation from cardiac stem cells in human cardiac hypertrophy." PNAS (2003); 100(18):10440-10445.

Urbanek et al., "Myocardial regeneration by activation of multipotent cardiac stem cells in ischemic heart failure." PNAS (2005), 102(24):8692-8697.

Urbanek et al., "Stem cell niches in the adult mouse heart." PNAS (2006); 103(24):9226-9231.

Van Berlo, Jop H., et al. "C-kit+ cells minimally contribute cardiomyocytes to the heart." Nature (2014); 509.7500: 337-341.

Veldman-Jones, Margaret H., et al. "Evaluating robustness and sensitivity of the NanoString technologies nCounter platform to enable multiplexed gene expression analysis of clinical samples." Cancer Research (2015); 75.13: 2587-2593.

Wajchenberg, Bernardo L. "Beta-cell failure in diabetes and preservation by clinical treatment." Endocrine Reviews (2007); 28.2: 187-218.

Weinberg, Noa, et al. "Lineage tracing evidence for in vitro dedifferentiation but rare proliferation of mouse pancreatic β-cells." Diabetes (2007); 56.5: 1299-1304.

Williams, Scott E., et al. "Asymmetric cell divisions promote Notch-dependent epidermal differentiation." Nature (2011); 470. 7334: 353-358.

Wilson et al., "Mechanisms of Signal Transduction: Control of MyoD Function during Initiation of Muscle Differentiation by an Autocrine Signaling Pathway Activated by Insulin-like Growth Factor-II." J. Biol. Chem. (2006); 281(40): 29962-29971.

Xiao, Xiangwei, et al. "No evidence for β cell neogenesis in murine adult pancreas." The Journal of Clinical Investigation (2013); 123.5: 2207-2217.

Xu, Xiaobo, et al. "β cells can be generated from endogenous progenitors in injured adult mouse pancreas." Cell (2008); 132.2: 197-207.

Yagihashi, Soroku, et al. "Dynamic pathology of islet endocrine cells in type 2 diabetes: β-Cell growth, death, regeneration and their clinical implications." Journal of Diabetes Investigation (2016); 7.2: 155-165.

Ye and D'Ercole, "Insulin-Like Growth Factor Actions During Development of Neural Stem Cells and Progenitors in the Central Nervous System." Journal of Neuroscience Research (2006); 83:1-6.

Zhu et al., "IGFBP-4 is an inhibitor of canonical Wnt signalling required for cardiogenesis." Nature (2008); 454:345-349.

Turner Anne M., et al., "Nonhematopoietic Tumor Cell Lines Express Stem Cell Factor and Display c-kit Receptors." Blood (1992); 80: 374-381.

Suen P M et al.; "PDZ-domain containing-2 (PDZD2) is a novel factor that affects the growth and differentiation of human fetal pancreatic progenitor cells", International Journal of Biochemistry and Cell Biology, Pergamon, GB, vol. 40, No. 4, Jan. 1, 2008 (Jan. 1, 2008), pp. 789-803, XP026865735, ISSN: 1357-2725.

Pia Montanucci et al.; "The functional performance of microencapsulated human pancreatic islet-derived precursor cells", Biomaterials, Elsevier Science Publishers BV., Barking, GB, vol. 32, No. 35, Aug. 16, 2011 (Aug. 16, 2011), pp. 9254-9262, XP028308447, ISSN: 0142-9612, DOI: 10.1016/J.BIOMATERIALS.2011.08.052.

Rumman et al., "Concise Review: Quiescence in Adult Stem Cells: Biological Significance and Relevance to Tissue Regeneration," Stem Cells (2015), vol. 33, 2903-2912.

\* cited by examiner control | Dexa

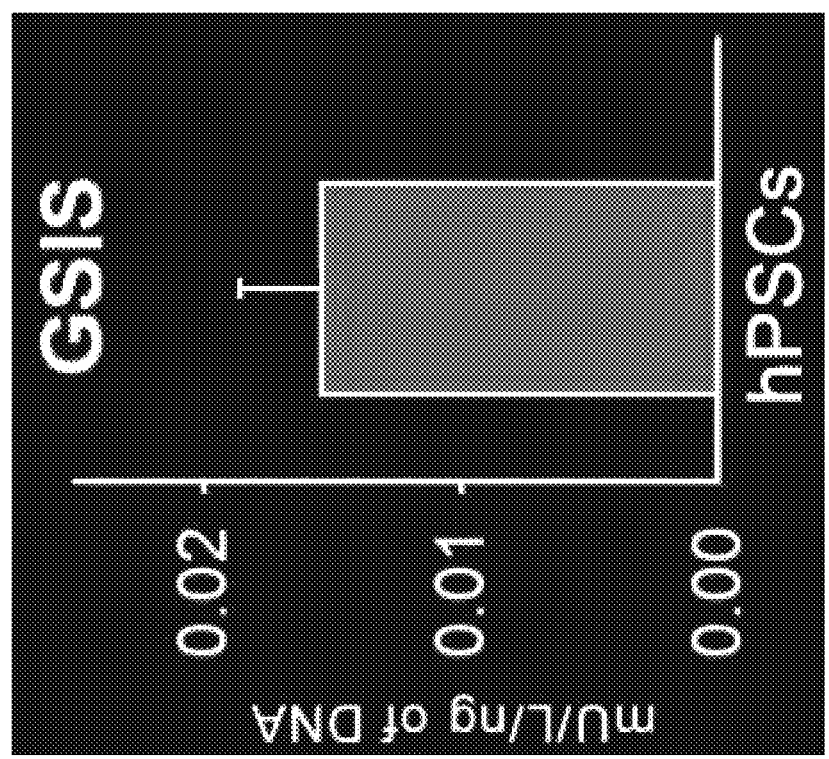

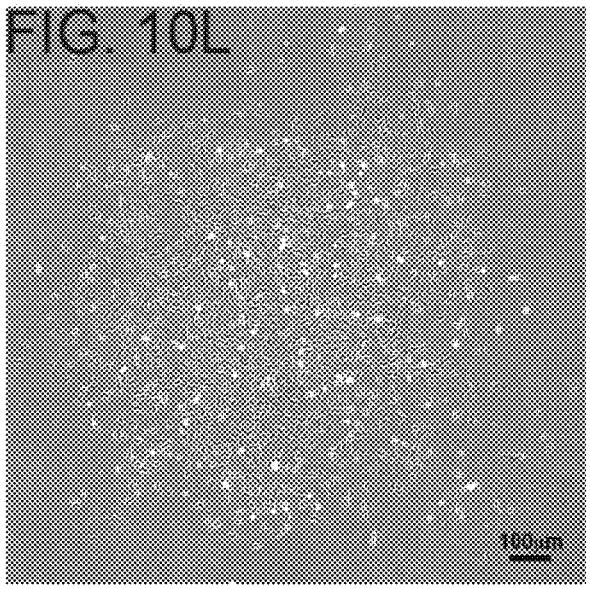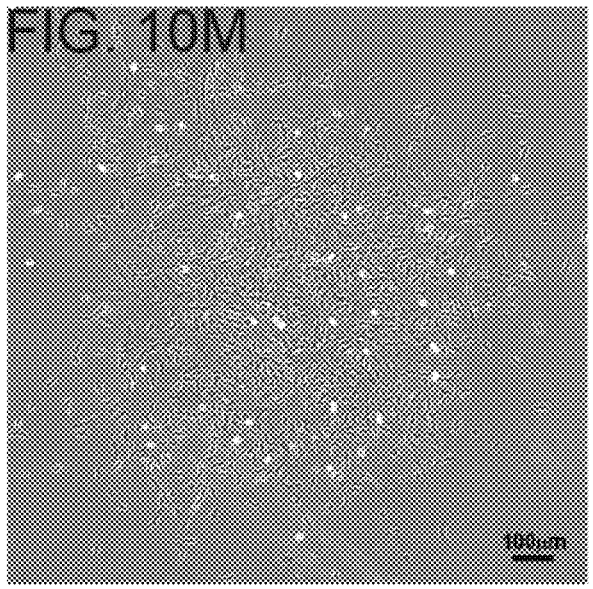
FIG. 10L - FIG. 10P

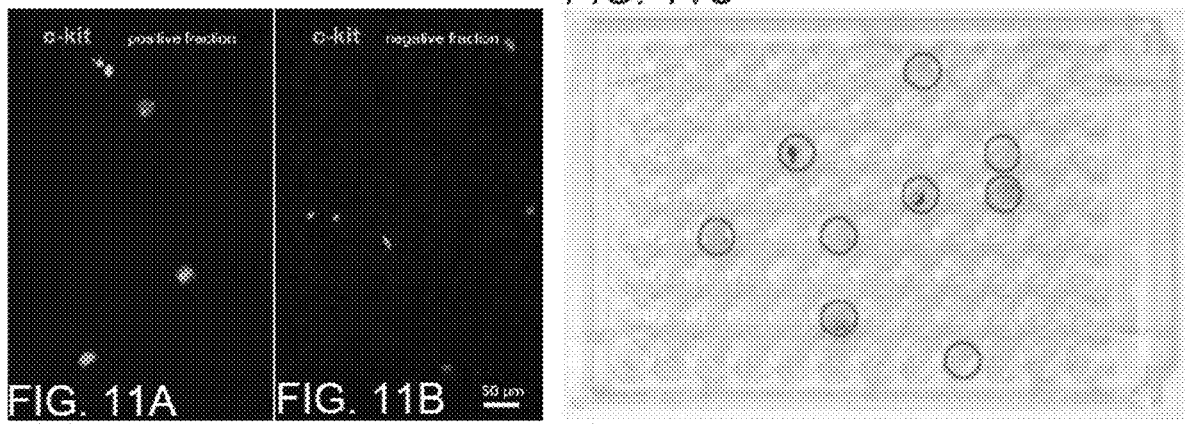
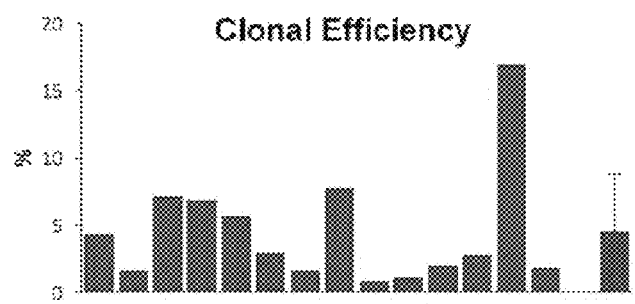
FIG. 11A - FIG. 11I

FIG. 12A
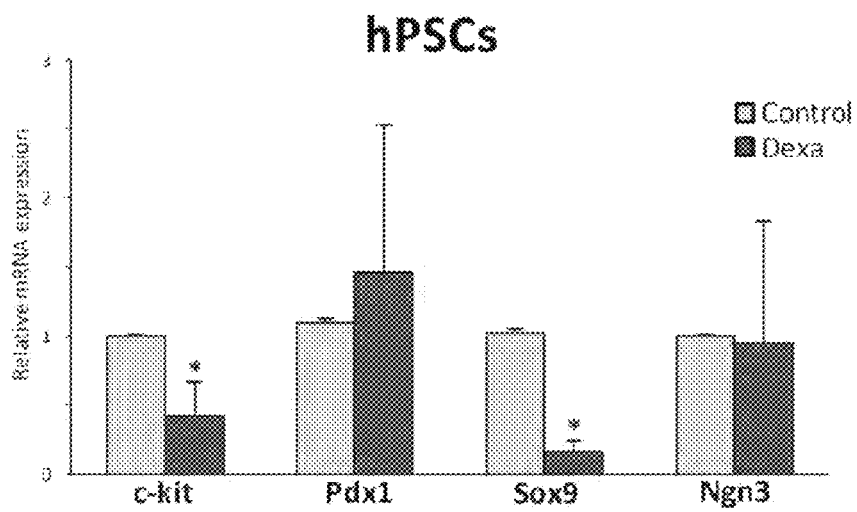
FIG. 12B
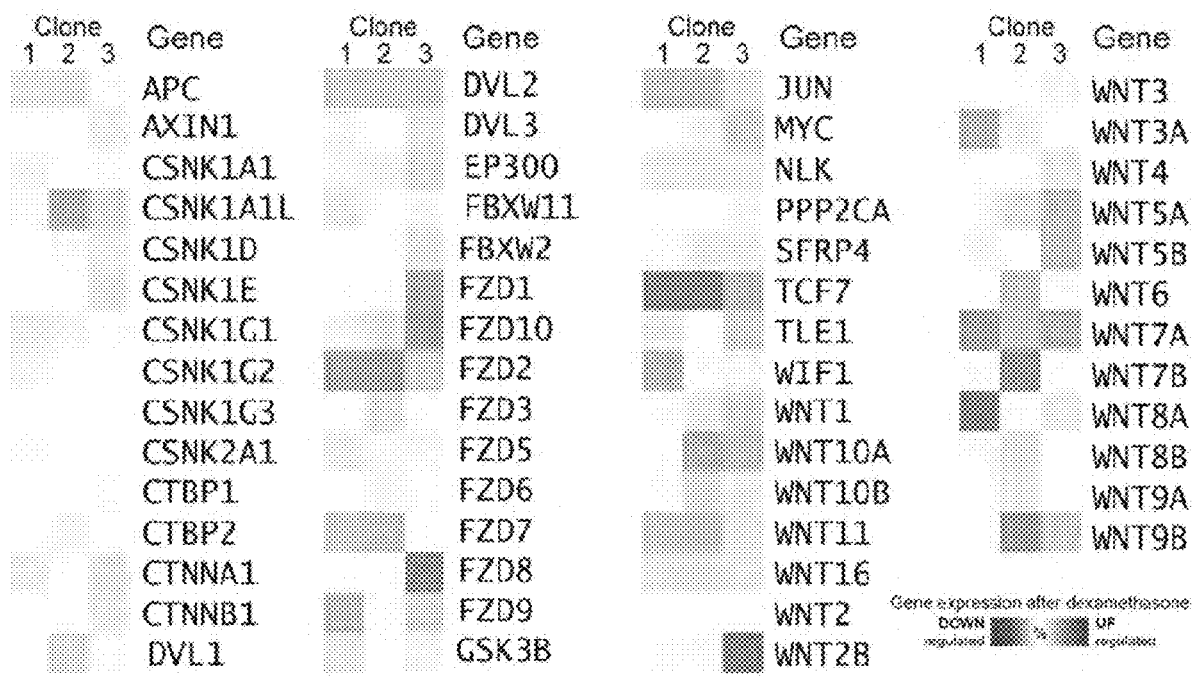
FIG. 12A - FIG. 12B

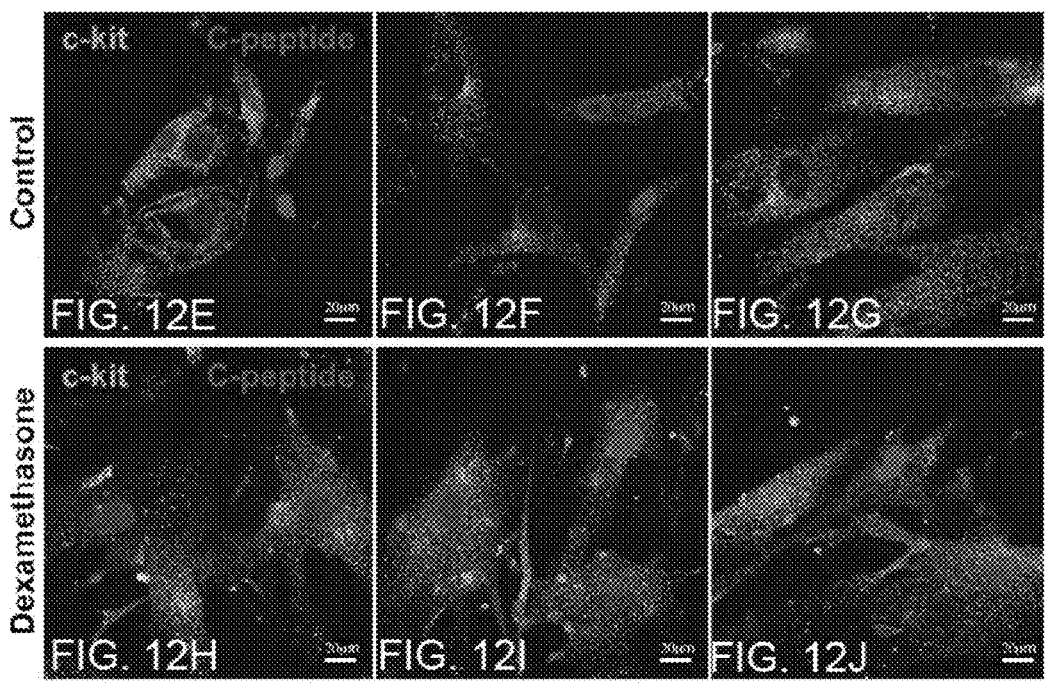
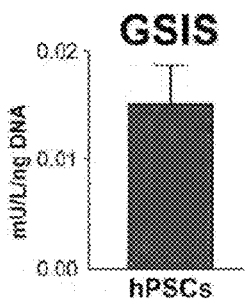
FIG. 12C - FIG. 12K

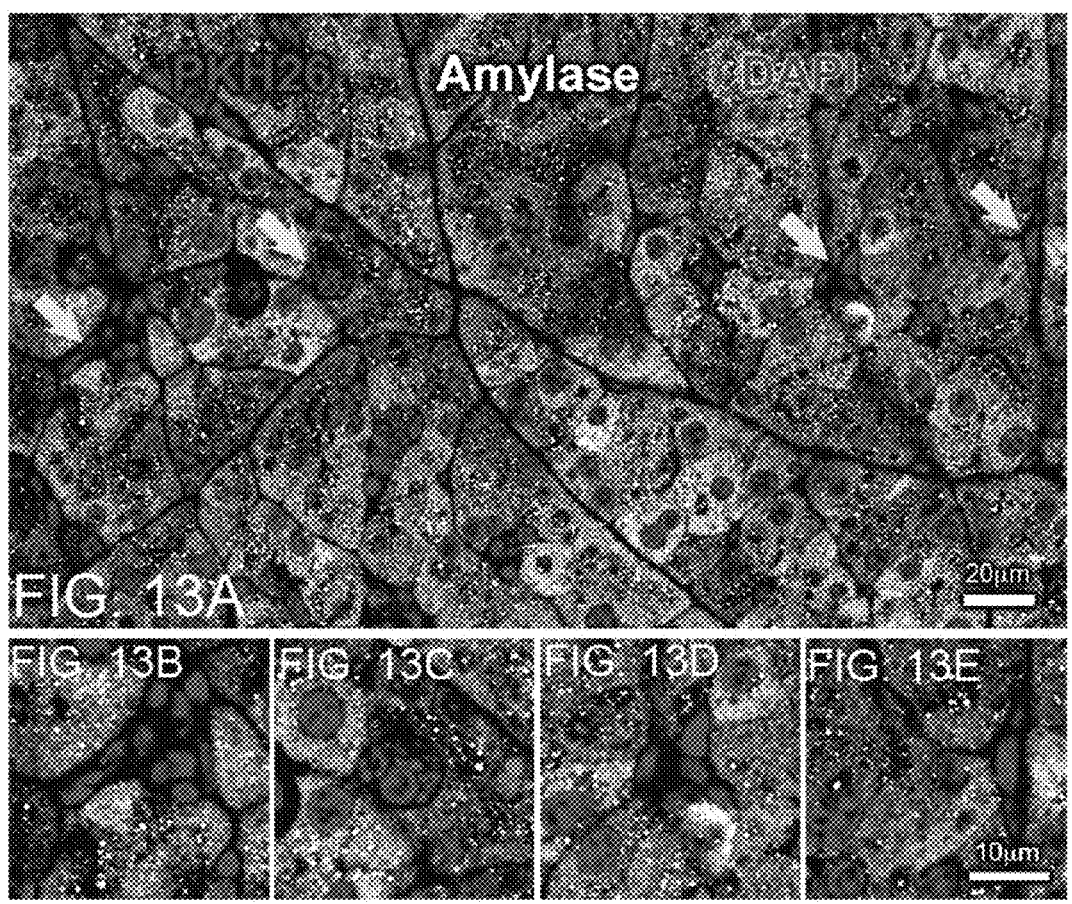
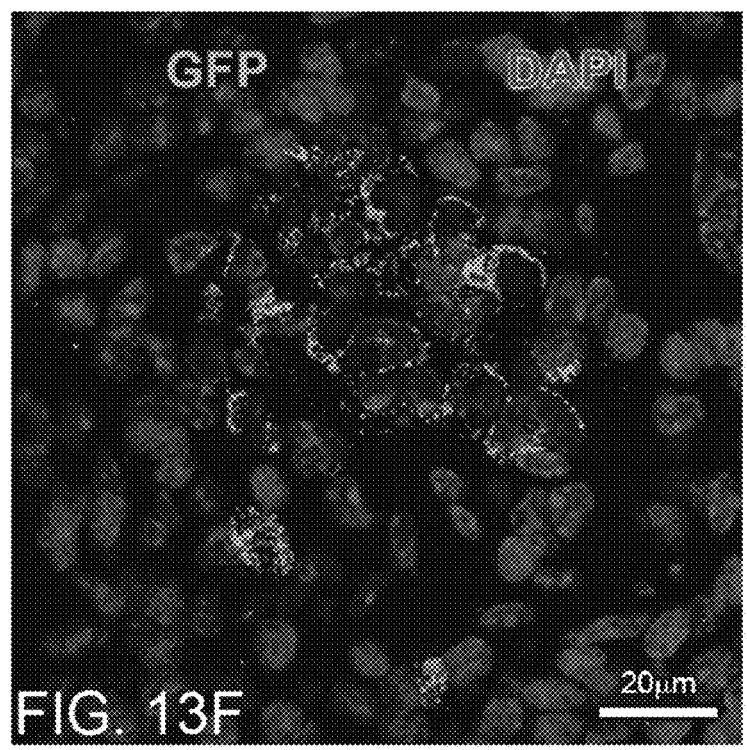
FIG. 13A - FIG. 13F

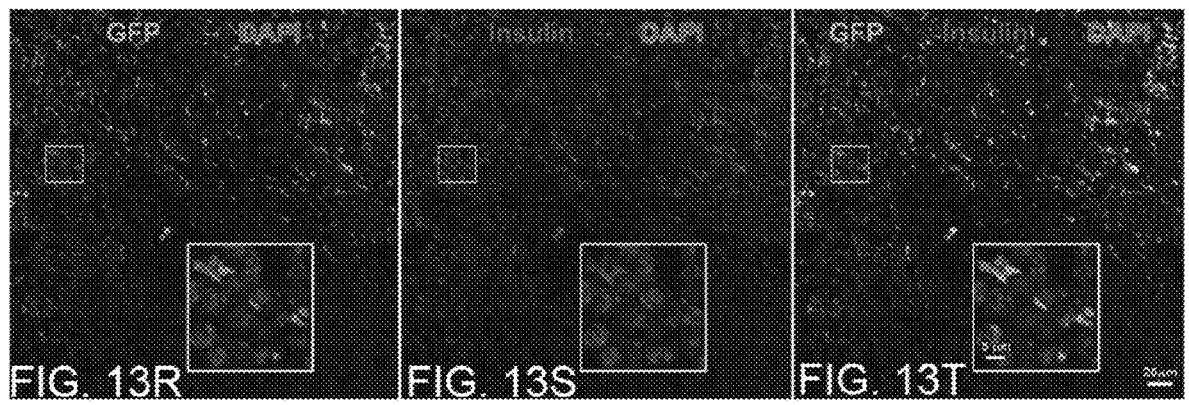
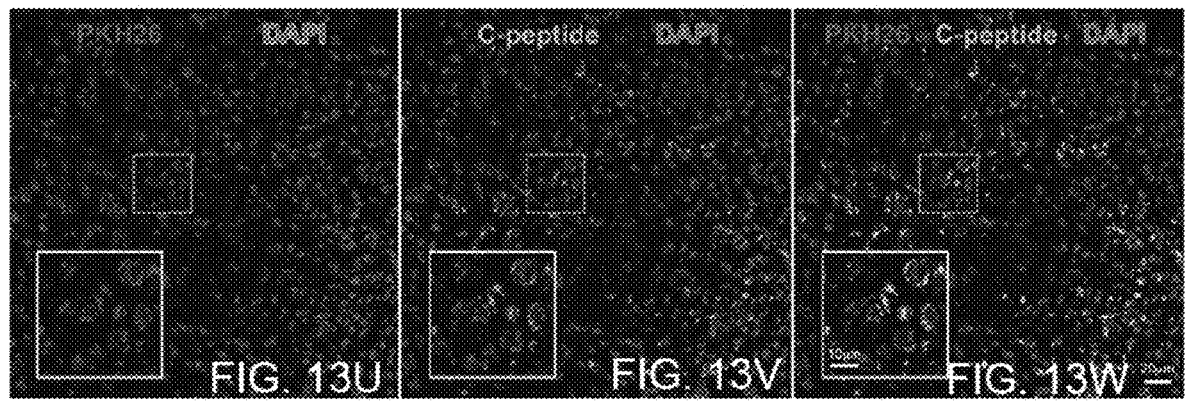
FIG. 13R - FIG. 13W

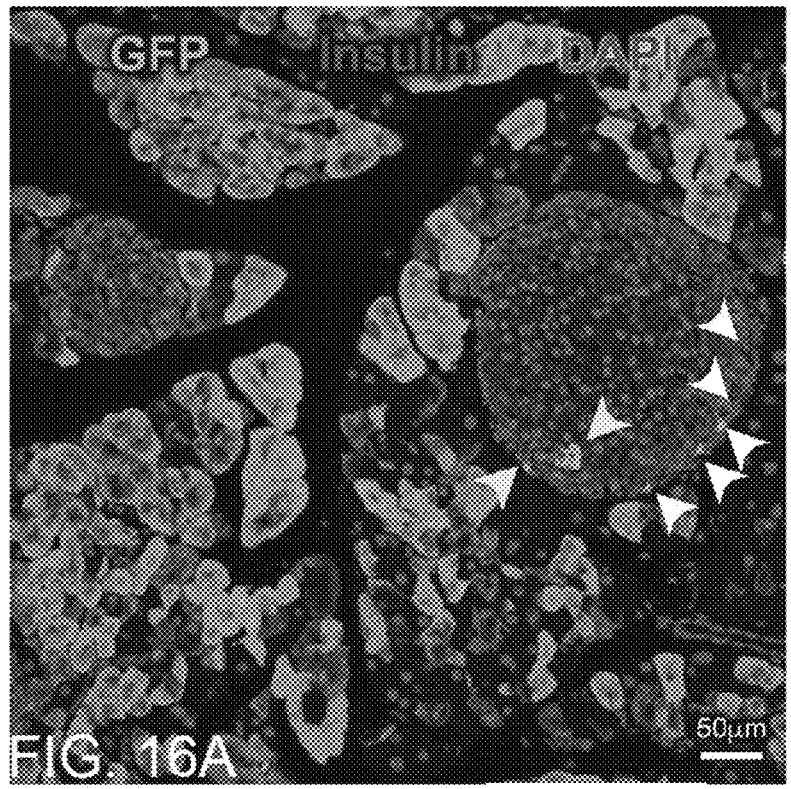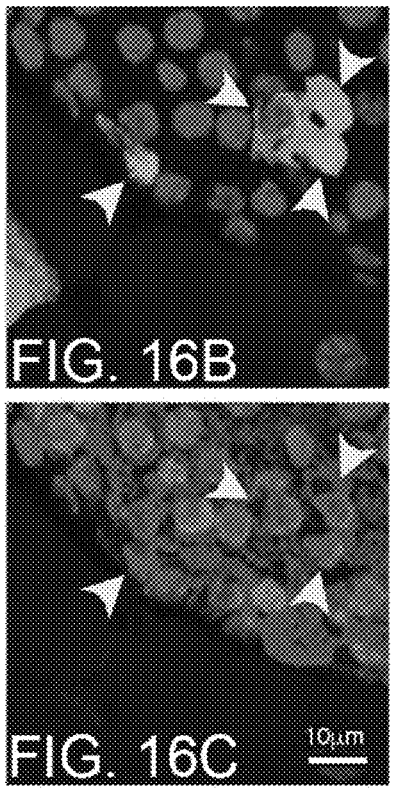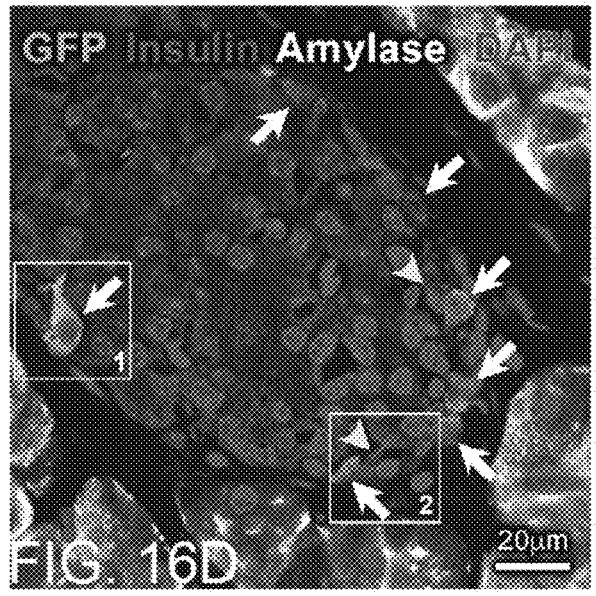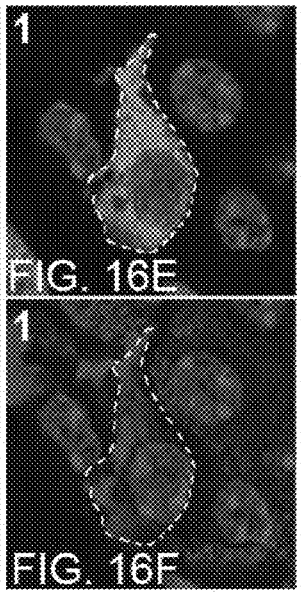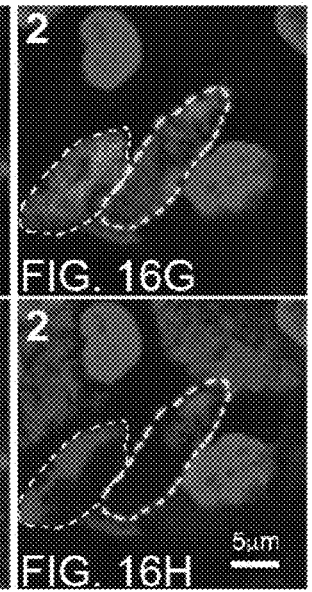
FIG. 16A - FIG. 16H

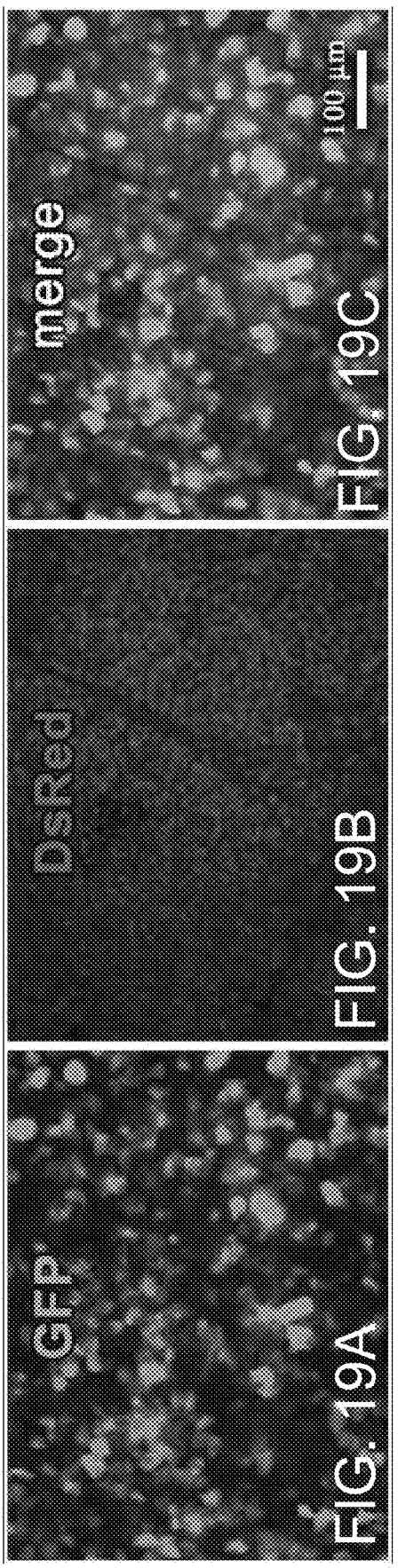
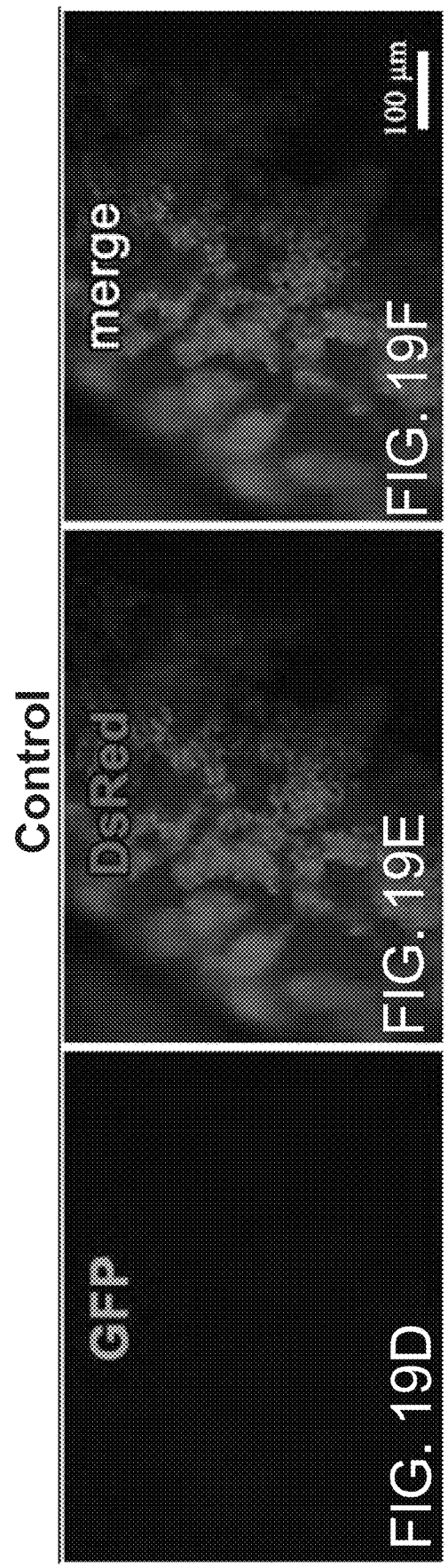
FIG. 19A – FIG. 19F

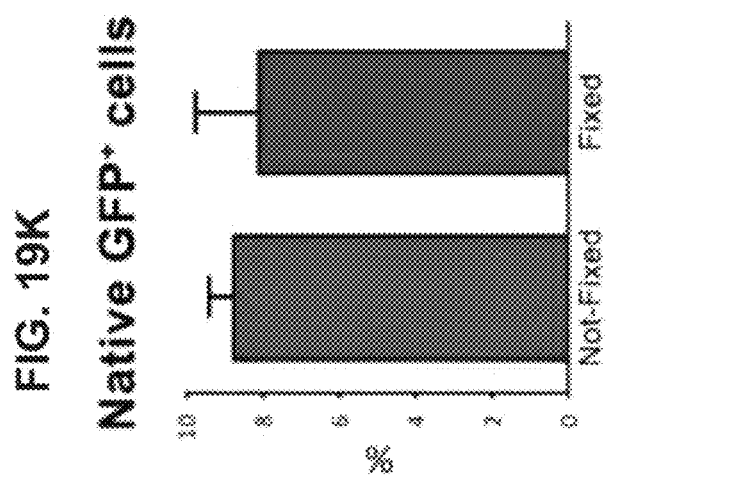
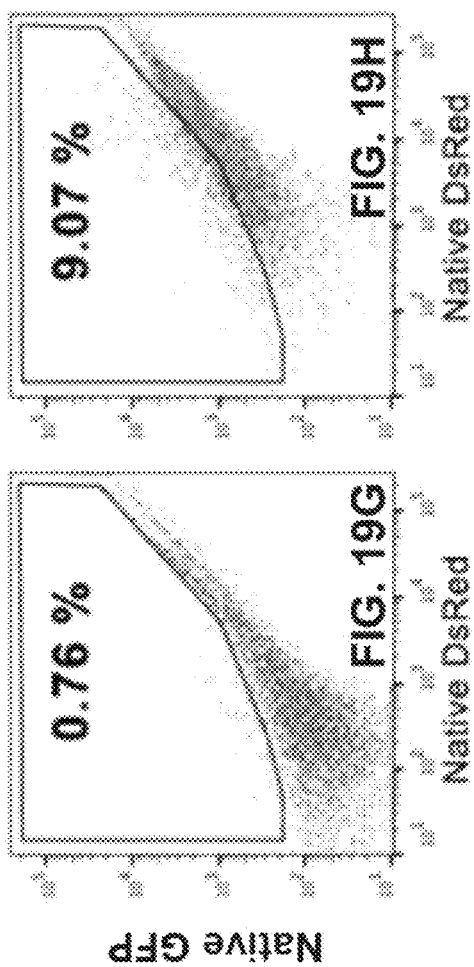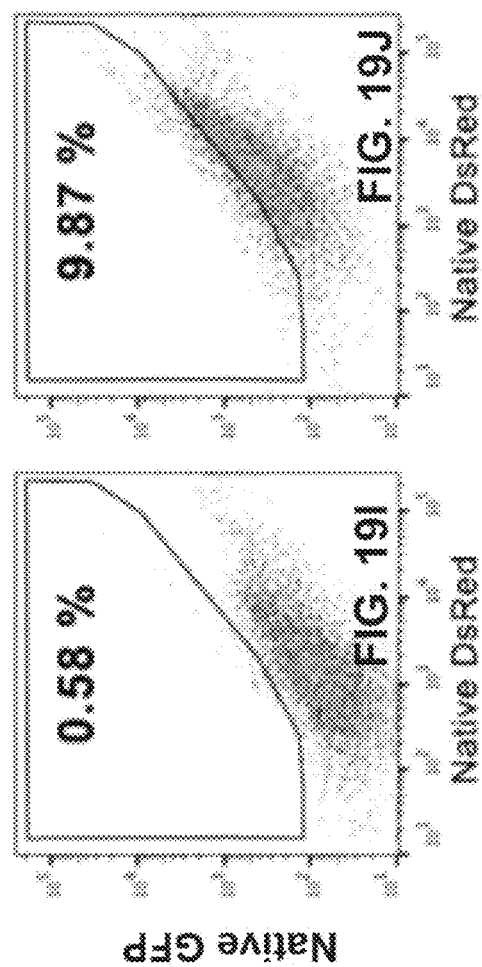
FIG. 19G – FIG. 19K

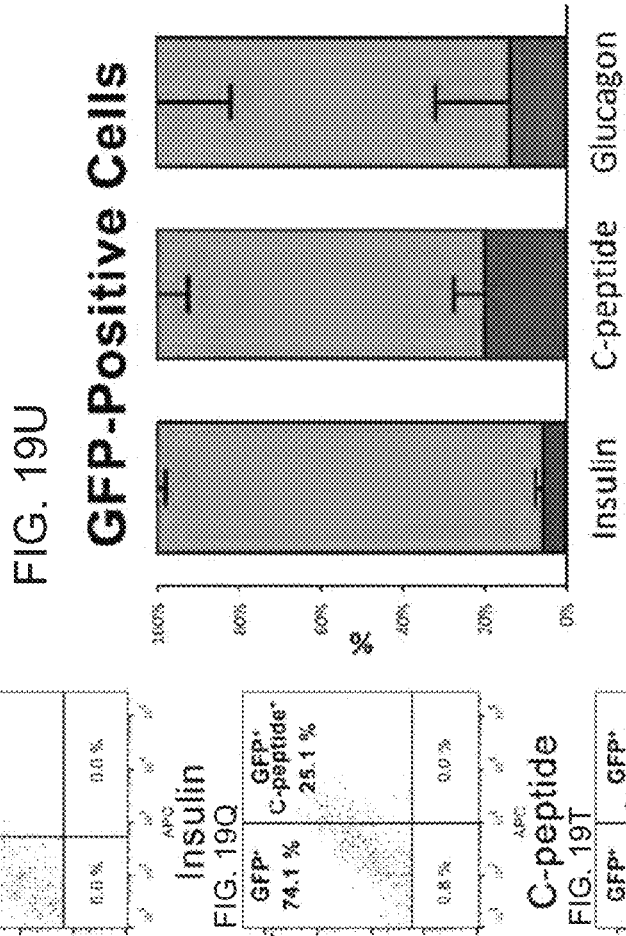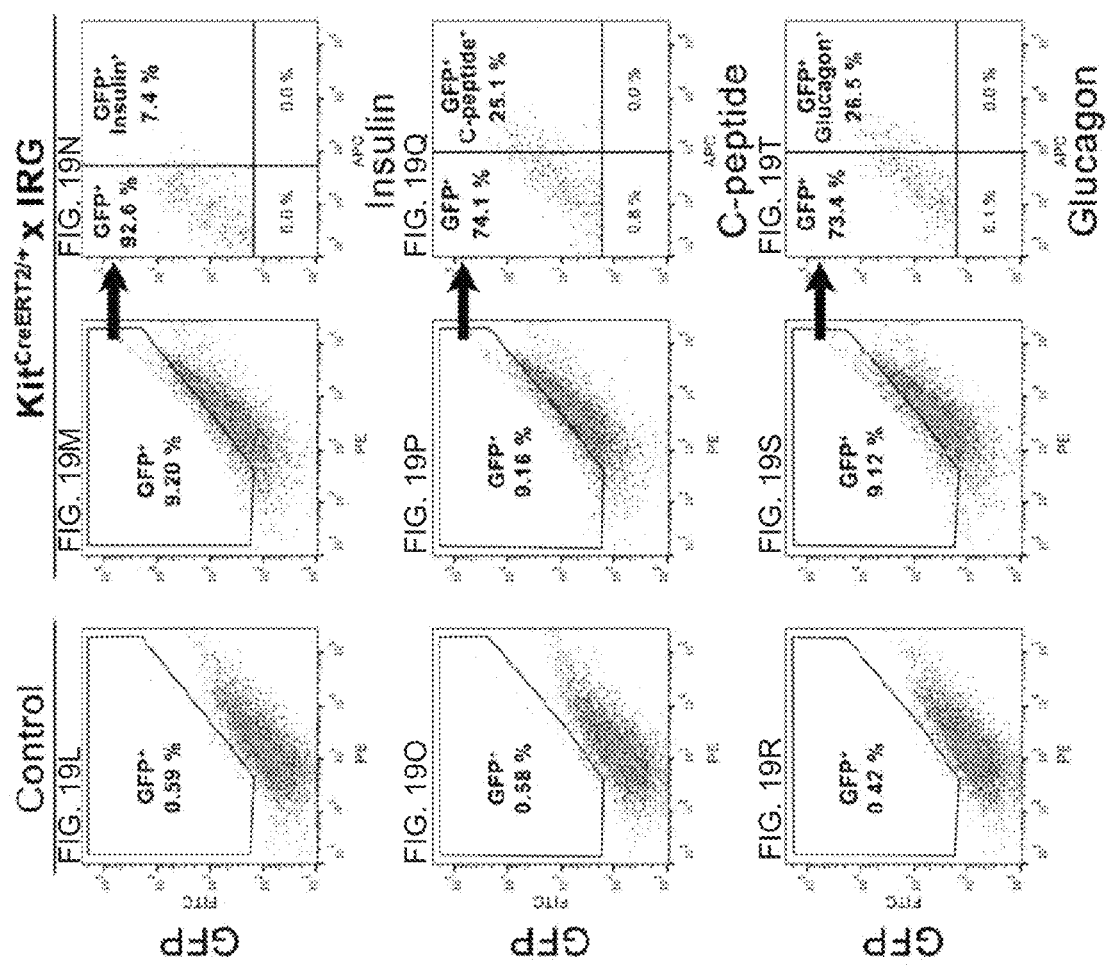

FIG. 20A
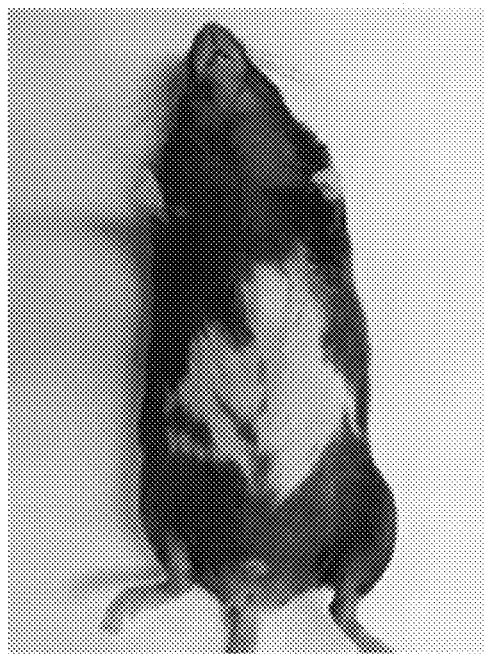
FIG. 20B
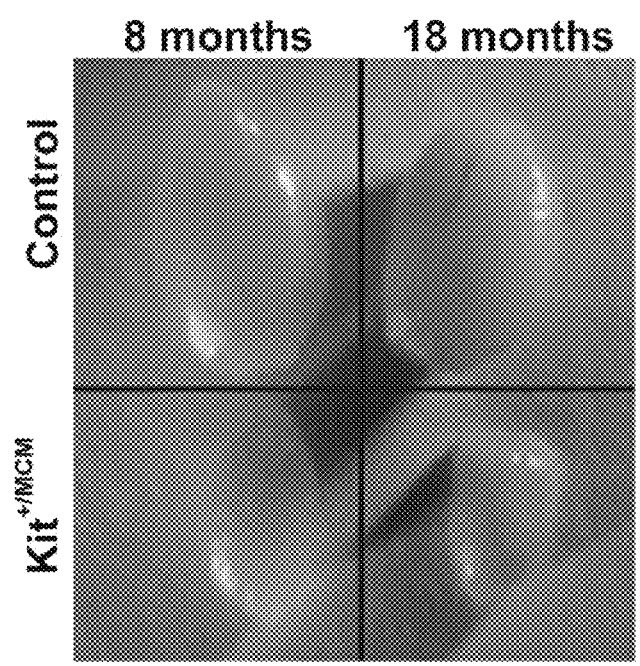
FIG. 20A - FIG. 20B

PANCREATIC STEM CELLS AND USES THEREOF

CROSS REFERENCE TO RELATED APPLICATIONS

This application claims benefit of priority to U.S. Provisional Application No. 62/305,736, filed Mar. 9, 2016, and to U.S. Provisional Application No. 62/457,710, filed Feb. 10, 2017, the contents of each of which are incorporated herein by reference in its entirety.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: AALS_005_02US_ST25.txt, date recorded: Mar. 6, 2017, file size about 3 kilobytes).

FIELD OF THE INVENTION

The present disclosure relates to stem cells and their therapeutic use in the treatment and/or prevention of pancreatic diseases or disorders. Provided herein are compositions comprising c-kit positive pancreatic stem cells and methods of preparing and using c-kit positive pancreatic stem cells for the treatment and/or prevention of pancreatic diseases or disorders.

BACKGROUND OF THE INVENTION

The pancreas is both an endocrine and exocrine gland. In its function as an endocrine gland, it produces several important hormones, including insulin, glucagon, somatostatin and pancreatic polypeptide. Insulin and glucagon are secreted from beta and alpha cells, respectively, to regulate carbohydrate, protein and lipid metabolism. The exocrine pancreas includes ductal and acinar cells, which synthesize and secrete digestive enzymes that aid in the digestion of food. Diseases and disorders associated with the pancreas include diabetes, pancreatitis, exocrine pancreatic insufficiency and cystic fibrosis.

Type 1 diabetes mellitus is a chronic medical condition that occurs when the pancreas produces very little or no insulin due to an autoimmune response. The immune system destroys the insulin-producing beta cells in the pancreas. Type 1 diabetes usually begins in childhood or young adulthood, but can develop at any age. In the United States, Canada, and Europe, type 1 diabetes accounts for 5 to 10 percent of all cases of diabetes. People who develop diabetes have one or more genes that make them susceptible to the disease. Environmental factors, such as exposure to certain viruses and foods early in life, might trigger the autoimmune response. People with type 1 diabetes are at increased risk of cardiovascular disease, which can cause heart attack, chest pain, stroke, and even death.

Type 1 diabetes requires regular blood sugar monitoring, lifestyle adjustments and treatment with insulin. In general, intensive insulin therapy is recommended for people with type 1 diabetes to keep blood sugar in tight control. Drawbacks to intensive insulin therapy include: multiple insulin shots per day or the use of an insulin pump; the need to check blood sugar frequently; the need to coordinate daily activities; increased risk of low blood sugar episodes; initial weight gain; and cost. The effectiveness of insulin action is also dependent upon dose of insulin injected, injection technique, site of injection, subcutaneous blood flow, insulin potency from opened bottles, and factors particular to each individual.

Type 2 diabetes mellitus is a chronic medical condition that disrupts the way the body uses glucose. In this disorder, the pancreas does not make enough insulin, the body becomes resistant to normal or even high levels of insulin, or both. This causes high blood glucose levels, which can cause problems if untreated. In the United States, Canada, and Europe, about 90 percent of all people with diabetes have type 2 diabetes. Type 2 diabetes is thought to be caused by a combination of genetic and environmental factors. Many people with type 2 diabetes have a family member with either type 2 diabetes or other medical problems associated with diabetes, such as high cholesterol levels, high blood pressure, or obesity. The likelihood of developing type 2 diabetes is greater in certain ethnic groups, such as people of Hispanic, African, and Asian descent.

Treatment for Type 2 diabetes includes lifestyle changes, self-care measures, and regular administration of insulin and other medications. These treatments can keep blood sugar levels close to normal and minimize the risk of developing complications.

Pancreatitis is inflammation of the pancreas and occurs when digestive enzymes start digesting the pancreas itself. Pancreatitis can be acute or chronic. Either form is serious and can lead to complications. Acute pancreatitis occurs suddenly and usually goes away in a few days with treatment. It is often caused by gallstones. Common symptoms are severe pain in the upper abdomen, nausea, and vomiting. Treatment is usually a few days in the hospital for intravenous (IV) fluids, antibiotics, and medicines to relieve pain. Chronic pancreatitis does not heal or improve. It gets worse over time and leads to permanent damage. The most common cause is heavy alcohol use. Other causes include cystic fibrosis and other inherited disorders, high levels of calcium or fats in the blood, some medicines, and autoimmune conditions. Symptoms include nausea, vomiting, weight loss, and oily stools. Treatment may also be a few days in the hospital for IV fluids, medicines to relieve pain, and nutritional support. Chronic pancreatitis is a risk factor for other disorders such as pancreatic cancer, diabetes and exocrine pancreatic insufficiency.

Exocrine pancreatic insufficiency (EPI) is the inability to properly digest food due to a lack of digestive enzymes made by the pancreas. EPI is found in humans afflicted with cystic fibrosis and Shwachman-Diamond syndrome. It is caused by a progressive loss of the pancreatic cells that make digestive enzymes. Chronic pancreatitis is the most common cause of EPI in humans. Loss of digestive enzymes leads to poor digestion and malabsorption of nutrients.

In individuals suffering from cystic fibrosis, mutations in the cystic fibrosis transmembrane conductance regulator (CFTR) leads to dysregulation of epithelial fluid transport in a number of organs, including the pancreas. The resulting fibrosis and inflammation of the pancreas can give rise to malnutrition and diabetes.

Certain types of pancreatic cancers involve cells that function abnormally. For example, acinar cell carcinoma of the pancreas may cause over production of digestive enzymes, causing symptoms such as skin rashes and joint pain. As another example, functioning types of neuroendocrine tumors secrete hormones such as insulin, gastrin and glucagon into the bloodstream in large quantities, which can lead to serious symptoms such as low blood sugar. Surgery is the only cure for exocrine type cancers, but the procedure may damage normal parts of the pancreas.

Thus, there are a variety of pancreatic diseases and disorders that would benefit from therapy that would allow repair, reconstitution and/or regeneration of cells within the pancreas. However, identification, characterization, and isolation of pancreatic stem cells from pancreas remain elusive, and there is controversy on whether such stem cells exist. Thus, there is a need in the art to identify markers of pancreatic stem cells that can be used to isolate such stem cells that can be used in therapy of pancreatic diseases or disorders.

SUMMARY OF THE INVENTION

Embodiments of the invention relate to stem cells and methods of preparing and using them.

Embodiments of the present invention are based on the discovery of a population of c-kit positive cells in pancreatic tissues that have characteristics typical of a stem cell. Prior to the discovery, there has been no recognition or isolation of one cell type from pancreatic tissues that has all the characteristics of a stem cell. The fundamental properties of stem cells are self-renewal, clonogenicity and multipotentiality in vitro and in vivo. The c-kit positive pancreatic cells are generally undifferentiated and/or express minimal levels of insulin, C-peptide, glucagon, and/or amylase.

Embodiments of the present invention provide solutions to the problem of replacing pancreatic cells damaged by pancreatic diseases or disorders such as, but not limited to, type 1 diabetes, type 2 diabetes, pancreatitis, cystic fibrosis, exocrine pancreatic insufficiency, hemosuccus pancreaticus, congenital malformations of the pancreas such as pancreas divisum and annular pancreas, and/or pancreatic cancer. In some aspects, the problems are solved by administering pancreatic stem cells to defective and/or damaged pancreatic tissue in order to promote pancreatic tissue repair and/or regeneration and to treat or prevent pancreatic diseases or disorders such as, but not limited to, type 1 diabetes, type 2 diabetes, pancreatitis, cystic fibrosis, exocrine pancreatic insufficiency, hemosuccus pancreaticus, congenital malformations of the pancreas such as pancreas divisum and annular pancreas, and/or pancreatic cancer in a subject in need thereof. In one embodiment, pancreatic stem cells are administered by implanting the cells in the patient.

Accordingly, in one aspect, the invention provides a method of treating or preventing a pancreatic disease or disorder in a subject in need thereof comprising administering isolated pancreatic stem cells to the subject, wherein the pancreatic stem cells are isolated from a pancreatic tissue specimen and are c-kit positive. In one embodiment, the pancreatic tissue specimen is obtained from the subject. In one embodiment, the pancreatic stem cells generate beta cells of the pancreas. In another embodiment, the pancreatic stem cells are characterized by their ability to differentiate into endocrine cells and/or exocrine cells. In a further embodiment, the isolated pancreatic stem cells are undifferentiated and/or express minimal levels of insulin, C-peptide, glucagon, CK19 and/or amylase.

In one embodiment, the pancreatic disease or disorder treated by the methods or compositions described herein is Type 1 diabetes. In another embodiment, the pancreatic disease or disorder is Type 2 diabetes. In another embodiment, the pancreatic disease or disorder is pancreatitis, cystic fibrosis, exocrine pancreatic insufficiency, hemosuccus pancreaticus, congenital malformations of the pancreas such as pancreas divisum and annular pancreas, and/or pancreatic cancer.

In one embodiment, said isolated pancreatic stem cells are expanded in culture prior to administration to the subject. In one embodiment, the isolated pancreatic stem cells are exposed to one or more cytokines and/or growth factors prior to administration to the subject. In another embodiment, the isolated pancreatic stem cells are exposed to Stem Cell Factor (SCF), insulin-like growth factor 1 (IGF-1), and/or hepatocyte growth factor (HGF) prior to administration to the subject.

In one embodiment, the isolated pancreatic stem cells are administered to the subject through vessels, pancreatic duct or directly to the tissue. In another embodiment, the isolated pancreatic stem cells are administered to the subject by injection or by a catheter system, or through injection in the liver.

In another aspect, the invention provides a pharmaceutical composition comprising a therapeutically effective amount of isolated pancreatic stem cells and a pharmaceutically acceptable carrier for repairing and/or regenerating damaged tissue of a pancreas, wherein said isolated pancreatic stem cells are c-kit positive. In some embodiments, the pancreatic stem cells are isolated from pancreatic tissue. In another embodiment, the isolated pancreatic stem cells are autologous.

In one embodiment, the isolated pancreatic stem cells are capable of generating one or more pancreatic cell types. In another embodiment, the one or more pancreatic cell types comprise an exocrine cell. In another embodiment, the one or more pancreatic cell types comprise an endocrine cell. In a further embodiment, the endocrine cell is an alpha cell or a beta cell. In yet another embodiment, the isolated pancreatic stem cells are undifferentiated and/or express minimal levels of insulin, C-peptide, glucagon, CK19 and/or amylase.

In one embodiment, the composition comprises about $10^6$ isolated pancreatic stem cells. In another embodiment, the isolated pancreatic stem cells are cultured and expanded in vitro. In another embodiment, the composition further comprises one or more cytokines and/or growth factors. In a further embodiment, the composition further comprises Stem Cell Factor (SCF), IGF-1, and/or HGF.

In one embodiment, the composition is formulated for catheter-mediated or direct injection.

In another aspect, the invention provides a method of isolating resident pancreatic stem cells from a pancreas comprising: (a) culturing a tissue specimen from said pancreas in culture, thereby forming a tissue explant; (b) selecting cells from the cultured explant that are c-kit positive, and (c) isolating said c-kit positive cells, wherein said isolated c-kit positive cells are resident pancreatic stem cells.

In one embodiment, said isolated c-kit positive cells express one or more markers of exocrine and/or endocrine cells. In another embodiment, the one or more markers comprise insulin, C-peptide, glucagon, CK19 and/or amylase.

In one embodiment of a method of isolating resident pancreatic stem cells from a pancreas, the isolated c-kit positive cells are capable of generating one or more pancreatic cell types. In another embodiment, the one or more pancreatic cell types comprise an exocrine cell. In another embodiment, the one or more pancreatic cell types comprise an endocrine cell. In a further embodiment, the endocrine cell is an alpha cell or a beta cell.

In one embodiment, a method of isolating resident pancreatic stem cells from a pancreas further comprises expanding said isolated c-kit positive cells in culture. In another embodiment, the method further comprises exposing said isolated c-kit positive cells to one or more cytokines and/or growth factors in culture. In yet another embodiment, the method further comprises exposing said isolated c-kit positive cells to Stem Cell Factor (SCF), IGF-1, and/or HGF in culture.

In another aspect, the invention provides a method of repairing and/or regenerating damaged tissue of a pancreas in a subject in need thereof comprising: extracting pancreatic stem cells from a pancreas; culturing and expanding said pancreatic stem cells, said pancreatic stem cells being c-kit positive stem cells; and administering a dose of said extracted and expanded pancreatic stem cells to an area of damaged tissue in the subject effective to repair and/or regenerate the damaged tissue of the pancreas.

In one embodiment of a method of repairing and/or regenerating damaged tissue of a pancreas in a subject in need thereof, the extracted and expanded c-kit positive stem cells express one or more markers of exocrine and/or endocrine cells. In another embodiment, the one or more markers comprise insulin, C-peptide, glucagon, CK19 and/or amylase.

In one embodiment of a method of repairing and/or regenerating damaged tissue of a pancreas in a subject in need thereof, the extracted and expanded c-kit positive stem cells are capable of generating one or more pancreatic cell types. In another embodiment, the one or more pancreatic cell types comprise an exocrine cell. In another embodiment, the one or more pancreatic cell types comprise an endocrine cell. In a further embodiment, the endocrine cell is an alpha cell or a beta cell.

In one embodiment of a method of repairing and/or regenerating damaged tissue of a pancreas in a subject in need thereof, the extracted and expanded c-kit positive stem cells are exposed to one or more cytokines and/or growth factors in culture prior to administration to the damaged tissue. In yet another embodiment, the extracted and expanded c-kit positive stem cells are exposed to Stem Cell Factor (SCF), IGF-1, and/or HGF prior to administration to the damaged tissue.

In one embodiment of a method of repairing and/or regenerating damaged tissue of a pancreas in a subject in need thereof, the extracted and expanded c-kit positive stem cells are administered by catheter-mediated or direct injection.

In one embodiment of all aspects of the compositions and methods described, the pancreatic tissue is from a human. In another embodiment of all aspects of the compositions and methods described, the pancreatic tissue is an adult pancreatic tissue. In another embodiment of all aspects of the compositions and methods described, the isolated pancreatic stem cells are clonogenic, multipotent and self-renewing. In another embodiment of all aspects of the compositions and methods described, the c-kit-positive cells are clonogenic, multipotent and self-renewing. In another embodiment of all aspects of the compositions and methods described, the isolated pancreatic stem cells are undifferentiated and/or express minimal levels of insulin, C-peptide, glucagon, CK19 and/or amylase. In another embodiment of all aspects of the compositions and methods described, the pancreatic stem cells are autologous. In another embodiment of all aspects of the compositions and methods described, the pancreatic stem cells are allogeneic.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 2D shows a cell stained for c-kit (green). FIG. 2E shows the same cell stained for glucagon (red). FIG. 2F shows the merge of the c-kit and glucagon stain signals.

FIG. 3B and FIG. 3C show magnifications of the boxed areas in FIG. 3A. FIG. 3B-FIG. 3C show some exocrine cells co-expressing c-kit and the epithelial marker CK19. Arrows in FIG. 3B-FIG. 3C indicate c-kit-positive cells. Cell nuclei were stained with DAPI. Tryptase stain is shown in white and is a marker for mast cells.

FIG. 8A-FIG. 8G: Three c-kit-positive cells (green, arrows, FIG. 8A, FIG. 8B-FIG. 8D) are present; the islet is stained by C-peptide (red, FIG. 8A, FIG. 8E-FIG. 8G). Nuclei are stained by DAPI (blue). The individual fluorescence channels are illustrated at higher magnification in the insets below (FIG. 8B-FIG. 8G). FIG. 8H-FIG. 8J: One c-kit positive cell (green, arrow, FIG. 8H and FIG. 8I) is present within an islet stained by insulin (red, FIG. 8H and FIG. 8J). The c-kit-positive cell is positive for insulin. Insets: individual fluorescence channels (FIG. 8I and FIG. 8J). FIG. 8K-FIG. 8R: The left and right panels show two focal planes, 6 µm apart, which illustrate two distinct c-kit-positive cells (arrows, FIG. 8K, FIG. 8L, FIG. 8O and FIG. 8P) within an islet defined by the peripheral localization of glucagon (red). Both c-kit-positive cells express glucagon (FIG. 8K, FIG. 8M, FIG. 8O and FIG. 8Q). Insets: individual fluorescence channels. One mast-cell positive for c-kit and tryptase (arrowhead, FIG. 8K and FIG. 8O) is present within the field. FIG. 8V: merge. FIG. 8W-FIG. 8Y: Proportion of c-kit-positive cells (FIG. 8W) and mast-cells (FIG. 8X) in the human pancreas (n=6). The individual data (blue bars) are shown together with their mean±SD (red bars).

FIG. 10A-FIG. 10P: putative hPSCs divide symmetrically and asymmetrically and form multicellular clones. FIG. 10A-FIG. 10B: Scatter plot of c-kit expression in pancreatic cells (right panel, FIG. 10B); in quadrant Q2, cells are positive for two distinct epitopes of the c-kit receptor. Isotype control for the two c-kit antibodies are also shown (left panel, FIG. 10A). FIG. 10L-FIG. 10M: Two single cell-derived clones shown by phase contrast microscopy. FIG. 10N-FIG. 10P: Three single cell-derived clones stained by c-kit (green) and DAPI (blue) illustrated by confocal microscopy.

FIG. 11A-FIG. 11I: growth and characteristics of pancreatic c-kit-positive cells. FIG. 11A-FIG. 11B: FACS-sorted c-kit-positive and c-kit-negative cells were plated, fixed in paraformaldehyde and stained with a third c-kit antibody, different from those employed for sorting; the c-kit-positive fraction is shown on the left panel (FIG. 11A) and c-kit-negative fraction on the right panel (FIG. 11B). FIG. 11C: FACS-sorted c-kit-positive cells were seeded individually in single wells of 96-well-plates. Clones are stained by methylene blue and are included in red circles. FIG. 11D: Data on clonal efficiency are shown individually (blue bars) and as mean±SD (red bar) (n=14). FIG. 11E-FIG. 11I: Clonal c-kit-positive cells do not express surface markers of hematopoietic cell lineages: scatter plots of expanded cells obtained from FACS-sorted c-kit-positive cells; the expression of CD34 (FIG. 11F), CD45 (FIG. 11G), CD90 (FIG. 11H) and CD105 (FIG. 11I) is shown.

FIG. 12A: Gene transcripts in clonal c-kit-positive hPSCs (n=4). FIG. 12B-FIG. 12D: The heat-map illustrates the effects of the differentiation inducer dexamethasone on the Wnt/β-catenin (FIG. 12B), TGF-β/BMP (FIG. 12C) and Notch (FIG. 12D) pathways in clonal hPSCs (n=3). FIG. 12E-FIG. 12K: Commitment of hPSCs (n=4). In each case, the upper three panels (FIG. 12E-FIG. 12G, FIG. 12L-FIG. 12N, FIG. 12R-FIG. 12T) illustrate the expression of c-kit (green) in undifferentiated cells. Following exposure to dexamethasone the expression of proinsulin C-peptide (FIG. 12H-FIG. 12J: red), glucagon (FIG. 12O-FIG. 12Q: red) and amylase (FIG. 12U-FIG. 12W: red) is apparent in each of the lower three panels. Nuclei are stained by DAPI (blue). The addition of glucose to the medium led to the synthesis of human insulin measured by the high sensitive ELISA assay (FIG. 12K). GSIS, glucose stimulated insulin secretion.

FIG. 13A-FIG. 13AA: hPSCs engraft within the mouse pancreas and acquire the endocrine and exocrine cell fate. FIG. 13A-FIG. 13E: PKH26-labeled hPSCs (red, arrows) are present within the mouse pancreas (FIG. 13A); exocrine acinar-cells are stained by amylase (white, FIG. 13A). PKH26-labeled hPSCs are illustrated at higher magnification in the insets (FIG. 13B-FIG. 13E). Nuclei are stained by DAPI (blue). FIG. 13F: Cluster of GFP-positive hPSCs (green) in the mouse pancreas. FIG. 13R-FIG. 13W: The extensively injured pancreatic tissue is replaced in part by large clusters of GFP-positive (FIG. 13R-FIG. 13T) and PKH26-positive (FIG. 13U-FIG. 13W) hPSCs. Most of hPSCs express insulin (FIG. 13S and FIG. 13T, red) or C-peptide (FIG. 13V and FIG. 13W, green). The areas included in the small squares are illustrated at higher magnification in the large squares to make more apparent the co-localization of GFP and insulin (FIG. 13R-FIG. 13T) and PKH26 and C-peptide (FIG. 13U-FIG. 13W) in differentiating β-cells. FIG. 13X-FIG. 13AA: The intact mouse pancreas has a single PKH26-labeled hPSC (red, square, FIG. 13X) which expresses amylase (white). The individual fluorescence channels for PKH26 (red, FIG. 13Y), C-peptide (green, FIG. 13Z) and amylase (white, FIG. 13AA) are illustrated at higher magnification in the insets.

FIG. 14A-FIG. 14D: A small cluster of PKH26-labeled hPSCs (red, arrow, FIG. 14A) is present within the tissue. These hPSCs are negative for C-peptide and amylase. The individual fluorescence channels for PKH26 (red, FIG. 14B), C-peptide (green, FIG. 14C) and amylase (white, FIG. 14D) are shown at higher magnification in the insets. FIG. 14E-FIG. 14H: Numerous PKH26-labeled hPSCs are present within an area of damage of the mouse pancreas. PKH26-labeled hPSCs (red, FIG. 14F) show the intracellular localization of C-peptide (green, FIG. 14G; red and green=yellow, FIG. 14E). The area included in the square is illustrated at higher magnification in the insets where the individual fluorescence channels for PKH26 (red, FIG. 14F), C-peptide (green, FIG. 14G) and amylase (white, FIG. 14H) are shown at higher magnification in the insets. Nuclei are stained by DAPI (blue).

FIG. 16A-FIG. 16O: $Kit^{+/MCM} \times R$-GFP mouse and $Kit^{+/MCM} \times mT/mG$ mouse: pancreatic cells are the progeny of c-kit-positive cells. FIG. 16A-FIG. 16C: in the $Kit^{+/MCM} \times R$-GFP mouse, exocrine acinar-cells are positive for GFP (green). β-cells positive for GFP and insulin (red) are present within an islet (white and yellow arrowheads, FIG. 16A). The two insets (right panels, FIG. 16B and FIG. 16C) illustrate the individual fluorescence channels of GFP (FIG. 16B) and insulin (FIG. 16C) for the cell cluster and single cell pointed by yellow arrowheads in the islet shown in the left panel (FIG. 16A). FIG. 16D-FIG. 16H: White arrows indicate 7 β-cells positive for GFP and insulin, and yellow arrowheads indicate two cells positive for GFP only (FIG. 16D). The cells included in squares 1 and 2 (FIG. 16D) are illustrated at higher magnification in the insets which show separately the fluorescence channels for GFP (FIG. 16E and FIG. 16G) and insulin (FIG. 16F and FIG. 16H). Inset 1 (FIG. 16E and FIG. 16F): one β-cell is positive for GFP and insulin (white dashed line). Inset 2 (FIG. 16G and FIG. 16H): one β-cell is positive for GFP and insulin (white dashed line), while the other is positive for GFP but negative for insulin (yellow dashed line). FIG. 16I-FIG. 16O: $Kit^{+/MCM} \times mT/mG$ mouse: at the periphery of the islet, two β-cells, positive for insulin (red) and GFP (green), are defined by squares (FIG. 16I) and are shown at higher magnification in the insets (FIG. 16J-FIG. 16O) where the fluorescence channels for GFP (FIG. 16J and FIG. 16M), insulin (FIG. 16K and FIG. 16N) and amylase (FIG. 16L and FIG. 16O) are illustrated separately. One cell (first three vertical insets, FIG. 16J-FIG. 16L) is positive for GFP, and negative for insulin and amylase. The other (second three vertical insets, FIG. 16M-FIG. 16O) is positive for GFP and insulin and negative for amylase. A few exocrine acinar-cells labeled by amylase (white) and positive for GFP are present in the field (FIG. 16I).

FIG. 18A: Section of the mouse pancreas with exocrine acinar-cells (amylase, white) positive for GFP (green). Five islets (insulin, red) are present and shown in detail in FIG. 18B-FIG. 18HH. FIG. 18B-FIG. 18HH: In the upper panels (FIG. 18B-FIG. 18D), several GFP-positive cells are present within the islets and 26 were selected for illustration. Of the 26 GFP-positive cells, 21 are indicated by white arrowheads and 5 by yellow arrows. These cells are documented at higher magnification in the insets shown in the center (FIG. 18E-FIG. 18S) and lower (FIG. 18T-FIG. 18HH) panels. For illustration purposes, the intensity of the green channel was increased; the intensity of the red channel was not changed. White dashed lines, which correspond to the 21 cells indicated by white arrowheads (upper panels, FIG. 18B-FIG. 18D), define β-cells positive for GFP (center panel, FIG. 18E-FIG. 18S) and insulin (lower panel, FIG. 18T-FIG. 18HH). Yellow dashed lines, which correspond to the 5 cells indicated by yellow arrows (upper panels, FIG. 18B and FIG. 18D), delimit cells positive for GFP (center panel, FIG. 18G, FIG. 18H, FIG. 18J, FIG. 18R and FIG. 18S) and negative for insulin (lower panel, FIG. 18V, FIG. 18W, FIG. 18Y, FIG. 18GG and FIG. 18HH).

FIG. 19A-FIG. 19HH: $Kit^{CreERT2/+} \times IRG$ mouse: pancreatic cells are the progeny of c-kit-positive cells. FIG. 19A-FIG. 19F: Freshly isolated pancreas. The upper three panels (FIG. 19A-FIG. 19C) document native GFP fluorescence (left, green, FIG. 19A), native DsRed fluorescence (center, red, FIG. 19B) and their combination (right, green and red, FIG. 19C). The lower three panels (FIG. 19D-FIG. 19F) do not show native GFP fluorescence (left, FIG. 19D). Only native DsRed fluorescence is present (center (FIG. 19E) and right (FIG. 19F) panels). FIG. 19G-FIG. 19K: Dot plots (FIG. 19G-FIG. 19J) showing the fraction of freshly isolated pancreatic cells labeled by native GFP (FIG. 19G and FIG. 19H), and the fraction of fixed pancreatic cells labeled by native GFP (FIG. 19I and FIG. 19J). Data are mean±SD (FIG. 19K). FIG. 19L-FIG. 19U: Dot plots (FIG. 19L-FIG. 19T) in which pancreatic cells were gated first for native GFP (FIG. 19M, FIG. 19P and FIG. 19S) and then for insulin (FIG. 19N), C-peptide (FIG. 19Q) and glucagon (FIG. 19T). The percentages of insulin, C-peptide and glucagon positive cells expressing native GFP are shown as mean±SD (FIG. 19U). Left panels (FIG. 19L, FIG. 19O and FIG. 19R): negative controls employed to set the gating strategy. FIG. 19V-FIG. 19HH: Dot plots (FIG. 19V-FIG. 19GG) in which cells were gated first for insulin (FIG. 19X), C-peptide (FIG. 19BB) and glucagon (FIG. 19FF) and then the percentages of insulin-positive, C-peptide-positive and glucagon-positive cells expressing native GFP (FIG. 19Y, FIG. 19CC and FIG. 19GG, respectively) are shown as mean±SD (FIG. 19HH). Left panels (FIG. 19V, FIG. 19W, FIG. 19Z, FIG. 19AA, FIG. 19DD and FIG. 19EE): negative controls employed to set the gating strategy.

FIG. 20A-20B: $Kit^{+/MCM} \times R$-GFP Mouse. FIG. 20A: White belly spot in a non-tamoxifen-treated transgenic mouse. FIG. 20B: Testes in age-matched control wild-type mice (upper panels). In the absence of tamoxifen treatment, testicular atrophy is apparent in 8 month-old (lower left panel) and 18 month-old (lower right panel) transgenic mice.

DETAILED DESCRIPTION OF THE INVENTION

Figure 1:
FIG. 1 shows a representative human pancreas sample obtained at surgery.

Embodiments of the present invention are based on the discovery of a population of c-kit positive cells in pancreatic tissues that have characteristics typical of a stem cell. The fundamental properties of stem cells are the ability to self-renew (i.e., make more stem cells), clonogenicity and multipotentiality in vitro and in vivo. Prior to this discovery, there has been no recognition or isolation of one cell type from pancreatic tissues that exhibits all three characteristics of a stem cell.

As it is well known, stem cells, by virtue of their properties, give rise to all the cells and tissues of the body. Therefore, stem cells can be used to repair or speed up the repair of a damaged and/or defective pancreas. If a sufficient amount of pancreatic stem cells (PSCs) can be obtained, this amount of PSCs can be used to repair damaged and/or defective pancreas by building new tissues in the pancreas.

In a defective and/or damaged pancreas, there may be few or absent PSCs. Because PSCs self-renew, the implanted PSCs can colonize and populate niches in the defective and/or damaged pancreas. By being clonal and multipotent, the implanted PSCs can also divide and differentiate to produce all new pancreatic cells and tissues. Therefore, a population of isolated PSCs or a composition comprising a population of isolated PSCs can be used for treatment or prevention of a pancreatic disease or disorder in a subject.

Accordingly, in one embodiment, the invention provides a population of isolated cells from a sample of pancreatic tissue, wherein the population of isolated cells contains c-kit positive PSCs. This population of c-kit-positive PSCs can be enriched and expanded significantly.

In one embodiment, provided herein is a pharmaceutical composition comprising a therapeutically effective amount of isolated and expanded pancreatic stem cells and a pharmaceutically acceptable carrier for repairing and/or regenerating damaged tissue of a pancreas, wherein said isolated pancreatic stem cells are c-kit positive. In another embodiment, the pancreatic stem cells are adult (e.g., non-embryonic and/or non-fetal) pancreatic stem cells. In another embodiment, the isolated pancreatic stem cells are clonogenic, multipotent and self-renewing. In some embodiments, the pancreatic stem cells are isolated from pancreatic tissue. In another embodiment, the isolated pancreatic stem cells are human cells. In another embodiment, the isolated pancreatic stem cells are autologous.

In some embodiments, the isolated pancreatic stem cells are capable of generating one or more pancreatic cell types. In one embodiment, the one or more pancreatic cell types comprise an exocrine cell. In another embodiment, the one or more pancreatic cell types comprise an endocrine cell. In a further embodiment, the endocrine cell is an alpha cell or a beta cell. In yet another embodiment, the isolated pancreatic stem cells are undifferentiated and/or express minimal levels of insulin, C-peptide, glucagon, CK19 and/or amylase.

In one embodiment, the composition comprises about $10^6$ isolated pancreatic stem cells. In another embodiment, the isolated pancreatic stem cells are cultured and expanded in vitro. In another embodiment, the composition further comprises one or more cytokines and/or growth factors. In a further embodiment, the composition further comprises Stem Cell Factor (SCF), IGF-1, and/or HGF.

In one embodiment, the composition is formulated for catheter-mediated or direct injection.

In one embodiment, provided herein is a composition for use in the manufacture of a medicament for the treatment and/or prevention of a pancreatic disease or disorder in a subject, the composition comprising an enriched population of isolated c-kit positive PSCs from a pancreatic tissue sample. In another embodiment of this composition, the composition further comprises a pharmaceutically acceptable carrier.

In one embodiment, the invention provides a method of isolating resident pancreatic stem cells from a pancreas comprising: (a) culturing a tissue specimen from said pancreas in culture, thereby forming a tissue explant; (b) selecting cells from the cultured explant that are c-kit positive, and (c) isolating said c-kit positive cells, wherein said isolated c-kit positive cells are resident pancreatic stem cells.

In one embodiment, said isolated c-kit positive cells express one or more markers of exocrine and/or endocrine cells. In another embodiment, the one or more markers are insulin, C-peptide, glucagon, CK19 and/or amylase.

In some embodiments of a method of isolating resident pancreatic stem cells from a pancreas, the isolated c-kit positive cells are capable of generating one or more pancreatic cell types. In one embodiment, the one or more pancreatic cell types comprise an exocrine cell. In another embodiment, the one or more pancreatic cell types comprise an endocrine cell. In a further embodiment, the endocrine cell is an alpha cell or a beta cell.

In one embodiment, a method of isolating resident pancreatic stem cells from a pancreas further comprises expanding said isolated c-kit positive cells in culture. In another embodiment, said isolated c-kit positive cells are clonogenic, multipotent and self-renewing. In another embodiment, the method further comprises exposing said isolated c-kit positive cells to one or more cytokines and/or growth factors in culture. In yet another embodiment, the method further comprises exposing said isolated c-kit positive cells to Stem Cell Factor (SCF), IGF-1, and/or HGF in culture.

In one embodiment, the invention provides a method of obtaining a population of isolated cells substantially enriched for c-kit positive PSCs, the method comprising cryopreserving a specimen of pancreatic tissue obtained from a subject; thawing the cryopreserved specimen at a later date; selecting one or more c-kit positive cells from the specimen of pancreatic tissue; and proliferating the selected c-kit positive cells in a culture medium.

In one embodiment, the invention provides a method of proliferating a population of isolated cells substantially enriched for c-kit positive PSCs, the method comprising selecting one or more c-kit positive cells from a pancreatic tissue sample; introducing the one or more c-kit positive selected cells to a culture medium; and proliferating the selected c-kit positive cells in the culture medium.

In another embodiment, the invention provides methods of use of this population of isolated cells that is substantially enriched for c-kit positive PSCs or use of a pharmaceutical composition comprising an enriched population of isolated c-kit positive PSCs, for example, in the repair, regeneration and/or treatment of pancreatic diseases or disorders such as type 1 diabetes, type 2 diabetes, pancreatitis, cystic fibrosis, exocrine pancreatic insufficiency, hemosuccus pancreaticus, congenital malformations of the pancreas such as pancreas divisum and annular pancreas, and/or pancreatic cancer. Without wishing to be bound by theory, the inventors consider that the c-kit-positive-cells identified in pancreatic tissue may represent the source of the specialized cells in the pancreas, such as the glucagon-secreting alpha cells, the insulin-secreting beta cells, the somatostatin-releasing delta cells, the ghrelin-producing epsilon cells, the pancreatic polypeptide-secreting PP cells, the exocrine acinar cells, the exocrine centroacinar cells, and/or the exocrine ductal cells. Hence, in one embodiment, a population of isolated c-kit positive PSCs which have been expanded in vitro can be transplanted or implanted into an affected/damaged pancreas. The c-kit positive PSCs then take up residence in the pancreas, grow and differentiate into the various types of tissues normally found in a pancreas, and restore and/or reconstitute the exocrine and endocrine cells. The goal is to replace at least some of the pancreatic tissue damaged due to disease in the affected pancreas. The replacement pancreatic tissue serves to supplement existing or remaining pancreatic tissue in the affected subject so that over all there is enough tissue for adequate digestive and/or endocrine functions of the pancreas to ameliorate, treat and/or prevent pancreatic disease or disorder in that subject.

In one embodiment, differentiated c-kit-positive PSCs can be transplanted into the abdominal fat pads of severe combined immunodeficient (SCID)/non-obese diabetic (NOD) mice to establish whether PSCs can differentiate into insulin-producing β cells to thus ameliorate, treat and/or prevent diabetes in the mice.

There is no literature that demonstrates the presence of bona fide multipotent tissue-specific adult stem cells in the adult pancreas and the use of these PSCs to treat or prevent pancreatic diseases or disorders in patients. The advantage of the present invention is that the PSCs used in treatment or prevention of pancreatic diseases or disorders can be autologous cells which will greatly increase success rate of treatment or prevention. A portion of a patient's pancreas is removed surgically, e.g., during a biopsy. As little as one cubic centimeter is sufficient. The piece of tissue is treated to release single cells from the sampled pancreatic tissue. Using the stem cell marker, c-kit, as an indication of stem cell identity, c-kit positive cells are selected. The c-kit positive PSCs are then expanded in vitro to obtain sufficient number of cells required for treatment or prevention. When there are enough cells, the cells are harvested and injected back into the same patient or a genetically matched patient with respect to the donor of the PSCs. At each transitional step, e.g., between selection and expansion or between expansion and implanting, the PSCs can be optionally cryopreserved. In one embodiment, the patient gets back the patient's own PSCs that have been selected and expanded in vitro. In another embodiment, the patient gets the PSCs derived from a genetically matched donor. In some embodiments, this method can also be extended to any mammal that has a pancreas, e.g., cat, dog, horse, monkey, etc.

Accordingly, the invention provides a method of treating or preventing a pancreatic disease or disorder in a subject in need thereof comprising administering isolated pancreatic stem cells to the subject, wherein the pancreatic stem cells are isolated from a pancreatic tissue specimen and are c-kit positive. In one embodiment, the pancreatic tissue specimen is obtained from the subject. In one embodiment, the pancreatic stem cells generate beta cells of the pancreas. In another embodiment, the pancreatic stem cells are characterized by their ability to differentiate into endocrine cells and/or exocrine cells. In a further embodiment, the isolated pancreatic stem cells are undifferentiated or express minimal levels of insulin, C-peptide, glucagon, CK19 and/or amylase.

In one embodiment, the pancreatic disease or disorder is Type 1 diabetes. In another embodiment, the pancreatic disease or disorder is Type 2 diabetes. In further embodiments, the pancreatic disease or disorder is pancreatitis, cystic fibrosis, exocrine pancreatic insufficiency, hemosuccus pancreaticus, congenital malformations of the pancreas such as pancreas divisum and annular pancreas, and/or pancreatic cancer.

In some embodiments, said isolated pancreatic stem cells are expanded in culture prior to administration to the subject. In one embodiment, the isolated pancreatic stem cells are exposed to one or more cytokines and/or growth factors prior to administration to the subject. In another embodiment, the isolated pancreatic stem cells are exposed to Stem Cell Factor (SCF), insulin-like growth factor 1 (IGF-1), and/or hepatocyte growth factor (HGF) prior to administration to the subject.

In some embodiments, the isolated pancreatic stem cells are administered to the subject through vessels, pancreatic duct or directly to the pancreatic tissue. In another embodiment, the isolated pancreatic stem cells are administered to the subject by injection or by a catheter system or through injection in the liver.

In some embodiments, the isolated pancreatic stem cells may be implanted in a patient in an encapsulating device (see, e.g., U.S. Pat. Nos. 9,132,226 and 8,425,928, the contents of each of which are incorporated herein by reference in their entirety). In one embodiment, the patient has diabetes, and the PSCs implanted in an encapsulating device produce insulin in the patient.

In one embodiment, provided here is a method for treating and/or preventing a pancreatic disease or disorder in a subject in need thereof, the method comprising administering a composition comprising a population of c-kit positive PSCs described herein to the subject.

In another embodiment, the invention provides a method for treating and/or preventing a pancreatic disease or disorder in a subject in need thereof, comprising obtaining a sample of pancreatic tissue from a subject; extracting a population of c-kit positive PSCs from the pancreatic tissue sample; expanding the selected c-kit positive PSCs in vitro to increase the numbers of such PSCs; and administering the expanded population of c-kit positive PSCs to the subject to repair, reconstitute and/or regenerate exocrine and/or endocrine cells and tissues in the pancreas of the subject.

In another embodiment, the invention provides a method for treating or preventing a pancreatic disease or disorder in a subject in need thereof, the method comprising obtaining pancreatic tissue from a first subject; extracting a population of c-kit positive PSCs from the pancreatic tissue sample; expanding the population of c-kit positive PSCs; and administering the population of c-kit positive PSCs to a second subject for the c-kit PSCs to take up residence in the pancreas and repair, reconstitute, and/or regenerate exocrine and/or endocrine cells and tissues in the pancreas of the second subject.

In another embodiment, the invention provides a method of repairing and/or regenerating damaged tissue of a pancreas in a subject in need thereof comprising: extracting pancreatic stem cells from a pancreas; culturing and expanding said pancreatic stem cells, said pancreatic stem cells being c-kit positive stem cells; and administering a dose of said extracted and expanded pancreatic stem cells to an area of damaged tissue in the subject effective to repair and/or regenerate the damaged tissue of the pancreas.

In one embodiment of a method of repairing and/or regenerating damaged tissue of a pancreas in a subject in need thereof, the extracted and expanded c-kit positive stem cells express one or more markers of exocrine and/or endocrine cells. In another embodiment, the one or more markers are insulin, C-peptide, glucagon, CK19 and/or amylase.

In some embodiments of a method of repairing and/or regenerating damaged tissue of a pancreas in a subject in need thereof, the extracted and expanded c-kit positive stem cells are capable of generating one or more pancreatic cell types. In one embodiment, the one or more pancreatic cell types comprise an exocrine cell. In another embodiment, the one or more pancreatic cell types comprise an endocrine cell. In a further embodiment, the endocrine cell is an alpha cell or a beta cell.

In one embodiment of a method of repairing and/or regenerating damaged tissue of a pancreas in a subject in need thereof, the extracted and expanded c-kit positive stem cells are exposed to one or more cytokines and/or growth factors in culture prior to administration to the damaged tissue. In yet another embodiment, the extracted and expanded c-kit positive stem cells are exposed to Stem Cell Factor (SCF), IGF-1, and/or HGF prior to administration to the damaged tissue.

In one embodiment of a method of repairing and/or regenerating damaged tissue of a pancreas in a subject in need thereof, the extracted and expanded c-kit positive stem cells are administered by catheter-mediated or direct injection.

In one embodiment of all aspects of the compositions and methods described, the c-kit positive PSCs that make up predominantly the population of isolated cells have self-renewal capability, clonogenicity and multipotentiality. This means that each isolated c-kit positive cell can divide to give rise to more c-kit positive cells, forming a colony in culture. When stimulated under certain conditions, each c-kit positive cell can become committed (i.e., selecting a specific cell lineage to differentiate into) and further differentiate to cells of a specific lineage, e.g., an alpha cell, a beta cell, a delta cell, an epsilon cell, a PP cell, an acinar cell, a centroacinar cell or a ductal cell. These cells and their progeny, upon specification and differentiation, will express the particular cell markers characteristic of the determined lineage. In addition, the committed cell and its progeny will lose the expression of c-kit.

In one embodiment of all aspects of the compositions and methods described, the pancreatic tissue is from a human. In another embodiment of all aspects of the compositions and methods described, the human is an adult.

In one embodiment of all aspects of the described methods, the pancreatic tissue is cryopreserved prior to selecting c-kit positive cells.

In one embodiment of all aspects of the described methods, the selection of the c-kit-positive PSCs is performed using an antibody against c-kit.

In one embodiment of all aspects of the described methods, the antibody against c-kit is a monoclonal antibody.

In one embodiment of all aspects of the described methods, the monoclonal antibody against c-kit is a mouse monoclonal IgG against an antigenic epitope of human c-kit.

In one embodiment of the any of the described methods, the antibody against c-kit is fluorochrome conjugated.

In one embodiment of all aspects of the described methods, the antibody against c-kit is conjugated to magnetic particles.

In one embodiment of all aspects of the described methods, the selection of c-kit positive cells is by flow cytometry.

In one embodiment of all aspects of the described methods, the selection is by fluorescence activated cell sorting or high gradient magnetic selection.

In another embodiment of all aspects of the compositions and methods described, the isolated pancreatic stem cells are undifferentiated and/or express minimal levels of insulin, C-peptide, glucagon, CK19 and/or amylase.

In one embodiment of all aspects of the described methods, the c-kit positive PSCs are further expanded ex vivo. In one embodiment of all aspects of the described methods, the c-kit positive PSCs are further expanded in vitro. In certain aspects, the goal is to have a sufficiently large amount of c-kit positive PSCs for implanting to ensure successful engrafting of the implanted PSCs into niches of the damaged pancreas. Basically, there must be sufficient cells to grow and multiply in the damaged pancreas to provide all the cells needed to repair and/or replace the damaged parts of the pancreas.

In one embodiment of all aspects of the described methods, the c-kit positive PSCs are at least double in number after the expansion or proliferation step. In some embodiments of all aspects of the described methods, it is desirable that the number of c-kit positive cells, upon expansion or proliferation, is increased by at least 5 fold, 10 fold, 20 fold, 50 fold, 100 fold, 200 fold, 500 fold, 1000 fold, 2000 fold, 5000 fold, 10,000 fold, 20,000 fold, 50,000 fold or more at the end of the proliferation phase. The number of cells in a culture can be determined by any methods known in the art, e.g., by using a coulter counter. These methods are well known to those skilled in the art.

In one embodiment of all aspects of the described methods, the selected c-kit positive PSCs are cryopreserved for storage prior to expansion.

In another embodiment of all aspects of the described methods, the expanded PSCs are cryopreserved for storage purposes. When needed, the frozen cells are thawed and then used for administering to or implanting into a subject in need thereof.

In one embodiment of all aspects of the described methods, the method further comprises cyropreserving the population of isolated c-kit positive PSCs.

For a person who has been newly diagnosed with a pancreatic disease or disorder, if a biopsy sample of the subject's pancreas was obtained for the diagnosis, a population of c-kit positive PSCs can be prepared according to the methods described here and the PSCs can then be cyropreserved for future use in the event that the disease had progressed to an advanced stage such that the person needed pancreatic stem cell therapy.

Similarly, a person who is at risk of developing a pancreatic disease or disorder can benefit from early preparation of a population of c-kit PSCs from the person's own pancreatic tissue and cyropreserving the PSCs. For example, a person with a genetic disposition to diabetes or who has immediate relatives with diabetes would benefit. The lifetime risk of developing type 2 diabetes is 5 to 10 times higher in first-degree relatives (sister, brother, son, daughter) of a person with diabetes compared with a person with no family history of diabetes. Other people at risk of developing pancreatic diseases or disorders include, but are not limited to: a person carrying a cystic fibrosis gene or is diagnosed with cystic fibrosis; and an individual diagnosed with pancreatitis, exocrine pancreatic insufficiency, hemosuccus pancreaticus, congenital malformations of the pancreas such as pancreas divisum and annular pancreas, and/or pancreatic cancer.

In some embodiments of all aspects of the therapeutic methods, treating and treatment includes "restoring structural and functional integrity" to a damaged pancreas in a subject in need thereof.

In other embodiments of all aspects of the described methods, treating includes repairing damaged or inadequate human pancreas. In another embodiment, treating and treatment includes repair, reconstitution and/or regeneration of exocrine and/or endocrine cells and tissues in the damaged pancreas.

The restoring or repairing need not be to 100% to that of the pancreas of a healthy person. As long as there is an improvement in the symptoms in the subject, restoring or repairing has been achieved. A skilled physician would be able to assess the severity of the symptoms before and after the treatment and based on a comparison determine whether there is an improvement. Often, the subject will be able to say whether there is an improvement in the symptoms. Examples of some symptoms include, but are not limited to: frequent urination, increased thirst, increased hunger, blurred vision, weight loss, lethargy, hyperventilation (for diabetes); abdominal pain, nausea, vomiting (diabetes, pancreatitis).

In one embodiment of all aspects of the therapeutic methods, preventing and prevention includes slowing down the reduced functioning capacity and integrity of the pancreas due to disease, e.g., from cystic fibrosis, pancreatitis or diabetes.

In one embodiment of all aspects of the therapeutic methods, the population of c-kit positive PSCs repairs, reconstitutes or generates exocrine and/or endocrine cells and tissues in the pancreas.

In one embodiment of all aspects of the therapeutic methods, the method of treating and/or preventing a pancreatic disease or disorder further comprises selecting a subject who is suffering from a pancreatic disease or disorder prior to administering the population of cells that is substantially enriched for c-kit positive PSCs, e.g., a subject suffering from cystic fibrosis, pancreatitis or diabetes.

In one embodiment of all aspects of the therapeutic methods, the method of treating and/or preventing a pancreatic disease or disorder further comprises selecting a subject in need of restoring the structural and functional integrity of a damaged pancreas prior to administering the cells, e. g. a subject suffering from cystic fibrosis, pancreatitis or diabetes.

In one embodiment of all aspects of the therapeutic methods, the method of treating and/or preventing a pancreatic disease or disorder further comprises selecting a subject in need of treatment, prevention or repair or reconstitution or generation of exocrine and/or endocrine cells and tissues in the pancreas, e.g., a subject suffering from cystic fibrosis, pancreatitis or diabetes.

For example, the selected subjects are those who have not responded at all or well to the traditional treatment and/or one who has exhausted all therapeutic options currently known in the art for a particular form or type of a pancreatic disease or disorder.

In one embodiment of all aspects of the therapeutic methods for treating or preventing a pancreatic disease or disorder, the administration is by injection, by a catheter system, or a combination thereof.

In one embodiment of all aspects of the therapeutic methods for treating or preventing a pancreatic disease or disorder, the administration to the subject is through vessels, pancreatic duct, directly to the tissue, or a combination thereof.

In one embodiment of all aspects of the therapeutic methods for treating or preventing a pancreatic disease or disorder, the administration to the subject is implantation in a patient in an encapsulating device.

In one embodiment of all aspects of the therapeutic methods for treating or preventing a pancreatic disease or disorder, the c-kit positive PSCs are autologous cells.

In one embodiment of all aspects of the therapeutic methods for treating or preventing a pancreatic disease or disorder, the c-kit positive PSCs are allogeneic cells obtained from one or more donors.

In one embodiment of all aspects of the therapeutic methods, the method further comprises administration with at least one therapeutic agent with the c-kit positive PSCs, e.g., those for treating cystic fibrosis, pancreatitis or diabetes.

In one embodiment of all aspects of the therapeutic methods, the at least one therapeutic agent enhances homing, engraftment, or survival of the population of PSCs.

In one embodiment of all aspects of the therapeutic methods, the subject is a mammal, preferably a human. In another embodiment, the subject is an adult human. In one embodiment, the population of c-kit positive PSCs is a population of c-kit positive human PSCs.

Pancreatic Development

The pancreas is composed of an endocrine compartment and an exocrine compartment derived from endoderm. The endocrine compartment has hormone-secreting cells organized into islets, while the exocrine compartment has acinar, ductal and centroacinar cells.

There are five different hormone-secreting cell types in the endocrine compartment: glucagon-secreting alpha cells; insulin-secreting beta cells; somatostatin-releasing delta cells; ghrelin-producing epsilon cells; and pancreatic polypeptide-secreting PP cells. The hormones are responsible for regulating nutrient metabolism and glucose homeostasis. The endocrine cells aggregate to form the islets of Langerhans, which are intermingled with blood vessels, neurons, and a mesodermally-derived stromal component. The intimate association of endocrine and vascular cells regulates hormone release, establishing a fine-tuned glucose homeostasis in the body.

Acinar cells synthesize and secrete digestive enzymes, which are concentrated into a bicarbonate rich fluid that travels through a complex network of ducts to empty into the duodenum. The terminal, or intercalated, ducts are lined by flat, squamous-like epithelia. Terminal end duct cells that interface with acini are called centroacinar cells. Intercalated ducts merge to form intralobular ducts (lined by cuboidal epithelia), and these in turn merge to form interlobular ducts, which finally merge to form into the main duct (lined by simple columnar epithelia). The main duct traverses the pancreas to the duodenum, delivering digestive enzyme-laden fluid.

The endocrine and exocrine compartments of the pancreas emerge from a common progenitor population. Pancreatic development involves the interplay of Hedgehog signaling during early stages, Notch signaling, and other cues from the mesenchyme. Moreover, a number of transcription factors have been identified from genetic studies that are critical for pancreatic development: Pdx1 is required for the specification of all pancreatic lineages; Pdx1, Ngn3, NeuroD (also known as BETA2), Pax4, Mafa, Math, Nkx6-1, Nkx2-2, Neurod, Mnx1, Foxa1, Foxa2 and Arx are associated with endocrine lineage commitment; exocrine lineage specification or differentiation is influenced both by the lack of proendocrine transcription factors and by the presence of permissive signals furnished by contiguous pancreatic mesenchyme, including Wnt signaling, laminin-1, and soluble follistatin. Transcription factors associated with acinar cells include, but are not limited to, Ptf1a, Gata4, Mist1 and Nr5a2. Transcription factors associated with ductal cells include, but are not limited to, Hnf6, Hnf1b, Sox9 and Foxa2. Furthermore, the levels of FGF-1, FGF-7, TGF-01, activin and EGFR are important in determining the balance between endocrine and exocrine differentiation.

Acinar cell differentiation during development appears to be regulated by the bHLH (basic helix-loop-helix) transcription factor, Ptf1a (also known as p48). Although detected early in pancreatic development in multipotent progenitor cells, Ptf1a expression becomes restricted to differentiating and mature acinar cells. Knockout of Ptf1a in mice leads to an absence of the exocrine pancreas and displacement of islet cells to the spleen, where the endocrine compartment resides in some lower vertebrates. Mist1 is another bHLH transcription factor that becomes important at the approximate time of secondary transition, and mice lacking Mist1 exhibit defective acinar cellular organization.

Pancreatic Stem Cells (PSCs)

Stem cells are cells that retain the ability to renew their own kind through mitotic cell division and their daughter cells can differentiate into a diverse range of specialized cell types. The two broad types of mammalian stem cells are: embryonic stem (ES) cells that are found in blastocysts, and adult stem cells that are found in adult tissues. In a developing embryo, ESs can differentiate into all of the specialized embryonic tissues. In adult organisms, adult stem cells and progenitor cells act as a repair system for the body, replenishing specialized cells, but also maintaining the normal turnover of regenerative organs, such as blood, skin or intestinal tissues. Pluripotent stem cells can differentiate into cells derived from any of the three germ layers.

In some embodiments, the term "stem cell" as used herein, refers to an undifferentiated cell which is capable of proliferation and giving rise to more progenitor cells having the ability to generate a large number of mother cells that can in turn give rise to differentiated, or differentiable daughter cells known as precursor cells. The daughter cells themselves can be induced to proliferate and produce progeny that subsequently differentiate into one or more mature cell types, while also retaining one or more cells with parental developmental potential.

In some embodiments, the term "stem cell" also refers to a subset of progenitors that have the capacity or potential, under particular circumstances, to differentiate to a more specialized or differentiated phenotype, and also retain the capacity, under certain circumstances, to proliferate without substantially differentiating.

The PSCs described herein are somatic stem cells as opposed to ESs. In a preferred embodiment, the PSCs described are adult stem cells.

In one embodiment, as used herein, the term "c-kit positive pancreatic stem cell" or "c-kit positive PSC" encompasses stem cells, progenitor cells and precursor cells, all of which are c-kit positive.

In one embodiment, as used herein, the term "c-kit positive pancreatic stem cell" or "c-kit positive PSC" encompasses c-kit positive cells that express minimal levels of insulin, C-peptide, glucagon, CK19 and/or amylase.

Cellular differentiation is a complex process typically occurring through many cell divisions. A differentiated cell may derive from a multipotent cell which itself is derived from a multipotent cell, and so on. While each of these multipotent cells may be considered stem cells, the range of cell types each multipotent cell can give rise to may vary considerably. Some differentiated cells also have the capacity to give rise to cells of greater developmental potential. Such capacity may be natural or may be induced artificially upon treatment with various factors. In many biological instances, stem cells are "multipotent" because they can produce progeny of more than one distinct cell type, and it is required as used in this document. Self-renewal is the other classical part of the stem cell definition, and it is essential as used in this document. In theory, self-renewal can occur by either of two major mechanisms. Stem cells may divide asymmetrically, with one daughter retaining the stem state and the other daughter expressing some distinct other specific function and phenotype. Alternatively, some of the stem cells in a population can divide symmetrically into two stem cells, thus maintaining some stem cells in the population as a whole, while other cells in the population give rise to differentiated progeny only.

In one embodiment, the population of isolated cells that is substantially enriched for c-kit positive cells comprises predominantly PSCs. Therefore, in one embodiment, the population of isolated cells that is substantially enriched for c-kit positive cells is referred to as a population of isolated c-kit positive PSCs. It is meant that the population of c-kit positive PSCs can include some c-kit positive progenitor cells and/or c-kit precursor cells.

As used herein, in some embodiments, the term "a population of isolated and substantially enriched for c-kit positive PSCs" or "a population of isolated c-kit positive PSCs" encompasses a heterogeneous or homogeneous population of PSCs and/or pancreatic progenitor cells and/or pancreatic precursor cells. PSCs are multipotent and produce cell types of many lineages. In contrast, pancreatic progenitor cells and pancreatic precursor cells are lineage determinate cells. For example, if a pancreatic progenitor cell is determinate for a beta cell lineage, i.e., will produce beta cells in the future, this pancreatic progenitor cell will not switch and produce acinar cells, which are cells of the exocrine pancreas. In some embodiments, pancreatic progenitor cells and pancreatic precursor cells are determinate for an alpha cell, a beta cell, a delta cell, an epsilon cell, a PP cell, an acinar cell, a centroacinar cell or a ductal cell.

A population of isolated c-kit positive PSCs comprising at least two different cell types is referred to herein as a "heterogeneous population". It is also contemplated herein that pancreatic stem cells or pancreatic progenitor cells are isolated and expanded ex vivo prior to transplantation. A population of isolated c-kit positive PSCs comprising only one cell type (e.g., beta cells) is referred to herein as a "homogeneous population of cells".

In the examples, this population of cells in the human pancreatic tissue expresses c-kit, also called KIT or CD117, which is a cytokine receptor that binds cytokine stem cell factor (SCF). SCF signals to cells to divide and grow. In general, c-kit is expressed on the surface of stem cells as well as the progenitor and precursor cell types which are progeny from the stem cells by mitotic division. Therefore, c-kit is a stem cell marker. By immunostaining for c-kit in human pancreatic tissues, the inventors found such c-kit positive cells (FIG. 2A-FIG. 2F, FIG. 3A-FIG. 3C). Prior to this discovery, there has been no reported evidence of the presence of stem cells in the adult pancreas. These c-kit positive cells are mainly undifferentiated and express minimal levels of insulin, C-peptide, glucagon, CK19 and/or amylase.

The inventors showed that these c-kit positive PSCs have clonogenic properties. When these cells were isolated and plated at very low cell density, i.e., plated single cell in vitro, multicellular clones grew out of these single cells (FIG. 5), thus demonstrating the clonogenic properties of stem cells.

Figures 6A, 6B, 6C, 6D, 6E, 6F:
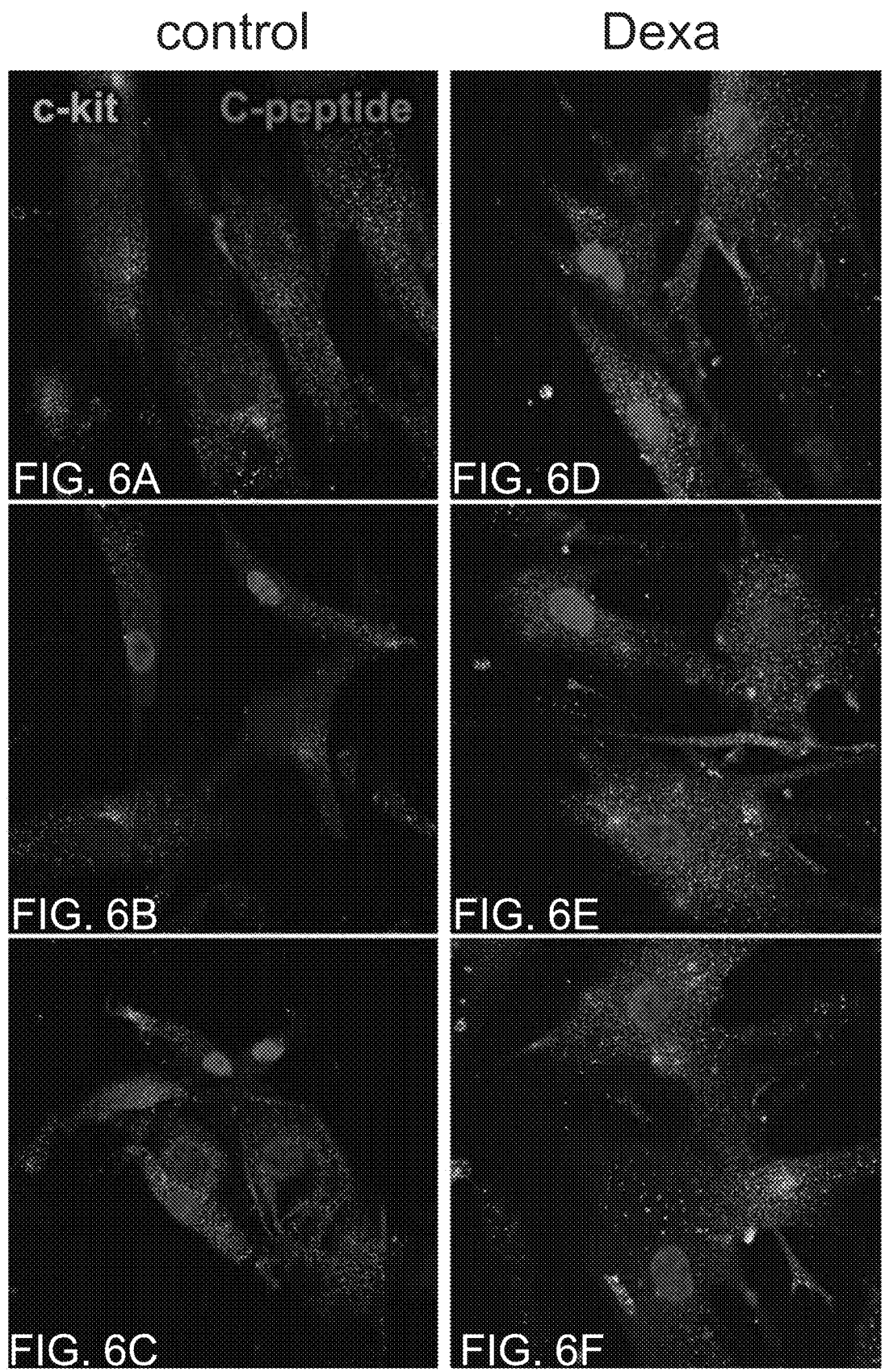
FIG. 6A-FIG. 6R show representative IHC images of undifferentiated ('control', FIG. 6A-FIG. 6C, FIG. 6G-FIG. 6I, FIG. 6M-FIG. 6O) or differentiated ('Dexa', FIG. 6D-FIG. 6F, FIG. 6J-FIG. 6L, FIG. 6P-FIG. 6R) c-kit positive cells stained for c-kit (green, FIG. 6A-FIG. 6R), C-peptide (red, FIG. 6A-FIG. 6F), glucagon (red, FIG. 6G-FIG. 6L) and amylase (red, FIG. 6M-FIG. 6R).
Figures 6G, 6H, 6I, 6J, 6K, 6L:
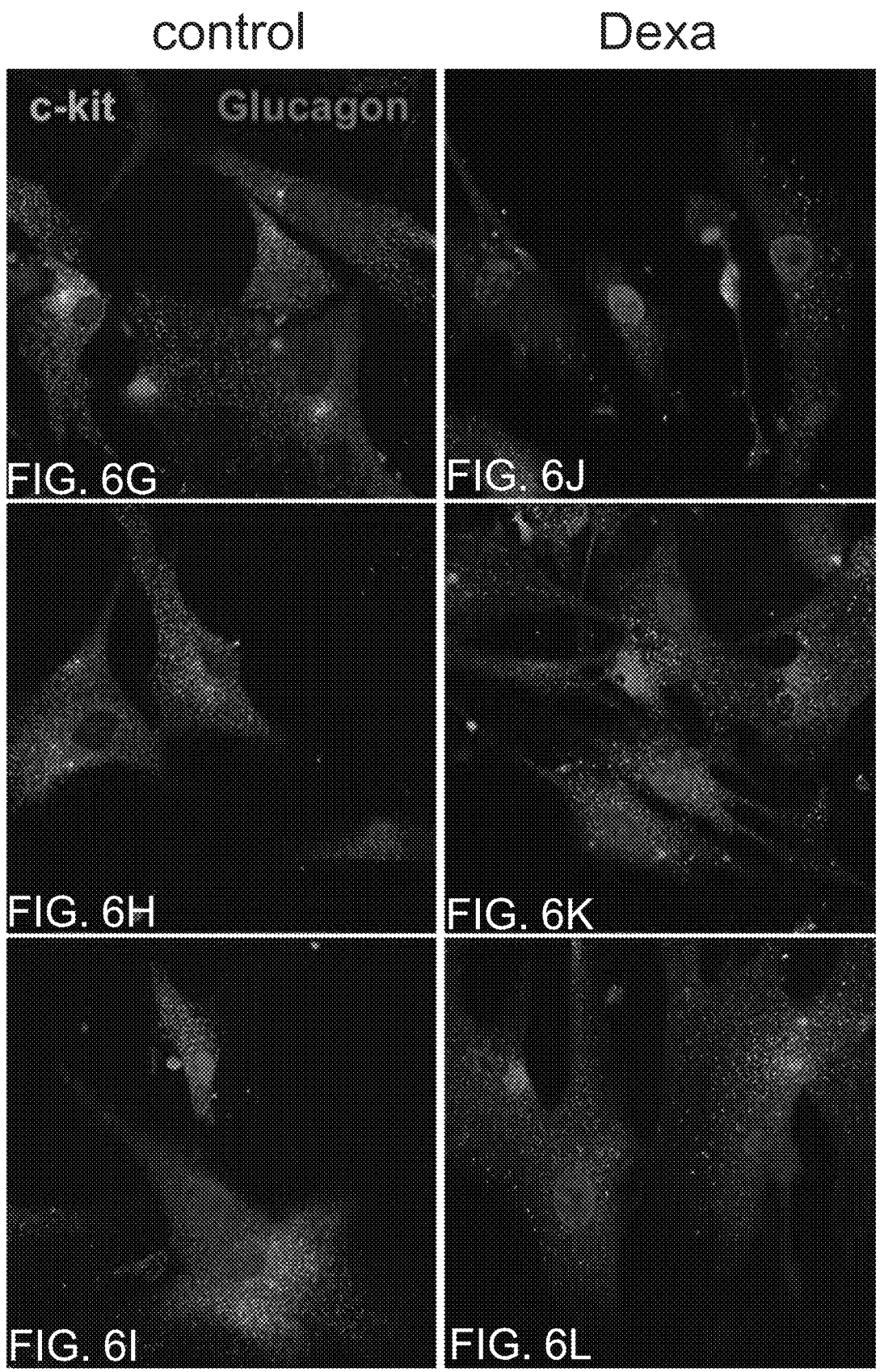
FIG. 6S shows that hPSCs grown in a medium containing glucose synthesize human insulin as measured by the high sensitive ELISA assay. GSIS: glucose-stimulated insulin secretion.

Moreover, the multicellular clones arising from the initially isolated c-kit positive PSCs are multipotent in terms of the cell fate of the daughter cells of the colonies. The inventors showed that clonal c-kit positive cells exposed to a differentiation medium acquired markers of endocrine and exocrine lineages (FIG. 6A-FIG. 6R).

Figure 4:
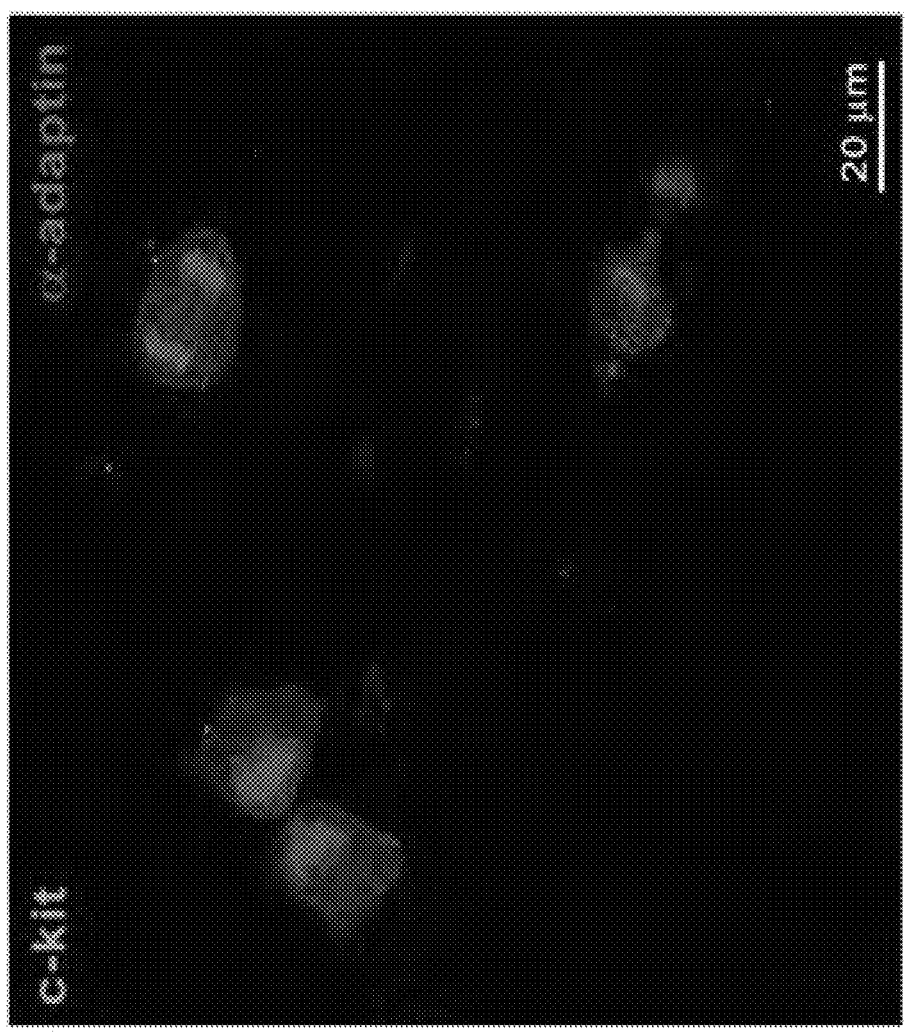
FIG. 4 shows representative IHC images of c-kit-positive cells stained for c-kit (green) and the cell fate determinant α-adaptin (red). Cell nuclei were stained with DAPI.

Finally, these c-kit positive PSCs can self-renew. The inventors showed that the c-kit positive PSCs divide asymmetrically giving rise to a daughter stem cell and a daughter committed cell. Additionally, c-kit positive cells can divide symmetrically. The modality of division was defined on the basis of the non-uniform or uniform distribution of the cell fate determinant α-adaptin (FIG. 4).

In one embodiment of all aspects of the compositions and methods described, the population of isolated c-kit positive PSCs contains cells that have long-term and short-term regeneration capacities, and committed multipotent, oligopotent, and unipotent progenitors.

Accordingly, as used herein, the term "PSC" refers to a cell with multi-lineage pancreatic differentiation potential and sustained self-renewal activity. "Self renewal" refers to the ability of a cell to divide and generate at least one daughter cell with the identical (e.g., self-renewing) characteristics of the parent cell. The second daughter cell may commit to a particular differentiation pathway. For example, a self-renewing PSC divides and forms one daughter stem cell and another daughter cell committed to differentiation into exocrine and/or endocrine cells of the pancreas. A committed progenitor cell has typically lost the self-renewal capacity, and upon cell division produces two daughter cells that display a more differentiated (i.e., restricted) phenotype.

"PCSs," as used in the methods described herein, therefore, encompasses all pluripotent cells capable of differentiating into several cell types of the pancreas, including, but not limited to, an alpha cell, a beta cell, a delta cell, an epsilon cell, a PP cell, an acinar cell, a centroacinar cell, or a ductal cell.

"Pancreatic progenitor cells," as the term is used herein, refer to the subset of PSC that are committed to a particular pancreatic cell lineage and generally do not self-renew, and can be identified, for example by cell surface markers or intracellular proteins. For example, insulin or C-peptide which indicates commitment to the beta cell lineage; or glucagon which indicates commitment to the alpha cell lineage. In some embodiments of all aspects of the compositions and methods described, PSCs are selected for using one or more of these additional cell surface markers.

The presence of PSC can be determined by any method known in the art, or phenotypically through the detection of cell surface markers using assays known to those of skill in the art or those described in the examples.

Isolation of PSCs

In some embodiments of all aspects of the compositions and methods described, the PSCs are derived or isolated from pancreatic tissue samples of the following sources: freshly deceased subjects, tissue biopsy from a live subject, or a pancreatic stem cell line. In some embodiments of all aspects of the compositions and methods described, the PSCs are derived ex vivo from other cells, such as induced pluripotent stem cells (iPS cells) or adult pluripotent cells.

In one embodiment of all aspects of the compositions and methods described, the PSC can be isolated using any method known to one of skill in the art or according to the method described herein, for example, fine needle aspiration for a small pancreatic tissue sample from a live subject.

PSC can be isolated from pancreatic tissue samples by any method known in the art. Methods of dissociating individual cells from a tissue sample are known in the art, e.g., in U.S. Pat. No. 7,547,674 and U.S. Patent Application U.S. 2006/0239983, 2009/0148421, and 2009/0180998. These references are herein incorporated by reference in their entirety.

In one embodiment of all aspects of the compositions and methods described, the population of isolated PSCs is isolated by the following method. One skilled in the art would be able to make minor adjustments to the method as needed for pancreatic tissues from different sources. A small piece of pancreatic tissue, a minimum size of at least 1 cubic cm, is enzymatically digested with collagenase to obtain single cells. Small intact cells are resuspended and aggregates of cells are removed with a cell strainer. This cell strainer step is optional. Then the cells are incubated with a mouse c-kit antibody. c-kit positive cells are isolated and collected with immunomagnetic beads coated with anti-mouse IgG.

In one embodiment of all aspects of the compositions and methods described, the isolated c-kit positive cells obtained are then cultured by the following method. One skilled in the art would be able to make minor adjustments to the method as needed. The culture method is used to grow and expand the number of c-kit positive PSCs. The isolated c-kit positive cells are plated in modified F12K medium containing F12 medium (GIBCO®, Grand Island, N.Y.) supplemented with 5-10% FBS (GIBCO®) and insulin-selenium-transferrin mixture (SIGMA, St. Louis, Mo.) under standard tissue culture conditions. After reaching confluence, the cells are passaged to several other plates to expand the culture using standard tissue culture protocol of handling the cells.

In some embodiments of all aspects of the compositions and methods described, the PSC from the pancreatic tissues described herein is expanded ex vivo using any method acceptable to those skilled in the art prior to use in the methods described herein. In some embodiments of all aspects of the compositions and methods described, the expanded c-kit positive PSCs are further sorted, fractionated, treated to remove any undesired cells, or otherwise manipulated to treat the patient using any procedure acceptable to those skilled in the art of preparing cells for transplantation. Example of an undesired cell is a malignant cell.

There is typically a very small number of PSCs in a sample of pancreatic tissue, for example, there can be only one or two c-kit positive cell per 40,000 cells. Therefore, expansion of the selected c-kit positive PSCs is often necessary to increase the number of cells required for the therapeutic uses described herein. The greater number of PSCs transplanted in the therapeutic uses described herein increases the success rate of the therapy used therein. The PSCs are used to repair, reconstitute and generate some of the damaged tissues and cells in the subject's pancreas. Therefore, more PSCs transplanted means more cells available to repair, reconstitute and generate new pancreatic cells and pancreatic tissue. In some embodiments, a success of the transplant therapy can be measured by any method known in the art and those described herein, such as an improvement in the subject's blood glucose level and general health conditions which are known to a physician skilled in the art.

In some embodiments of all aspects of the compositions and methods described, a pancreatic tissue sample comprising PSCs is isolated from a subject and is then further processed, for example, by cell sorting (e.g., FACS), to obtain a population of substantially enriched c-kit positive PSCs. In other embodiments of all aspects of the compositions and methods described, a population of substantially enriched c-kit positive PSCs refers to an in vitro or ex vivo culture of expanded PSCs.

In some embodiments of all aspects of the compositions and methods described, the pancreatic tissue samples from the various sources are frozen samples, such as frozen or cryopreserved prior to extraction or selection of the c-kit positive PSCs. The pancreatic tissue sample is obtained from a subject or other sources described herein and then cryopreserved with cryoprotectant. In another embodiment of all aspects of the compositions and methods described, the population of isolated c-kit PSCs from the pancreatic tissue sample is cryopreserved with cryoprotectant prior to use. In yet another embodiment of all aspects of the compositions and methods described, the population of isolated c-kit PSCs that has been expanded in vitro culture is cryopreserved with cryoprotectant prior to use. Methods of cryopreservation of tissues and cells with cryoprotectant are well known in the art. Further methods for thawing the cryopreserved tissue or cells for use are also well known in the art.

The terms "isolate" and "methods of obtaining or preparing," as used herein, refer to a process whereby a cell or a population of cells, such as a population of PSCs, is removed from a subject or from a pancreatic tissue sample in which it was originally found. The term "isolated population," as used herein, refers to a population of cells that has been removed and separated from a biological sample, or a mixed or heterogeneous population of cells found in such a sample. Such a mixed population includes, for example, a population of PSCs obtained from a pancreatic tissue sample. In some embodiments, an isolated population is a substantially pure population of cells as compared to the heterogeneous population from which the cells were isolated or enriched from. In some embodiments, the isolated population is a population of isolated c-kit positive PSCs. In other embodiments of this aspect and all aspects described herein, the isolated population comprises a substantially enriched population of c-kit positive PSCs. In some embodiments, an isolated cell or cell population, such as a population of c-kit positive PSCs, is further cultured in vitro or ex vivo, e.g., in the presence of growth factors or cytokines, to further expand the number of cells in the isolated cell population or substantially c-kit enriched cell population. In one embodiment, the population of c-kit positive PSCs is further cultured in vitro or ex vivo with SCF, IGF-1 and/or HGF. Such culture can be performed using any method known to one of skill in the art. In some embodiments, the isolated or substantially enriched c-kit positive PSC populations obtained by the methods disclosed herein are later administered to a second subject, or re-introduced into the subject from which the cell population was originally isolated (e.g., allogeneic transplantation vs. autologous administration).

The term "substantially enriched," with respect to a particular cell population, refers to a population of cells that is at least about 50%, 75%, at least about 80%, at least about 85%, at least about 90%, at least about 95%, at least about 98%, or at least about 99% pure, with respect to the cells making up a total cell population. In other words, the terms "substantially enriched" or "essentially purified", with regard to a population of c-kit positive PSCs isolated for use in the methods disclosed herein, refers to a population of c-kit positive PSCs that contain fewer than about 30%, 25%, fewer than about 20%, fewer than about 15%, fewer than about 10%, fewer than about 9%, fewer than about 8%, fewer than about 7%, fewer than about 6%, fewer than about 5%, fewer than about 4%, fewer than about 3%, fewer than about 2%, fewer than about 1%, or less than 1%, of cells that are not PSC, as defined by the terms herein. Some embodiments of these aspects further encompass methods to expand a population of substantially pure or enriched PSCs, wherein the expanded population of c-kit positive PSCs is also a substantially pure or enriched population of c-kit positive PSCs.

The term "substantially negative," with respect to a particular marker presence in a cell population, refers to a population of cells that is not more than about 10%, not more than about 8%, not more than about 6%, not more than about 4%, not more than about 2%, not more than about 1% positive for that marker, with respect to the cells making up a total cell population.

The terms "enriching" or "enriched" are used interchangeably herein and mean that the yield (fraction) of cells of one type, such as PSCs for use in the methods described herein, is increased by at least 15%, by at least 20%, by at least 25%, by at least 30%, by at least 35%, by at least 40%, by at least 45%, by at least 50%, by at least 55%, by at least 60%, by at least 65%, by at least 70%, or by at least 75%, over the fraction of cells of that type in the starting biological sample, culture, or preparation. A population of c-kit positive PSCs obtained for use in the methods described herein is most preferably at least 50% enriched for c-kit positive PSCs.

In some embodiments, markers specific for PSCs are used to isolate or enrich for these cells. A "marker," as used herein, describes the characteristics and/or phenotype of a cell. Markers can be used for selection of cells comprising characteristics of interest. Markers will vary with specific cells. Markers are characteristics, whether morphological, functional or biochemical (enzymatic), particular to a cell type, or molecules expressed by the cell type. Preferably, such markers are proteins, and more preferably, possess an epitope for antibodies or other binding molecules available in the art. However, a marker may consist of any molecule found in a cell including, but not limited to, proteins (peptides and polypeptides), lipids, polysaccharides, nucleic acids and steroids. Examples of morphological characteristics or traits include, but are not limited to, shape, size, appearance (e.g., smooth, translucent), and nuclear to cytoplasmic ratio. Examples of functional characteristics or traits include, but are not limited to, the ability to adhere to particular substrates, ability to incorporate or exclude particular dyes, ability to migrate under particular conditions, and the ability to differentiate along particular lineages. Markers may be detected by any method available to one of skill in the art.

Accordingly, as used herein, a "cell-surface marker" refers to any molecule that is expressed on the surface of a cell. Cell-surface expression usually requires that a molecule possesses a transmembrane domain. Some molecules that are normally not found on the cell-surface can be engineered by recombinant techniques to be expressed on the surface of a cell. Many naturally occurring cell-surface markers are termed "CD" or "cluster of differentiation" molecules. Cell-surface markers often provide antigenic determinants to which antibodies can bind to. A cell-surface marker of particular relevance to the methods described herein is CD117 or c-kit. The useful PSCs according to the compositions and method preferably express c-kit or in other words, they are c-kit positive.

A cell can be designated "positive" or "negative" for any cell-surface marker or other intracellular marker, and both such designations are useful for the practice of the methods described herein. A cell is considered "positive" for a cell-surface marker if it expresses the marker on its cell-surface or intracellularly in amounts sufficient to be detected using methods known to those of skill in the art, such as contacting a cell with an antibody that binds specifically to that marker, and subsequently performing flow cytometric analysis of such a contacted cell to determine whether the antibody is bound to the cell. It is to be understood that while a cell can express messenger RNA for a cell-surface marker, in order to be considered positive for the methods described herein, the cell must express the marker on its surface. Similarly, a cell is considered "negative" for a cell-surface marker or other intracellular marker if it does not express the marker in amounts sufficient to be detected using methods known to those of skill in the art, such as contacting a cell with an antibody that binds specifically to that marker and subsequently performing flow cytometric analysis of such a contacted cell to determine whether the antibody is bound to the cell.

In some embodiments of all aspects of the compositions and methods described, the c-kit positive PSCs are negatively selected and the selection uses an agent specific for a cell surface marker. In some embodiments of all aspects of the compositions and methods described, the cell surface marker is a lineage specific marker such as exocrine cell lineage or an endocrine cell lineage.

In some embodiments of all aspects of the compositions and methods described, in the context of negative selection, where agents specific for lineage markers are used, all of the agents can comprise the same label or tag, such as a fluorescent tag, and thus all cells positive for that label or tag can be excluded or removed, leaving the lineage marker-negative PSCs, pancreatic progenitor cells and/or pancreatic precursor cells for use in the methods described herein. This is negative selection, selecting for those cells that did not contact with the agents specific for lineage markers.

Accordingly, as defined herein, an "agent specific for a cell-surface marker or other intracellular marker" refers to an agent that can selectively react with or bind to that cell-surface marker or other intracellular marker, but has little or no detectable reactivity to another cell-surface marker, other intracellular marker or antigen. For example, an agent specific for c-kit will not identify or bind to CD49e. Thus, agents specific for cell-surface markers or other intracellular marker recognize unique structural features of the markers. In some embodiments, an agent specific for a marker binds to the marker, but does not cause initiation of downstream signaling events mediated by that marker, for example, a non-activating antibody. Agents specific for cell-surface molecules include, but are not limited to, antibodies or antigen-binding fragments thereof, natural or recombinant ligands, small molecules, nucleic acid sequence and nucleic acid analogues, intrabodies, aptamers, and other proteins or peptides.

In some embodiments of all aspects of the compositions and methods described, the preferred agents specific for cell-surface markers used for isolating PSCs are antibody agents that specifically bind the cell-surface markers, and can include polyclonal and monoclonal antibodies, and antigen-binding derivatives or fragments thereof. Well-known antigen binding fragments include, for example, single domain antibodies (dAbs; which consist essentially of single VL or VH antibody domains), Fv fragment, including single chain Fv fragment (scFv), Fab fragment, and F(ab')2 fragment. Methods for the construction of such antibody molecules are well known in the art. Accordingly, as used herein, the term "antibody" refers to an intact immunoglobulin or to a monoclonal or polyclonal antigen-binding fragment with the Fc (crystallizable fragment) region or FcRn binding fragment of the Fc region. Antigen-binding fragments may be produced by recombinant DNA techniques or by enzymatic or chemical cleavage of intact antibodies. "Antigen-binding fragments" include, inter alia, Fab, Fab', F(ab')2, Fv, dAb, and complementarity determining region (CDR) fragments, single-chain antibodies (scFv), single domain antibodies, chimeric antibodies, diabodies and polypeptides that contain at least a portion of an immunoglobulin that is sufficient to confer specific antigen binding to the polypeptide. The terms Fab, Fc, pFc', F(ab')2 and Fv are employed with standard immunological meanings known to those skilled in the art, e.g., in Klein, "Immunology" (John Wiley, New York, N.Y., 1982); Clark, W. R. (1986); in "The Experimental Foundations of Modern Immunology" (Wiley & Sons, Inc., New York); and Roitt, I. (1991) "Essential Immunology", 7th Ed., (Blackwell Scientific Publications, Oxford). Such antibodies or antigen-binding fragments are available commercially from vendors such as R&D Systems®, BD Biosciences, e-Biosciences and Miltenyi®, or can be raised against these cell-surface markers or other intracellular marker by methods known to those skilled in the art.

In some embodiments of all aspects of the compositions and methods described, an agent specific for a cell-surface molecule or other intracellular marker, such as an antibody or antigen-binding fragment, is labeled with a tag to facilitate the isolation of the pancreatic stem cells. The terms "label" or "tag", as used herein, refer to a composition capable of producing a detectable signal indicative of the presence of a target, such as, the presence of a specific cell-surface marker in a biological sample. Suitable labels include fluorescent molecules, radioisotopes, nucleotide chromophores, enzymes, substrates, chemiluminescent moieties, magnetic particles, bioluminescent moieties, and the like. As such, a label is any composition detectable by spectroscopic, photochemical, biochemical, immunochemical, electrical, optical or chemical means needed for the methods to isolate and enrich for PSCs, pancreatic progenitor cell and pancreatic precursor cells.

The terms "labeled antibody" or "tagged antibody", as used herein, includes antibodies that are labeled by detectable means and include, but are not limited to, antibodies that are fluorescently, enzymatically, radioactively, and chemiluminescently labeled. Antibodies can also be labeled with a detectable tag, such as c-Myc, HA, VSV-G, HSV, FLAG, V5, or HIS, which can be detected using an antibody specific to the tag, for example, an anti-c-Myc antibody. Various methods of labeling polypeptides and glycoproteins are known in the art and may be used. Non-limiting examples of fluorescent labels or tags for labeling the antibodies for use in the methods of invention include hydroxycoumarin, succinimidyl ester, aminocoumarin, succinimidyl ester, methoxycoumarin, Cascade Blue, Hydrazide, Pacific Blue, maleimide, Pacific Orange, lucifer yellow, NBD, NBD-X, R-phycoerythrin (PE), a PE-Cy5 conjugate (Cychrome, R670, Tri-Color, Quantum Red), a PE-Cy7 conjugate, Red 613, PE-Texas Red, PerCP, Peridinin chlorphyll protein, TruRed (PerCP-Cy5.5 conjugate), FluorX, Fluoresceinisothyocyanate (FITC), BODIPY-FL, TRITC, X-Rhodamine (XRITC), Lissamine Rhodamine B, Texas Red, Allophycocyanin (APC), an APC-Cy7 conjugate, ALEXA FLUOR® 350, ALEXA FLUOR® 405, ALEXA FLUOR® 430, ALEXA FLUOR® 488, ALEXA FLUOR® 500, ALEXA FLUOR® 514, ALEXA FLUOR® 532, ALEXA FLUOR® 546, ALEXA FLUOR® 555, ALEXA FLUOR® 568, ALEXA FLUOR® 594, ALEXA FLUOR® 610, ALEXA FLUOR® 633, ALEXA FLUOR® 647, ALEXA FLUOR® 660, ALEXA FLUOR® 680, ALEXA FLUOR® 700, ALEXA FLUOR® 750, ALEXA FLUOR® 790, Cyt2, Cy3, Cy3B, Cy3.5, Cy5, Cy5.5 or Cy7.

In some embodiments of all aspects of the compositions and methods described, a variety of methods to isolate a substantially pure or enriched population of c-kit positive PSCs are available to a skilled artisan, including immunoselection techniques, such as high-throughput cell sorting using flow cytometric methods, affinity methods with antibodies labeled to magnetic beads, biodegradable beads, non-biodegradable beads, and antibodies panned to surfaces including dishes and combination of such methods.

In some embodiments of all aspects of the compositions and methods described, the isolation and enrichment for populations of PSCs can be performed using bead based sorting mechanisms, such as magnetic beads. In such methods, a digested pancreatic tissue sample is contacted with magnetic beads coated with antibodies against one or more specific cell-surface antigens, such as c-kit. This causes the cells in the sample that express the respective antigen to attach to the magnetic beads. After a period of time to allow the c-kit positive cells to bind the beads, the mixture of cell and beads are exposed to a strong magnetic field, such as a column or rack having a magnet. The cells attached to the beads (expressing the cell-surface marker) stay on the column or sample tube, while other cells (not expressing the cell-surface marker) flow through or remain in solution. Using this method, cells can be separated positively or negatively, or using a combination therein, with respect to the particular cell-surface markers.

In some embodiments of all aspects of the compositions and methods described, magnetic activated cell sorting (MACS) strategies are used for isolation and pre-selection of PSCs. In some embodiments, PSCs are isolated in the presence of human plasma or human serum albumin (HSA), such as 2% HSA.

In some preferred embodiments of all aspects of the compositions and methods described, PSCs are isolated or enriched using positive selection for the cell-surface marker c-kit.

As defined herein, "positive selection" refers to techniques that result in the isolation or enrichment of cells expressing specific cell-surface markers or intracellular proteins, while "negative selection" refers to techniques that result in the isolation or enrichment of cells that do not express specific cell-surface markers or intracellular proteins. Negative selection can be performed by any method known in the art. For example, typical negative selection is carried out by removing the cells that do express the marker of interest.

In some embodiments of all aspects of the compositions and methods described, beads can be coated with antibodies by a skilled artisan using standard techniques known in the art, such as commercial bead conjugation kits. In some embodiments, a negative selection step is performed to remove cells expressing one or more lineage markers, followed by fluorescence activated cell sorting to positively select PSCs expressing one or more specific cell-surface markers.

A number of different cell-surface markers have specific expression on specific differentiated cell lineages, and are not expressed by the c-kit positive PSCs isolated for the methods described herein. Accordingly, when agents specific for these lineage cell-markers are contacted with c-kit positive PSCs, the cells will be "negative."

In some embodiments of all aspects of the compositions and methods described, flow cytometric methods, alone or in combination with magnetic bead based methods, are used to isolate or enrich for c-kit positive PSCs. As defined herein, "flow cytometry" refers to a technique for counting and examining microscopic particles, such as cells and DNA, by suspending them in a stream of fluid and passing them through an electronic detection apparatus. Flow cytometry allows simultaneous multiparametric analysis of the physical and/or chemical parameters of up to thousands of particles per second, such as fluorescent parameters. Modern flow cytometric instruments usually have multiple lasers and fluorescence detectors. Increasing the number of lasers and detectors allows for labeling by multiple antibodies, and can more precisely identify a target population by their phenotypic markers. Certain flow cytometric instruments can take digital images of individual cells, allowing for the analysis of fluorescent signal location within or on the surface of cells.

A common variation of flow cytometric techniques is to physically sort particles based on their properties, so as to purify populations of interest, using "fluorescence-activated cell sorting" As defined herein, "fluorescence-activated cell sorting" or "flow cytometric based sorting" methods refer to flow cytometric methods for sorting a heterogeneous mixture of cells from a single biological sample into one or more containers, one cell at a time, based upon the specific light scattering and fluorescent characteristics of each cell and provides fast, objective and quantitative recording of fluorescent signals from individual cells as well as physical separation of cells of particular interest. Accordingly, in those embodiments when the agents specific for cell-surface markers are antibodies labeled with tags that can be detected by a flow cytometer, fluorescence-activated cell sorting (FACS) can be used in and with the methods described herein to isolate and enrich for populations of PSCs.

Expansion of PSCs

In some embodiments of all aspects of the compositions and methods described, the population of isolated and substantially enriched c-kit positive PSCs are further expanded to increase in numbers prior to their use in the therapeutic methods described herein.

In some embodiments of all aspects of the compositions and methods described, c-kit positive PSCs isolated or enriched by using the methods and techniques described herein are expanded in culture, i.e., the cell numbers are increased outside the body of the subject, using methods known to one of skill in the art, prior to administration to a subject in need.

In one embodiment of all aspects of the compositions and methods described, the isolated c-kit positive PSCs obtained are expanded in culture according to the following method. One skilled in the art would be able to make minor adjustment to the method as needed. The isolated c-kit positive cells are plated in modified F12K medium containing F12 medium (GIBCO®, Grand Island, N.Y.) supplemented with 5-10% FBS (GIBCO®) and insulin-selenium-transferrin mixture (SIGMA, St. Louis, Mo.) under standard tissue culture conditions, e.g., 95% air, 5% $CO_2$, 37° C. After reaching confluence, the cells from one confluent plate are passaged to several other plates to expand the culture using standard tissue culture protocol of handling the cells.

In some embodiments of all aspects of the compositions and methods described, such expansion methods can comprise, for example, culturing the c-kit positive PSCs in serum-free medium supplemented with cytokines and/or growth factors under conditions that cause expansion of PSCs, such as stem cell factor, IGF-1, and/or HGF. HGF positively influences cell migration through the expression and activation of matrix metalloproteinase-2. This enzyme family destroys barriers in the extracellular matrix thereby facilitating stem cell movement, homing and tissue restoration. Similarly, insulin-like growth factor-1 (IGF-1) is mitogenic, anti-apoptotic and is necessary for neural stem cell multiplication and differentiation. In a comparable manner, IGF-1 impacts stem cells by increasing their number and protecting their viability. In some embodiments of all aspects of the compositions and methods described, the c-kit positive PSCs can further be cultured with factors and/or under conditions aimed at inducing differentiation of the PSCs to exocrine and/or endocrine cells, such as using serum-free medium supplemented with dexamethasone and/or a combination of growth factors and cytokines.

In other embodiments of all aspects of the compositions and methods described, c-kit positive PSCs are expanded by adapting not more than about 0.5%, nanotechnological or nanoengineering methods, as reviewed in Lu J et al., "A Novel Technology for Hematopoietic Stem Cell Expansion using Combination of Nanofiber and Growth Factors." Recent Pat Nanotechnol. 2010 4(2):125-35. For example, in some embodiments, nanoengineering of stem cell microenvironments can be performed. As used herein, secreted factors, stem cell—neighboring cell interactions, extracellular matrix (ECM) and mechanical properties collectively make up the "stem cell microenvironment". Stem cell microenvironment nanoengineering can comprise the use of micro/nanopatterned surfaces, nanoparticles to control release growth factors and biochemicals, nanofibers to mimic extracellular matrix (ECM), nanoliter-scale synthesis of arrayed biomaterials, self-assembly peptide system to mimic signal clusters of stem cells, nanowires, laser fabricated nanogrooves, and nanophase thin films to expand PSCs.

In other embodiments of all aspects of the compositions and methods described, the c-kit positive PSCs are genetically manipulated, e.g., transfected with an exogenous nucleic acid. Nanoengineering can be used for the transfection and genetic manipulation in PSCs, such as nanoparticles for in vivo gene delivery, nanoneedles for gene delivery to PSCs, self-assembly peptide system for PSC transfection, nanowires for gene delivery to PSCs, and micro/nanofluidic devices for PSC electroporation.

In other embodiments of all aspects of the compositions and methods described, the c-kit positive PSCs isolated or enriched for use in the methods can be expanded using bioreactors.

The terms "increased," "increase" or "expand", when used in the context of PSC expansion, generally mean an increase in the number of PSCs by a statistically significant amount; for the avoidance of any doubt, the terms "increased," "increase," "expand" or "expanded," mean an increase, as compared to a reference level, of at least about 10%, of at least about 15%, of at least about 20%, of at least about 25%, of at least about 30%, of at least about 35%, of at least about 40%, of at least about 45%, of at least about 50%, of at least about 55%, of at least about 60%, of at least about 65%, of at least about 70%, of at least about 75%, of at least about 80%, of at least about 85%, of at least about 90%, of at least about 95%, or up to and including a 100%, or at least about a 2-fold, or at least about a 3-fold, or at least about a 4-fold, or at least about a 5-fold, at least about a 6-fold, or at least about a 7-fold, or at least about a 8-fold, at least about a 9-fold, or at least about a 10-fold increase, or any increase of 10-fold or greater, as compared to a control or reference level. A control/reference sample or level is used herein to describe a population of cells obtained from the same biological source that has, for example, not been expanded using the methods described herein, e.g., at the start of the expansion culture or the initial number of cells added to the expansion culture.

Storage of Pancreatic Tissue Samples and/or Pancreatic Stem Cells

In some embodiments of all aspects of the compositions and methods described, the pancreatic tissue samples are stored prior to use, i.e., prior to the extraction, isolation or selection of the c-kit positive PSCs therein. In some embodiments of all aspects of the compositions and methods described, the digested pancreatic tissue sample is stored prior to extraction or selection of the c-kit positive PSCs therein. In some embodiments of all aspects of the compositions and methods described, the isolated c-kit positive PSCs are stored. In other embodiments of all aspects of the compositions and methods described, the c-kit positive PSCs are first isolated and/or expanded prior to storage. In one embodiment, the storage is by cryopreservation. The PSCs are thawed when needed for the therapeutic methods described herein.

In some embodiments of all aspects of the compositions and methods described, the pancreatic tissue samples or isolated c-kit positive PSCs (expanded or otherwise) are frozen prior to their use in the methods described herein. Freezing the samples can be performed in the presence of one or more different cryoprotectants for minimizing cell damage during the freeze-thaw process. For example, dimethyl sulfoxide (DMSO), trehalose, or sucrose can be used.

Administration and Uses of PSCs in Regenerative Medicine

Certain embodiments described herein are based on the discovery of somatic stem cells in human pancreatic tissue. In some cases, these human pancreatic stem cells (hPSCs) can repair damaged pancreatic tissues in diabetic mice. Examples of mouse models of diabetes and methods of implanting stem cells in such mice are described in e.g., Hua et al., PLoS One, 2014 Jul. 10; 9(7):e102198. When hPSCs are placed into a mouse with a damaged pancreas, long-term engraftment of the administered hPSCs can occur, and these hPSCs can differentiate into beta cells, for example, which can lead to subsequent beta cell regeneration and repair. This experiment can indicate whether isolated c-kit positive PSCs can be used for pancreatic tissue regeneration and treatment of diabetes in, e.g, human patients. PSCs can also be tested for ability to generate glucose-responsive insulin-secreting cells in mice and protect mice against streptozotocin-induced diabetes as described in Kroon et al., Nature Biotechnology, 2008, April; 26(4):443-52. Accordingly, provided herein are methods for the treatment and/or prevention of a pancreatic disease or disorder in a subject in need thereof. As used herein, the term "pancreatic disease or disorder", "pancreatic disease", "pancreatic condition" and "pancreatic disorder" are used interchangeably. Some of these methods involve administering to a subject a therapeutically effective amount of isolated c-kit positive PSCs by injection, by a catheter system, or a combination thereof. In some aspects of these methods, a therapeutically effective amount of isolated c-kit positive PSCs is administered through vessels, pancreatic duct, directly to the tissue, or a combination thereof. In other aspects, a therapeutically effective amount of isolated c-kit positive PSCs is implanted in a patient in an encapsulating device (see, e.g., U.S. Pat. Nos. 9,132,226 and 8,425,928, the contents of each of which are incorporated herein by reference in their entirety). These methods are particularly aimed at therapeutic and prophylactic treatments of human subjects having or at risk for a pancreatic disease or disorder, e.g., a subject having pancreatitis or diabetes. The isolated or enriched c-kit positive PSCs described herein can be administered to a selected subject having any pancreatic disease or disorder or is predisposed to developing a pancreatic disease or disorder, the administration can be by any appropriate route which results in an effective treatment in the subject. In some embodiments of all aspects of the therapeutic methods described herein, a subject having a pancreatic disease or disorder is first selected prior to administration of the cells.

The terms "subject", "patient" and "individual" are used interchangeably herein, and refer to an animal, for example, a human from whom cells for use in the methods described herein can be obtained (i.e., donor subject) and/or to whom treatment, including prophylactic treatment, with the cells as described herein, is provided, i.e., recipient subject. For treatment of those conditions or disease states that are specific for a specific animal such as a human subject, the term subject refers to that specific animal. The "non-human animals" and "non-human mammals" as used interchangeably herein, includes mammals such as rats, mice, rabbits, sheep, cats, dogs, cows, pigs, and non-human primates. The term "subject" also encompasses any vertebrate including but not limited to mammals, reptiles, amphibians and fish.

However, advantageously, the subject is a mammal such as a human, or other mammals such as a domesticated mammal, e.g., dog, cat, horse, and the like, or food production mammal, e.g., cow, sheep, pig, and the like.

Accordingly, in some embodiments of the therapeutic methods described herein, a subject is a recipient subject, i.e., a subject to whom the isolated c-kit positive PSCs are being administered, or a donor subject, i.e., a subject from whom a pancreatic tissue sample comprising c-kit positive PSCs are being obtained. A recipient or donor subject can be of any age. In some embodiments, the subject is a "young subject," defined herein as a subject less than 10 years of age. In other embodiments, the subject is an "infant subject," defined herein as a subject is less than 2 years of age. In some embodiments, the subject is a "newborn subject," defined herein as a subject less than 28 days of age. In one embodiment, the subject is a human adult.

In some embodiments of the therapeutic methods described herein, the isolated c-kit positive PSC population being administered comprises allogeneic PSCs obtained from one or more donors. As used herein, "allogeneic" refers to PSCs or pancreatic tissue samples comprising PSCs obtained from one or more different donors of the same species, where the genes at one or more loci are not identical. For example, an isolated c-kit positive PSC population being administered to a subject can be obtained from the pancreatic tissue obtained from one more unrelated donor subjects, or from one or more non-identical siblings or other sources. In some embodiments, syngeneic isolated c-kit positive PSC populations is used, such as those obtained from genetically identical animals, or from identical twins. In other embodiments of this aspect, the isolated c-kit positive PSCs are autologous PSCs. As used herein, "autologous" refers to PSCs or pancreatic tissue samples comprising c-kit positive PSCs obtained or isolated from a subject and being administered to the same subject, i.e., the donor and recipient are the same.

Pancreatic disease or disorder is any disease or disorder that occurs in the pancreas or that causes the pancreas to not work properly. Pancreatic diseases or disorders can include, but are not limited to, type 1 diabetes, type 2 diabetes, pancreatitis, cystic fibrosis, exocrine pancreatic insufficiency, hemosuccus pancreaticus, congenital malformations of the pancreas such as pancreas divisum and annular pancreas, and/or pancreatic cancer.

The methods described herein can be used to treat, ameliorate the symptoms, prevent and/or slow the progression of a number of pancreatic diseases or their symptoms, such as those resulting in pathological damage to pancreatic architecture. The terms "pancreatic disease or disorder", "pancreatic disease", "pancreatic condition" and "pancreatic disorder" are used interchangeably herein and refer to any condition and/or disorder relating to the structure or function of the pancreas, including the endocrine cells (alpha, beta, delta, epsilon, PP) and exocrine cells (acinar, centroacinar, duct). Such pancreatic diseases include, but are not limited to, type 1 diabetes, type 2 diabetes, pancreatitis, cystic fibrosis, exocrine pancreatic insufficiency, hemosuccus pancreaticus, congenital malformations of the pancreas such as pancreas divisum and annular pancreas, and/or pancreatic cancer.

In some of these conditions, where inflammation plays a role in the pathology of the condition, therapeutic agents used together with the c-kit PSCs can ameliorate or slow the progression of the condition by reducing damage from inflammation. In other cases, therapeutic agents used together with the c-kit PSCs can act to limit pathogen replication or pathogen-associated pancreatic tissue damage.

As used herein, the terms "administering," "introducing", "transplanting" and "implanting" are used interchangeably in the context of the placement of cells, e.g., c-kit positive PSCs, of the invention into a subject, by a method or route which results in at least partial localization of the introduced cells at a desired site, such as a site of injury or repair, such that a desired effect(s) is produced. The cells e.g., c-kit positive PSCs, or their differentiated progeny (e.g., beta-like cells) can be implanted directly to the pancreas, or alternatively be administered by any appropriate route which results in delivery to a desired location in the subject where at least a portion of the implanted cells or components of the cells remain viable. The period of viability of the cells after administration to a subject can be as short as a few hours, e.g., twenty-four hours, to a few days, to as long as several years, i.e., long-term engraftment. For example, in some embodiments of all aspects of the therapeutic methods described herein, an effective amount of an isolated or enriched population of isolated c-kit positive PSCs is administered directly to the pancreas of an individual suffering from diabetes by direct injection. In other embodiments of all aspects of the therapeutic methods described herein, the population of isolated and enriched c-kit positive PSCs is administered via an indirect systemic route of administration, such as a catheter-mediated route.

One embodiment of the invention includes use of a catheter-based approach to deliver the injection. The use of a catheter precludes more invasive methods of delivery such as surgically opening the body to access the pancreas. As one skilled in the art is aware, optimum time of recovery would be allowed by the more minimally invasive procedure, which as outlined here, includes a catheter approach. When provided prophylactically, the isolated and enriched c-kit positive PSCs can be administered to a subject in advance of any symptom of a pancreatic disease or disorder. Accordingly, the prophylactic administration of an isolated or enriched for c-kit positive PSC population serves to prevent a pancreatic disease or disorder, or further progress of pancreatic diseases or disorders as disclosed herein.

When provided therapeutically, isolated and enriched c-kit positive PSCs are provided at (or after) the onset of a symptom or indication of a pancreatic disease or disorder, e.g., upon the onset of diabetes.

As used herein, the terms "treat," "treatment," "treating," or "amelioration" refer to therapeutic treatment, wherein the object is to reverse, alleviate, ameliorate, decrease, inhibit, or slow down the progression or severity of a condition associated with a disease or disorder. The term "treating" includes reducing or alleviating at least one adverse effect or symptom of a condition, disease or disorder associated with a pancreatic disease, such as, but not limited to, pancreatitis. Treatment is generally "effective" if one or more symptoms or clinical markers are reduced as that term is defined herein. Alternatively, treatment is "effective" if the progression of a disease is reduced or halted. That is, "treatment" includes not just the improvement of symptoms or markers, but also a cessation or at least slowing of progress or worsening of symptoms that would be expected in absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, and remission (whether partial or total), whether detectable or undetectable. In some embodiments, "treatment" and "treating" can also mean prolonging survival of a subject as compared to expected survival if the subject did not receive treatment.

As used herein, the term "prevention" refers to prophylactic or preventative measures wherein the object is to prevent or delay the onset of a disease or disorder, or delay the onset of symptoms associated with a disease or disorder. In some embodiments, "prevention" refers to slowing down the progression or severity of a condition or the deterioration of pancreatic function associated with a pancreatic disease or disorder.

In another embodiment, "treatment" of a pancreatic disease or disorder also includes providing relief from the symptoms or side-effects of the disease (including palliative treatment). For example, any reduction in blood glucose level, abdominal pain, nausea and/or vomiting, no matter how slight, would be considered an alleviated symptom. In some embodiments of the aspects described herein, the symptoms or a measured parameter of a disease or disorder are alleviated by at least 5%, at least 10%, at least 20%, at least 30%, at least 40%, at least 50%, at least 60%, at least 70%, at least 80%, or at least 90%, upon administration of a population of isolated and enriched PSCs, as compared to a control or non-treated subject.

Measured or measurable parameters include clinically detectable markers of disease, for example, elevated or depressed levels of a clinical or biological marker, as well as parameters related to a clinically accepted scale of symptoms or markers for a disease or disorder. It will be understood, however, that the total usage of the compositions as disclosed herein will be decided by the attending physician within the scope of sound medical judgment. The exact amount required will vary depending on factors such as the type of pancreatic disease or disorder being treated, degree of damage, whether the goal is treatment or prevention or both, age of the subject, the amount of cells available etc. Thus, one of skill in the art realizes that a treatment may improve the disease condition, but may not be a complete cure for the disease.

In one embodiment of all aspects of the therapeutic methods described, the term "effective amount" as used herein refers to the amount of a population of isolated or enriched for c-kit positive PSCs needed to alleviate at least one or more symptoms of the pancreatic disease or disorder, and relates to a sufficient amount of pharmacological composition to provide the desired effect, e.g., treat a subject having diabetes. The term "therapeutically effective amount" therefore refers to an amount of isolated and enriched for c-kit positive PSCs using the therapeutic methods as disclosed herein that is sufficient to effect a particular effect when administered to a typical subject, such as one who has or is at risk for diabetes.

In another embodiment of all aspects of the methods described, an effective amount as used herein would also include an amount sufficient to prevent or delay the development of a symptom of the disease, alter the course of a disease symptom (for example, but not limited to, slow the progression of a symptom of the disease), or even reverse a symptom of the disease. The effective amount of c-kit positive cells needed for a particular effect will vary with each individual and will also vary with the type of pancreatic disease or disorder being addressed. Thus, it is not possible to specify the exact "effective amount". However, for any given case, an appropriate "effective amount" can be determined by one of ordinary skill in the art using routine experimentation.

In some embodiments of all aspects of the therapeutic methods described, the subject is first diagnosed as having a disease or disorder affecting the pancreatic tissue prior to administering the cells according to the methods described herein. In some embodiments of all aspects of the therapeutic methods described, the subject is first diagnosed as being at risk of developing a pancreatic disease or disorder prior to administering the cells, e.g., an individual with a genetic disposition for diabetes or who has close relatives with diabetes.

For use in all aspects of the therapeutic methods described herein, an effective amount of isolated c-kit positive PSCs comprises at least $10^2$, at least $5\times10^2$, at least $10^3$, at least $5\times10^3$, at least $10^4$, at least $5\times10^4$, at least $10^5$, at least $2\times10^5$, at least $3\times10^5$, at least $4\times10^5$, at least $5\times10^5$, at least $6\times10^5$, at least $7\times10^5$, at least $8\times10^5$, at least $9\times10^5$, or at least $1\times10^6$ c-kit positive PSCs or multiples thereof per administration. In some embodiments, more than one administration of isolated c-kit positive PSCs is performed to a subject. The multiple administration of isolated c-kit positive PSCs can take place over a period of time. The c-kit positive PSCs can be isolated or enriched for from one or more donors, or can be obtained from an autologous source.

Exemplary modes of administration of PSCs and other agents for use in the methods described herein include, but are not limited to, injection, infusion, inhalation (including intranasal), ingestion, and rectal administration. "Injection" includes, without limitation, intravenous, intraarterial, intraductal, direct injection into the tissue intraventricular, intracardiac, transtracheal injection and infusion. The phrases "parenteral administration" and "administered parenterally" as used herein, refer to modes of administration other than enteral and topical administration, usually by injection, and includes, without limitation, intravenous, intraventricular, intracardiac, transtracheal injection and infusion. In some embodiments, c-kit positive PSCs can be administered by intravenous, intraarterial, intraductal, or direct injection into tissue, or through injection in the liver.

In some embodiments of all aspects of the therapeutic methods described, an effective amount of isolated c-kit positive PSCs is administered to a subject by injection. In other embodiments, an effective amount of isolated c-kit positive PSCs is administered to a subject by a catheter-mediated system. In other embodiments, an effective amount of isolated c-kit positive PSCs is administered to a subject through vessels, pancreatic duct, directly to the tissue, or a combination thereof. In additional embodiments, an effective amount of isolated c-kit positive PSCs is implanted in a patient in an encapsulating device (see, e.g., U.S. Pat. Nos. 9,132,226 and 8,425,928, the contents of each of which are incorporated herein by reference in their entirety).

In some embodiments of all aspects of the therapeutic methods described, an effective amount of isolated and enriched c-kit positive PSCs is administered to a subject by systemic administration, such as intravenous administration.

The phrases "systemic administration," "administered systemically", "peripheral administration" and "administered peripherally" as used herein refer to the administration of population of PSCs other than directly into the pancreas, such that it enters, instead, the subject's circulatory system.

In some embodiments of all aspects of the therapeutic methods described, one or more routes of administration are used in a subject to achieve distinct effects. For example, isolated or enriched population of c-kit positive PSCs are administered to a subject by both direct injection and catheter-mediated routes for treating or repairing exocrine and/or endocrine tissue. In such embodiments, different effective amounts of the isolated or enriched c-kit positive PSCs can be used for each administration route.

In some embodiments of all aspects of the therapeutic methods described, the methods further comprise administration of one or more therapeutic agents, such as a drug or a molecule, that can enhance or potentiate the effects mediated by the administration of the isolated or enriched c-kit positive PSCs, such as enhancing homing or engraftment of the PSCs, increasing repair of exocrine and/or endocrine cells, or increasing growth and regeneration of exocrine and/or endocrine cells. The therapeutic agent can be a protein (such as an antibody or antigen-binding fragment), a peptide, a polynucleotide, an aptamer, a virus, a small molecule, a chemical compound, a cell, a drug, etc.

As defined herein, "vascular regeneration" refers to de novo formation of new blood vessels or the replacement of damaged blood vessels (e.g., capillaries) after injuries or traumas, as described herein, including but not limited to, pancreatic disease. "Angiogenesis" is a term that can be used interchangeably to describe such phenomena.

In some embodiments of all aspects of the therapeutic methods described, the methods further comprise administration of c-kit positive PSCs together with growth, differentiation, and angiogenesis agents or factors that are known in the art to stimulate cell growth, differentiation, and angiogenesis in the pancreatic tissue. In some embodiments, any one of these factors can be delivered prior to or after administering the compositions described herein. Multiple subsequent delivery of any one of these factors can also occur to induce and/or enhance the engraftment, differentiation and/or angiogenesis. Suitable growth factors include but are not limited to transforming growth factor-beta (TGFβ), vascular endothelial growth factor (VEGF), platelet derived growth factor (PDGF), angiopoietins, epidermal growth factor (EGF), bone morphogenic protein (BMP), basic fibroblast growth factor (bFGF), insulin and 3-isobutyl-1-methylxasthine (IBMX). Other examples are described in Dijke et al., "Growth Factors for Wound Healing", Bio/Technology, 7:793-798 (1989); Mulder G D, Haberer P A, Jeter K F, eds. Clinicians' Pocket Guide to Chronic Wound Repair. 4th ed. Springhouse, Pa.: Springhouse Corporation; 1998:85; Ziegler T. R., Pierce, G. F., and Herndon, D. N., 1997, International Symposium on Growth Factors and Wound Healing: Basic Science & Potential Clinical Applications (Boston, 1995, Serono Symposia USA), Publisher: Springer Verlag, and these are hereby incorporated by reference in their entirety.

In one embodiment, the composition can include one or more bioactive agents to induce healing or regeneration of damaged pancreatic tissue, such as recruiting blood vessel forming cells from the surrounding tissues to provide connection points for the nascent vessels. Suitable bioactive agents include, but are not limited to, pharmaceutically active compounds, hormones, growth factors, enzymes, DNA, RNA, siRNA, viruses, proteins, lipids, polymers, hyaluronic acid, pro-inflammatory molecules, antibodies, antibiotics, anti-inflammatory agents, anti-sense nucleotides and transforming nucleic acids or combinations thereof. Other bioactive agents can promote increased mitosis for cell growth and cell differentiation.

A great number of growth factors and differentiation factors are known in the art to stimulate cell growth and differentiation of stem cells and progenitor cells. Suitable growth factors and cytokines include any cytokines or growth factors capable of stimulating, maintaining, and/or mobilizing progenitor cells. They include but are not limited to stem cell factor (SCF), granulocyte-colony stimulating factor (G-CSF), granulocyte-macrophage stimulating factor (GM-CSF), stromal cell-derived factor-1, steel factor, vascular endothelial growth factor (VEGF), TGFβ, platelet derived growth factor (PDGF), angiopoietins (Ang), epidermal growth factor (EGF), bone morphogenic protein (BMP), fibroblast growth factor (FGF), hepatocyte growth factor (HGF), insulin-like growth factor (IGF-1), interleukin (IL)-3, IL-1α, IL-1β, IL-6, IL-7, IL-8, IL-11, and IL-13, colony-stimulating factors, thrombopoietin, erythropoietin, fit3-ligand, and tumor necrosis factor α. Other examples are described in Dijke et al., "Growth Factors for Wound Healing", Bio/Technology, 7:793-798 (1989); Mulder G D, Haberer P A, Jeter K F, eds. Clinicians' Pocket Guide to Chronic Wound Repair. 4th ed. Springhouse, Pa.: Springhouse Corporation; 1998:85; Ziegler T. R., Pierce, G. F., and Herndon, D. N., 1997, International Symposium on Growth Factors and Wound Healing: Basic Science & Potential Clinical Applications (Boston, 1995, Serono Symposia USA), Publisher: Springer Verlag.

In one embodiment of all aspects of the therapeutic methods described, the composition described is a suspension of PSCs in a suitable physiologic carrier solution such as saline. The suspension can contain additional bioactive agents include, but are not limited to, pharmaceutically active compounds, hormones, growth factors, enzymes, DNA, RNA, siRNA, viruses, proteins, lipids, polymers, hyaluronic acid, pro-inflammatory molecules, antibodies, antibiotics, anti-inflammatory agents, anti-sense nucleotides and transforming nucleic acids or combinations thereof.

In certain embodiments of all aspects of the therapeutic methods described, the bioactive agent is a "pro-angiogenic factor," which refers to factors that directly or indirectly promote new blood vessel formation in the pancreas. The pro-angiogenic factors include, but are not limited to epidermal growth factor (EGF), E-cadherin, VEGF, angiogenin, angiopoietin-1, fibroblast growth factors: acidic (aFGF) and basic (bFGF), fibrinogen, fibronectin, heparanase, hepatocyte growth factor (HGF), angiopoietin, hypoxia-inducible factor-1 (HIF-1), insulin-like growth factor-1 (IGF-1), IGF, BP-3, platelet-derived growth factor (PDGF), VEGF-A, VEGF-C, pigment epithelium-derived factor (PEDF), vascular permeability factor (VPF), vitronection, leptin, trefoil peptides (TFFs), CYR61 (CCN1), NOV (CCN3), leptin, midkine, placental growth factor platelet-derived endothelial cell growth factor (PD-ECGF), platelet-derived growth factor-BB (PDGF-BB), pleiotrophin (PTN), progranulin, proliferin, transforming growth factor-alpha (TGF-alpha), transforming growth factor-beta (TGF-beta), tumor necrosis factor-alpha (TNF-alpha), c-Myc, granulocyte colony-stimulating factor (G-CSF), stromal derived factor 1 (SDF-1), scatter factor (SF), osteopontin, stem cell factor (SCF), matrix metalloproteinases (MMPs), thrombospondin-1 (TSP-1), pleitrophin, proliferin, follistatin, placental growth factor (PIGF), midkine, platelet-derived growth factor-BB (PDGF), and fractalkine, and inflammatory cytokines and chemokines that are inducers of angiogenesis and increased vascularity, e.g., interleukin-3 (IL-3), interleukin-8 (IL-8), CCL2 (MCP-1), interleukin-8 (IL-8) and CCL5 (RANTES).

Suitable dosage of one or more therapeutic agents in the compositions described herein can include a concentration of about 0.1 to about 500 ng/ml, about 10 to about 500 ng/ml, about 20 to about 500 ng/ml, about 30 to about 500 ng/ml, about 50 to about 500 ng/ml, or about 80 ng/ml to about 500 ng/ml. In some embodiments, the suitable dosage of one or more therapeutic agents is about 10, about 25, about 45, about 60, about 75, about 100, about 125, about 150, about 175, about 200, about 225, about 250, about 275, about 300, about 325, about 350, about 375, about 400, about 425, about 450, about 475, or about 500 ng/ml. In other embodiments, suitable dosage of one or more therapeutic agents is about 0.6, about 0.7, about 0.8, about 0.9, about 1.0, about 1.5, or about 2.0 µg/ml.

In some embodiments of all aspects of the therapeutic methods described, the methods further comprise administration of one or more surfactants as therapeutic agents, or may be used in combination with one or more surfactant therapies. Surfactant, as used herein, refers to any surface active agent, including but not limited to wetting agents, surface tension depressants, detergents, dispersing agents and emulsifiers. Particularly preferred are those that from a monomolecular layer over pulmonary alveolar surfaces, including but not limited to lipoproteins, lecithins, phosphatidylglycerol (PG), dipalmitoyl-phosphatidyl choline (DPPG), apoprotein A, apoprotein B, apoprotein C, apoprotein D, palmitoyl oleoyl, phosphatidyl glycerol palmitic and sphygomyelins. Exemplary surfactants include, but are not limited to surfactant protein A, surfactant protein B, surfactant protein C, surfactant protein D, and mixtures and combinations thereof. Commercially available surfactants include, but are not limited to, KL-4, SURVANTA®, bovine lipid extract surfactant (BLES), INFASURF® (CALFACTANT®), CUROSURF®, HL-10, AEROSURF®, SUBOXONE®, ALVEOFACT®, SURFAXIN®, VENTICUTE®, PUMACTANT®/ALEC, and EXOSURF®.

In some embodiments of all aspects of the therapeutic methods described, administration of one or more other standard therapeutic agents can be combined with the administration of the enriched c-kit positive PSCs to treat pancreatic diseases or disorders, e.g., diabetes or pancreatitis, including the use of anticholinergic agents, β-2-adrenoreceptor agonists, such as formoterol or salmeterol, corticosteroids, antibiotics, anti-oxidation, antihypertension agents, nitric oxide, caffeine, dexamethasone, and IL-10 or other cytokines. In some embodiments, the included standard therapeutic agents are use for treating the symptoms of the pancreatic disease.

For example, the use of c-kit positive PSCs in the methods described herein to treat, ameliorate or slow the progression of a condition such as cystic fibrosis (CF) can be optionally combined with other suitable treatments or therapeutic agents. For CF, this includes, but is not limited to, oral or aerosol corticosteroid treatment, ibuprofen treatment, DNAse or IL-10 treatment, diet control, e.g., vitamin E supplementation, vaccination against pathogens, e.g., *Haemophilus influenzae*, chest physical therapy, e.g., chest drainage or percussion, or any combination therein.

In some embodiments of all aspects of the therapeutic methods described, the standard therapeutic agents are those that have been described in detail, see, e.g., Harrison's Principles of Internal Medicine, 15.sup.th edition, 2001, E. Braunwald, et al., editors, McGraw-Hill, New York, N.Y., ISBN 0-07-007272-8, especially chapters 252-265 at pages 1456-1526; Physicians Desk Reference 54.sup.th edition, 2000, pages 303-3251, ISBN 1-56363-330-2, Medical Economics Co., Inc., Montvale, N.J. Treatment of any pancreatic disease or disorder can be accomplished using the treatment regimens described herein. For chronic conditions, intermittent dosing can be used to reduce the frequency of treatment. Intermittent dosing protocols are as described herein.

For the clinical use of the methods described herein, isolated or enriched populations of enriched c-kit positive PSCs described herein can be administered along with any pharmaceutically acceptable compound, material, carrier or composition which results in an effective treatment in the subject. Thus, a pharmaceutical formulation for use in the methods described herein can contain an isolated or enriched population of c-kit positive PSCs in combination with one or more pharmaceutically acceptable ingredients.

The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations, and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in Remington's Pharmaceutical Sciences, 18th Ed., Gennaro, ed. (Mack Publishing Co., 1990). The formulation should suit the mode of administration.

In one embodiment, the term "pharmaceutically acceptable" means approved by a regulatory agency of the Federal or a state government or listed in the U.S. Pharmacopeia or other generally recognized pharmacopeia for use in animals, and more particularly in humans. Specifically, it refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent, media (e.g., stem cell media), encapsulating material, manufacturing aid (e.g., lubricant, talc magnesium, calcium or zinc stearate, or steric acid), or solvent encapsulating material, involved in maintaining the activity of, carrying, or transporting the isolated or enriched populations of PSCs from one organ, or portion of the body, to another organ, or portion of the body.

Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) phosphate buffered solutions; (3) pyrogen-free water; (4) isotonic saline; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) cellulose, and its derivatives, such as sodium carboxymethyl cellulose, methylcellulose, ethyl cellulose, microcrystalline cellulose and cellulose acetate; (17) powdered tragacanth; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (24) C2-C12 alcohols, such as ethanol; (25) starches, such as corn starch and potato starch; and (26) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein.

Definitions

Unless otherwise defined, all technical and scientific terms used herein have the same meaning as commonly understood by one of ordinary skill in the art to which this invention belongs. Certain terms employed herein, in the specification, examples and claims are collected here.

As used herein, in vivo (Latin for "within the living") refers to those methods using a whole, living organism, such as a human subject. As used herein, "ex vivo" (Latin: out of the living) refers to those methods that are performed outside the body of a subject, and refers to those procedures in which an organ, cells, or tissue are taken from a living subject for a procedure, e.g., isolating c-kit positive PSCs from pancreatic tissue obtained from a donor subject, and then administering the isolated c-kit positive PSCs sample to a recipient subject. As used herein, "in vitro" refers to those methods performed outside of a subject, such as an in vitro cell culture experiment. For example, isolated c-kit positive PSCs can be cultured in vitro to expand or increase the number of c-kit positive PSCs, or to direct differentiation of the PSCs to a specific lineage or cell type, e.g., beta cells, prior to being used or administered according to the methods described herein.

The term "pluripotent" as used herein refers to a cell with the capacity, under different conditions, to commit to one or more specific cell type lineage and differentiate to more than one differentiated cell type of the committed lineage, and preferably to differentiate to cell types characteristic of all three germ cell layers. Pluripotent cells are characterized primarily by their ability to differentiate to more than one cell type, preferably to all three germ layers, using, for example, a nude mouse teratoma formation assay. Pluripotency is also evidenced by the expression of embryonic stem (ES) cell markers, although the preferred test for pluripotency is the demonstration of the capacity to differentiate into cells of each of the three germ layers. It should be noted that simply culturing such cells does not, on its own, render them pluripotent. Reprogrammed pluripotent cells (e.g., iPS cells as that term is defined herein) also have the characteristic of the capacity of extended passaging without loss of growth potential, relative to primary cell parents, which generally have capacity for only a limited number of divisions in culture.

The term "progenitor" cell are used herein refers to cells that have a cellular phenotype that is more primitive (i.e., is at an earlier step along a developmental pathway or progression than is a fully differentiated or terminally differentiated cell) relative to a cell which it can give rise to by differentiation. Often, progenitor cells also have significant or very high proliferative potential. Progenitor cells can give rise to multiple distinct differentiated cell types or to a single differentiated cell type, depending on the developmental pathway and on the environment in which the cells develop and differentiate. Progenitor cells give rise to precursor cells of specific determinate lineage, for example, certain pancreatic progenitor cells divide to give endocrine cell lineage precursor cells. These precursor cells divide and give rise to many cells that terminally differentiate to, for example, beta cells.

The term "precursor" cell is used herein refers to a cell that has a cellular phenotype that is more primitive than a terminally differentiated cell but is less primitive than a stem cell or progenitor cell that is along its same developmental pathway. A "precursor" cell is typically progeny cells of a "progenitor" cell which are some of the daughters of "stem cells". One of the daughters in a typical asymmetrical cell division assumes the role of the stem cell.

The term "embryonic stem cell" is used to refer to the pluripotent stem cells of the inner cell mass of the embryonic blastocyst (see U.S. Pat. Nos. 5,843,780, 6,200,806). Such cells can similarly be obtained from the inner cell mass of blastocysts derived from somatic cell nuclear transfer (see, for example, U.S. Pat. Nos. 5,945,577, 5,994,619, 6,235, 970). The distinguishing characteristics of an embryonic stem cell define an embryonic stem cell phenotype. Accordingly, a cell has the phenotype of an embryonic stem cell if it possesses one or more of the unique characteristics of an embryonic stem cell such that the cell can be distinguished from other cells. Exemplary distinguishing embryonic stem cell characteristics include, without limitation, gene expression profile, proliferative capacity, differentiation capacity, karyotype, responsiveness to particular culture conditions, and the like.

The term "adult stem cell" is used to refer to any multipotent stem cell derived from non-embryonic tissue, including juvenile and adult tissue. In some embodiments, adult stem cells can be of non-fetal origin.

In the context of cell ontogeny, the adjective "differentiated" or "differentiating" is a relative term meaning a "differentiated cell" is a cell that has progressed further down the developmental pathway than the cell it is being compared with. Thus, stem cells can differentiate to lineage-restricted precursor cells (such as a pancreatic stem cell), which in turn can differentiate into other types of precursor cells further down the pathway (such as an exocrine or endocrine precursor), and then to an end-stage differentiated cell, which plays a characteristic role in a certain tissue type, and may or may not retain the capacity to proliferate further.

The term "differentiated cell" is meant any primary cell that is not, in its native form, pluripotent as that term is defined herein. Stated another way, the term "differentiated cell" refers to a cell of a more specialized cell type derived from a cell of a less specialized cell type (e.g., a stem cell such as a pancreatic stem cell) in a cellular differentiation process. Without wishing to be limited to theory, a pluripotent stem cell in the course of normal ontogeny can differentiate first to an endocrine or exocrine cell. Further differentiation of a pancreatic stem cell leads to the formation of the various pancreatic cell types, including alpha cells, beta cells, delta cells, epsilon cells, PP cells, acinar cells, centroacinar cells or ductal cells.

As used herein, the term "somatic cell" refers to any cell forming the body of an organism, as opposed to germline cells. In mammals, germline cells (also known as "gametes") are the spermatozoa and ova which fuse during fertilization to produce a cell called a zygote, from which the entire mammalian embryo develops. Every other cell type in the mammalian body—apart from the sperm and ova, the cells from which they are made (gametocytes) and undifferentiated stem cells—is a somatic cell: internal organs, skin, bones, blood, and connective tissue are all made up of somatic cells. In some embodiments the somatic cell is a "non-embryonic somatic cell", by which is meant a somatic cell that is not present in or obtained from an embryo and does not result from proliferation of such a cell in vitro. In some embodiments the somatic cell is an "adult somatic cell", by which is meant a cell that is present in or obtained from an organism other than an embryo or a fetus or results from proliferation of such a cell in vitro.

As used herein, the term "adult cell" refers to a cell found throughout the body after embryonic development.

The term "phenotype" refers to one or a number of total biological characteristics that define the cell or organism under a particular set of environmental conditions and factors, regardless of the actual genotype. For example, the expression of cell surface markers in a cell.

The term "cell culture medium" (also referred to herein as a "culture medium" or "medium") as referred to herein is a medium for culturing cells containing nutrients that maintain cell viability and support proliferation. The cell culture medium may contain any of the following in an appropriate combination: salt(s), buffer(s), amino acids, glucose or other sugar(s), antibiotics, serum or serum replacement, and other components such as peptide growth factors, etc. Cell culture media ordinarily used for particular cell types are known to those skilled in the art.

The terms "renewal" or "self-renewal" or "proliferation" are used interchangeably herein, are used to refer to the ability of stem cells to renew themselves by dividing into the same non-specialized cell type over long periods, and/or many months to years.

In some instances, "proliferation" refers to the expansion of cells by the repeated division of single cells into two identical daughter cells.

The term "lineages" is used herein describes a cell with a common ancestry or cells with a common developmental fate.

The term "isolated cell" as used herein refers to a cell that has been removed from an organism in which it was originally found or a descendant of such a cell. Optionally the cell has been cultured in vitro, e.g., in the presence of other cells. Optionally the cell is later introduced into a second organism or re-introduced into the organism from which it (or the cell from which it is descended) was isolated.

The term "isolated population" with respect to an isolated population of cells as used herein refers to a population of cells that has been removed and separated from a mixed or heterogeneous population of cells. In some embodiments, an isolated population is a substantially pure population of cells as compared to the heterogeneous population from which the cells were isolated or enriched from.

The term "tissue" refers to a group or layer of specialized cells which together perform certain special functions. The term "tissue-specific" refers to a source of cells from a specific tissue.

The terms "decrease", "reduced", "reduction", "decrease" or "inhibit" are all used herein generally to mean a decrease by a statistically significant amount. However, for avoidance of doubt, "reduced", "reduction" or "decrease" or "inhibit" typically means a decrease by at least about 5%-10% as compared to a reference level, for example a decrease by at least about 20%, or at least about 30%, or at least about 40%, or at least about 50%, or at least about 60%, or at least about 70%, or at least about 80%, or at least about 90% decrease (i.e., absent level as compared to a reference sample), or any decrease between 10-90% as compared to a reference level. In the context of treatment or prevention, the reference level is a symptom level of a subject in the absence of administering a population of c-kit positive PSCs.

The terms "increased", "increase" or "enhance" are all used herein to generally mean an increase by a statically significant amount; for the avoidance of any doubt, the terms "increased", "increase" or "enhance" means an increase of at least 10% as compared to a reference level, for example an increase of at least about 20%, or at least about 30%, or at least about 40%, or at least about 50%, or at least about 60%, or at least about 70%, or at least about 80%, or at least about 90% increase or more, or any increase between 10-90% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level. In the context of c-kit positive PSC expansion in vitro, the reference level is the initial number of c-kit positive PSCs isolated from the pancreatic tissue sample.

The term "express at minimal levels" refers to the limited expression of endocrine or exocrine markers such as insulin, C-peptide, glucagon, CK19 and/or amylase in isolated c-kit positive pancreatic stem cells as measured by qRT-PCR, FACS, immunoprecipitation, Western blotting, ELISA, microarray, Nanostring®, mass spectrometry or other molecular quantitation techniques known in the art. Minimal levels of expression of endocrine and/or exocrine markers typically mean that each marker is expressing at that is not more than about 10%, not more than about 8%, not more than about 6%, not more than about 4%, not more than about 2%, not more than about 1% positive for that marker or less relative to c-kit expression, as determined by a molecular assay known to one skilled in the art.

The term "statistically significant" or "significantly" refers to statistical significance and generally means a two standard deviation (2SD) below normal, or lower, concentration of the marker. The term refers to statistical evidence that there is a difference. It is defined as the probability of making a decision to reject the null hypothesis when the null hypothesis is actually true. The decision is often made using the p-value.

As used herein the term "comprising" or "comprises" is used in reference to compositions, methods, and respective component(s) thereof, that are essential to the invention, yet open to the inclusion of unspecified elements, whether essential or not.

The term "consisting of" refers to compositions, methods, and respective components thereof as described herein, which are exclusive of any element not recited in that description of the embodiment.

Unless otherwise explained, all technical and scientific terms used herein have the same meaning as commonly understood by one of ordinary skill in the art to which this disclosure belongs. Definitions of common terms in molecular biology may be found in Benjamin Lewin, Genes IX, published by Jones & Bartlett Publishing, 2007 (ISBN-13: 9780763740634); Kendrew et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8). Further, unless otherwise required by context, singular terms shall include pluralities and plural terms shall include the singular.

Unless otherwise stated, the present invention was performed using standard procedures known to one skilled in the art, for example, in Maniatis et al., Molecular Cloning: A Laboratory Manual, Cold Spring Harbor Laboratory Press, Cold Spring Harbor, N.Y., USA (1982); Sambrook et al., Molecular Cloning: A Laboratory Manual (2 ed.), Cold Spring Harbor Laboratory Press, Cold Spring Harbor, N.Y., USA (1989); Davis et al., Basic Methods in Molecular Biology, Elsevier Science Publishing, Inc., New York, USA (1986); Current Protocols in Molecular Biology (CPMB) (Fred M. Ausubel, et al. ed., John Wiley and Sons, Inc.), Current Protocols in Immunology (CPI) (John E. Coligan, et. al., ed. John Wiley and Sons, Inc.), Current Protocols in Cell Biology (CPCB) (Juan S. Bonifacino et. al. ed., John Wiley and Sons, Inc.), Culture of Animal Cells: A Manual of Basic Technique by R. Ian Freshney, Publisher: Wiley-Liss; 5th edition (2005) and Animal Cell Culture Methods (Methods in Cell Biology, Vol. 57, Jennie P. Mather and David Barnes editors, Academic Press, 1st edition, 1998) which are all herein incorporated by reference in their entireties.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

Other than in the operating examples, or where otherwise indicated, all numbers expressing quantities of ingredients or reaction conditions used herein should be understood as modified in all instances by the term "about."

All patents and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

This invention is further illustrated by the following examples which should not be construed as limiting. The contents of all references cited throughout this application, as well as the figures are incorporated herein by reference.

Those skilled in the art will recognize, or be able to ascertain using not more than routine experimentation, many equivalents to the specific embodiments of the invention described herein, different culture medium and supplements can be used to culture expand the isolated cells. One skilled in the art would be able to perform tests to evaluate the choice of culture medium and supplements. Such equivalents are intended to be encompassed by the following claims.

The references cited herein and throughout the specification are incorporated herein by reference.

EXAMPLES

The inventors have employed the stem cell antigen c-kit as a marker for the identification and characterization of pancreatic primitive cells. The c-kit epitope was used to help uncover a pool of pancreatic stem cells (PSCs) which are self-renewing, clonogenic and multipotent. These PSCs are able to regenerate into cells that express markers of the endocrine pancreas such as insulin, C-peptide and glucagon and also into cells that express markers of the exocrine pancreas such as CK19 and amylase.

Materials and Methods hPSCs

Twenty-nine samples of human pancreatic tissue were obtained at surgery. A representative sample is shown in FIG. 1. For the isolation of human pancreatic stem cells (hPSCs), fragments were enzymatically dissociated employing a protocol developed in the inventors' laboratory for the collection and expansion of c-kit-positive stem cell classes in other organs, including the heart and the lung. Tissue fragments were enzymatically dissociated in a solution containing collagenase to obtain a single cell suspension. Cells were sorted with magnetic immunobeads for c-kit (Miltenyi®) and after sorting, cell phenotype was defined by immunocytochemistry. Putative hPSCs were then cultured in F12 medium (Gibco®) supplemented with 5-10% FBS (Gibco®) and insulin-selenium-transferrin mixture (Sigma). For immunocytochemistry, when possible, primary antibodies were directly labeled with fluorochromes (Molecular Probes®) to avoid cross-reactivity. Immunolabeling was analyzed by confocal microscopy.

Cloning Assay and Clonogenic Cell Differentiation

Human c-kit-positive cells were sorted and under microscopic control, individual c-kit-positive cells were seeded individually in single wells of 96-well plates. Wells containing more than one cell were excluded. Additionally, c-kit-positive cells were seeded at limiting dilution, approximately 100-150 cells in a Petri dish with a diameter of 10 cm. Differentiation of clonogenic cells was induced by MEM containing 10% FBS, $10^{-8}$ M dexamethasone. Cell phenotypes were defined by immunocytochemistry.

hPSC Division

Symmetric and asymmetric division of hPSCs was determined by immunolabeling of mitotic cells with α-adaptin antibody. Mitotic chromosomes were identified by staining with DAPI.

Quantitative RT-PCR

Total RNA was extracted with TRIzol™ from clonal hPSCs for the detection of transcripts for c-kit, markers for pancreatic endocrine cell differentiation (Pdx1, Nkx6.1, Ins, Ngn3), marker for pancreatic exocrine cell differentiation (Amy2A) and marker for pancreatic progenitor cells (Sox9). cDNA was generated from 2 μg of total RNA incubated with oligo(dT)15 primer for 2 hours at 37° C. RT-PCR was performed on 7300 Real-Time PCR Systems (Applied Biosystems) using ½oth of the cDNA per reaction. Cycling conditions were as follows: 95° C. for 10 minutes followed by 35 cycles of amplification (95° C. denaturation for 15 seconds, and 60° C. combined annealing/extension for 1 minute). Human-specific primers were designed with the Vector NTI software (INVITROGEN™). Quantified values were normalized against the input determined by the housekeeping human gene β2 microglobulin. Human pancreas total RNA (Applied Biosystems) and RNA extracted from a mouse pancreas were used as positive and negative controls, respectively.

PCR products were run on 2% agarose/1×TBE gel and DNA bands with the expected molecular size were obtained. DNA was extracted with QIAquick® Gel Extraction Kit (Qiagen®), eluted in 30 μl of 10 mM Tris buffer (pH 8.5) and amplified by Platinum® Blue PCR Supermix in the presence of the same forward and reverse primers used for real-time RT-PCR. PCR reaction was carried out in an Eppendorf Mastercycler®. Cycling conditions were as follows: 94° C.

for 2 minutes, followed by 20 cycles of amplification (94° C. denaturation for 15 seconds, 60° C. annealing for 30 seconds, 72° C. elongation for 15 seconds) with a final incubation at 72° C. for 2 minutes. After purification using QIAquick® PCR Purification kit, samples were sequenced. The human origin of the transcripts was confirmed by employing BLAST® searches.

mRNA Profiling of Clonal hPSCs mRNA profiling of clonal hPSCs was obtained by employing the Nanostring® assay. This technology enables the digital quantification of target RNA molecules using color-coded molecular probes and single-molecule imaging. The Nanostring® system possesses a high level of specificity and sensitivity so that one transcript copy per cell can be measured. The raw data produced by the Nanostring® analysis are normalized by the expression of housekeeping genes and the differential expression of genes among samples is shown as a heat-map. Total RNA was extracted with TRIzol™ from clonal hPSCs. A panel of 195 stem cell related human genes was examined. Gene expression was measured in untreated clonal hPSCs and clonal hPSCs exposed to the differentiation inducer dexamethasone (Dexa). In each clone, gene expression was shown as percent difference with respect to the corresponding clonal cells exposed to dexamethasone and was represented as a heat-map. The red color corresponds to a level of gene expression which is higher in the cells treated with Dexa than in the untreated cells. The blue color corresponds to a level of gene expression which is lower in the cells treated with Dexa than in the untreated cells.

Streptozotocin (STZ)-Induced Diabetic Mice, Transplantation and Measurements

Severe combined immunodeficient (SCID)/non-obese diabetic (NOD) mice will be used in this study. Methods for performing studies with these mice may be adapted from e.g., Hua et al., PLoS One, 2014 Jul. 10; 9(7):e102198. The mice will be maintained under specific pathogen-free conditions in an animal facility with controlled humidity, light, and temperature. The air in the facility will be passed through a HEPA filter system designed to exclude bacteria and viruses. Animals will be fed with ad libitum access to a standard irradiated diet.

To induce experimental diabetes, STZ will be injected intraperitoneally to mice every day. Four days after STZ injection, blood glucose levels will start to be measured every day using tail vein blood with a glucose meter. The mean blood glucose of mice will be determined before STZ injection and at 1-5 days after STZ administration to determine a mean blood glucose level that defines a diabetic mouse. The diabetic mice will then be injected with long-acting insulin every day until transplantation. Unsuccessful induced diabetic mice will be excluded from the study. Mice will be monitored for body weight and blood glucose levels every day or weekly.

c-kit-positive hPSCs will be transplanted into the abdominal fat pads, infused through the pancreatic duct and/or injected directly in the pancreas parenchyma of the SCID/NOD mice. Each mouse will receive about $10^6$ c-kit-positive hPSCs. The organs will be fixed in 10% formalin solution at early (2-4 days) and late (1-4 months) after transplantation to determine hPSC engraftment and tissue regeneration, respectively. The mean blood glucose level will be measured before and after transplantation on a weekly basis. Cell survival and function will be assessed by measuring serum human insulin levels.

Example 1

Figures 2A, 2B:
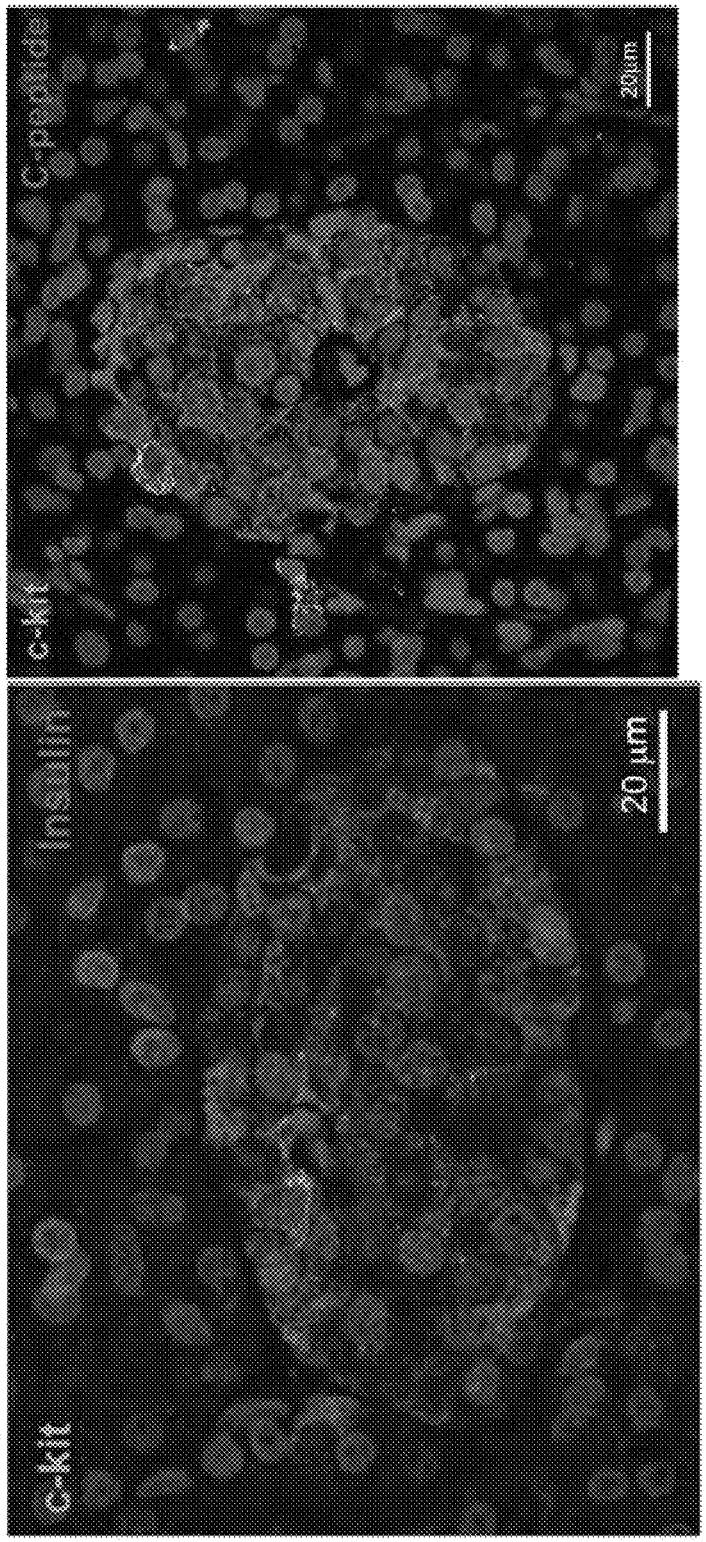
FIG. 2A shows representative immunohistochemistry (IHC) images of pancreatic cells stained for c-kit (green) and insulin (red). Cell nuclei were stained with DAPI.
FIG. 2B shows representative IHC images of pancreatic cells stained for c-kit (green) and C-peptide (red). Cell nuclei were stained with DAPI.
Figures 2C, 2D, 2E, 2F:
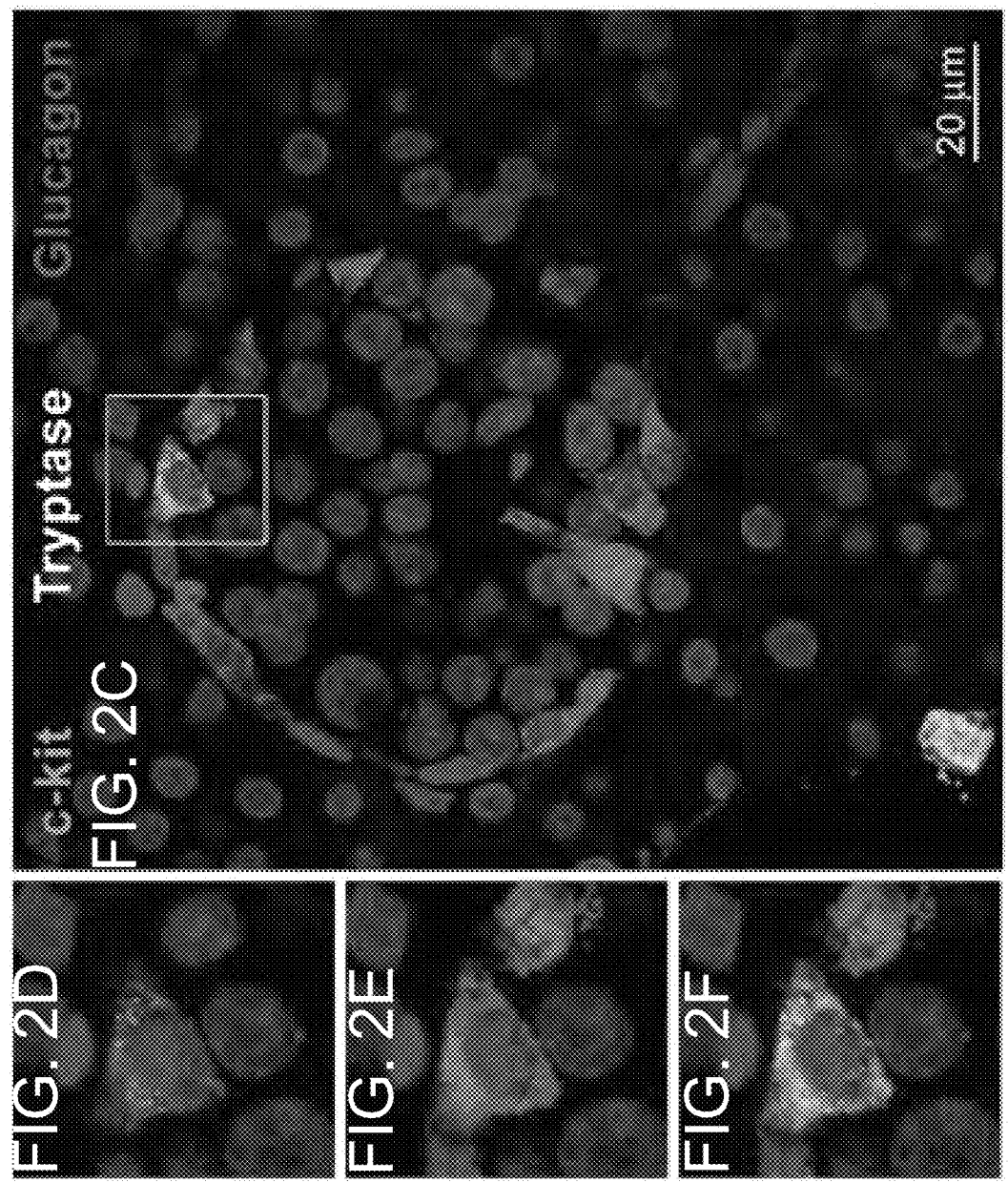
FIG. 2C shows representative IHC images of pancreatic cells stained for c-kit (green) and glucagon (red). Cell nuclei were stained with DAPI. Tryptase stain is shown in white and is a marker for mast cells.
FIG. 2D-FIG. 2F show magnification of the boxed area in FIG. 2C.

Identification of c-Kit-Positive Cells in Exocrine and Endocrine Pancreatic Tissue Samples were analyzed histologically to determine whether c-kit-positive cells were present in the pancreatic tissue. Cells were analyzed by immunohistochemistry using antibodies against c-kit and against insulin, C-peptide and glucagon, which are markers of commitment to endocrine cells producing insulin and C-peptide (β cells), or glucagon (α cells). Cells expressing the c-kit receptor were found in the endocrine (islets) and exocrine parts of the pancreas. In all cases, staining for tryptase was performed to exclude mast cells from the analysis. Importantly, cells showing c-kit and lineage markers were identified, suggesting that c-kit-positive cells may represent the source of the specialized cells in the pancreas. FIG. 2A shows some cells within the islets co-expressing c-kit and insulin. FIG. 2B shows some cells within the islets co-expressing c-kit and C-peptide. FIG. 2C shows some cells within the islets co-expressing c-kit and glucagon. Magnification of the boxed area in FIG. 2C is shown in FIG. 2D-FIG. 2F. The magnification shows a cell expressing c-kit (FIG. 2D), glucagon (FIG. 2E) and the co-expression of c-kit and glucagon through the merge of the two signals (FIG. 2F).

Figures 3A, 3B, 3C:
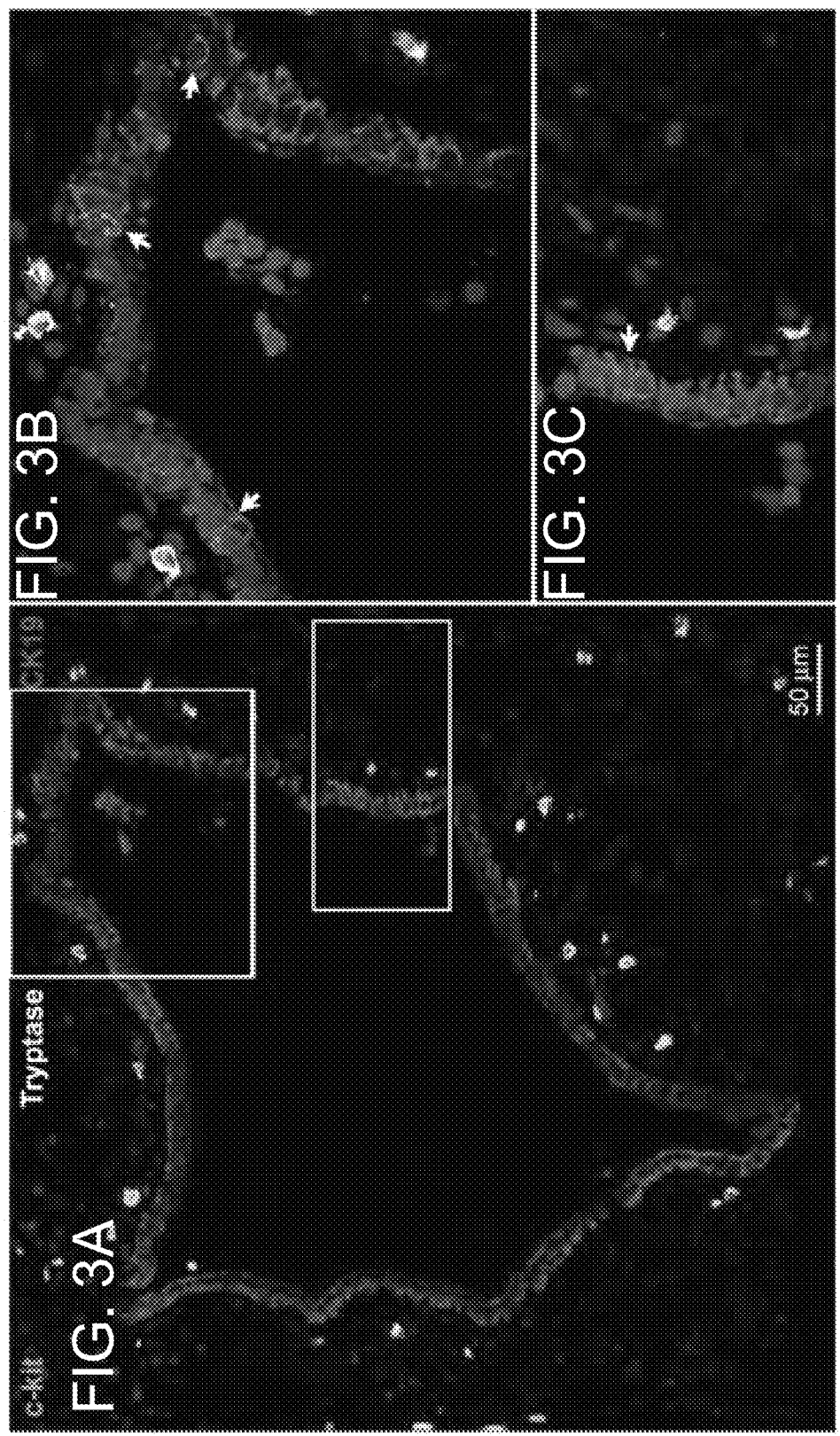
FIG. 3A-FIG. 3C show representative IHC images of cells associated with pancreatic ducts and exocrine pancreas stained for c-kit (green) and the epithelial marker CK19 (red).

C-kit-positive cells were identified within the epithelial lining of the ducts and in their proximity in the exocrine pancreas (FIG. 3A-FIG. 3C). At times c-kit-positive cells expressed the epithelial marker CK19 and the enzyme amylase. Magnification of the boxed areas in FIG. 3A is shown in FIG. 3B-FIG. 3C. FIG. 3B-FIG. 3C show some exocrine cells co-expressing c-kit and the epithelial marker CK19. Arrows in FIG. 3B-FIG. 3C indicate c-kit-positive cells.

Example 2

C-Kit-Positive Cells are Self-Renewing, Clonogenic and Multipotent

Figure 5:
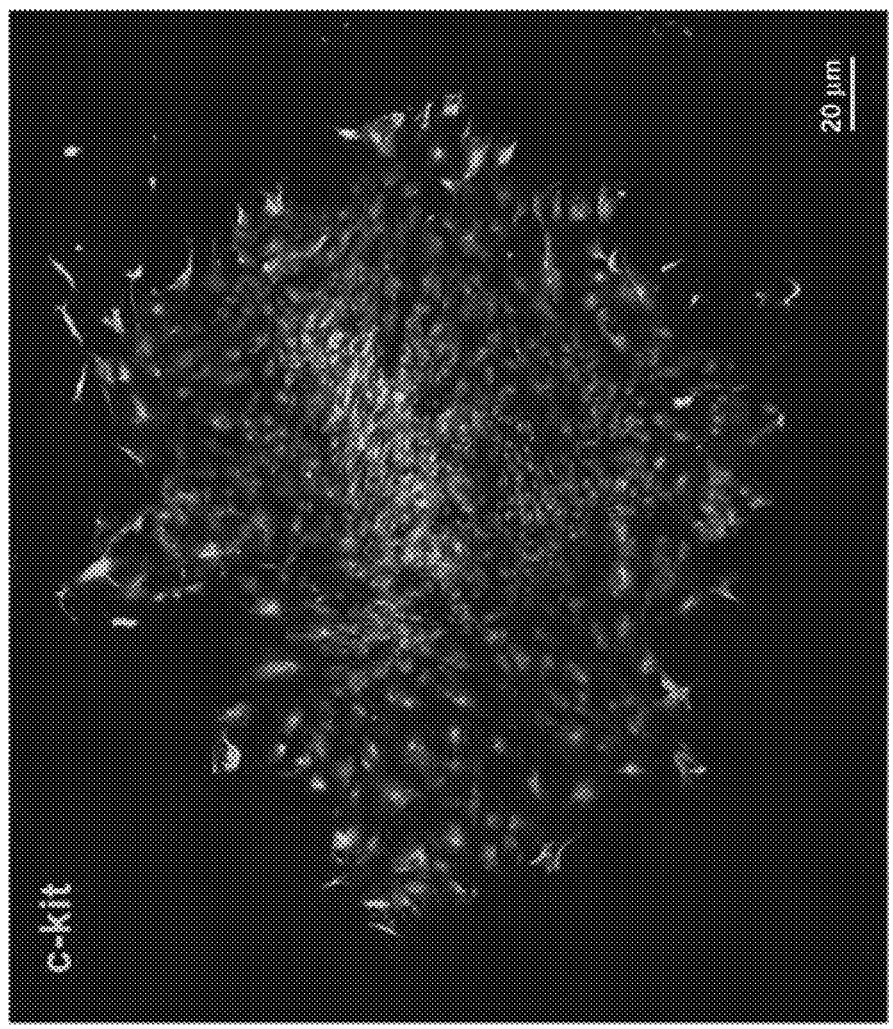
FIG. 5 shows representative IHC images of daughter cells from clones of c-kit positive cells stained for c-kit (green). Cell nuclei were stained with DAPI.

Pancreatic specimens were enzymatically dissociated to isolate and culture c-kit-positive cells, which were found to possess the three properties of stem cells: self-renewal, clonogenicity and multipotency.

c-kit-positive cells divide asymmetrically giving rise to a daughter stem cell and a daughter committed cell. Additionally, c-kit-positive cells can divide symmetrically. The modality of division was defined on the basis of the non-uniform or uniform distribution of the cell fate determinant α-adaptin (FIG. 4).

c-kit-positive cells deposited individually in single wells of a 96-well-plate gave rise to clones composed of daughter cells, which retained the expression of c-kit (FIG. 5).

Clonal c-kit-positive cells exposed to a differentiation medium ("Dexa" in FIG. 6A-FIG. 6R) acquired markers of endocrine and exocrine lineages. Differentiated c-kit-positive cells express the beta cell marker C-peptide (FIG. 6A-FIG. 6F), the endocrine alpha cell marker glucagon (FIG. 6G-FIG. 6L), and the exocrine cell marker amylase (FIG. 6M-FIG. 6R). Additionally, hPSCs secrete insulin in vitro after stimulation with glucose (FIG. 6S).

Example 3

In Vivo Studies of hPSCs in Diabetic SCID/NOD Mice

In vivo studies in which human pancreatic stem cells (PSCs) are delivered to the pancreas of diabetic SCID/NOD mice will be conducted. The objective is to establish whether PSCs can differentiate into insulin-producing β cells. This would result in a reduction of blood glucose levels and improvement of diabetes.

Example 4

The Human Pancreas Contains a Compartment of Insulin-Producing Stem Cells

Neogenesis of β-cells allows the endocrine pancreas to meet the increasing demands in insulin secretion with pregnancy, obesity, or following partial pancreatectomy. The prevailing view is that highly-specialized β-cells reenter the cell cycle and self-duplicate, restoring the β-cell mass and normalizing blood glucose level. Conversely, the recognition of a human pancreatic stem cell (hPSC) that regulates partly β-cell growth has been elusive. The present disclosure shows that the human pancreas possesses a pool of c-kit-positive-hPSCs that are self-renewing, clonogenic and multipotent, critical identifiers of tissue-specific adult stem cells. hPSCs commit to endocrine β-cells and α-cells, and exocrine acinar-cells in vitro and in vivo, generating the corresponding hormones and enzyme. Fate-mapping protocols in two mouse models have confirmed these observations, suggesting a new paradigm of pancreas biology. Understanding the mechanisms of β-cell formation may provide the opportunity to potentiate this naturally occurring process, offering a novel strategy for the management of human diabetes.

After maturation of the organism postnatally, several organs continue to possess a stem cell compartment that regulates physiologic cell turnover and contributes to tissue repair following injury. The endocrine pancreas develops from a transient population of neurogenin-3 (Ngn3)-positive progenitors that are, apparently, lost shortly after birth (Soyer et al., 2010). The neogenesis of β-cells, however, is the critical process that allows the endocrine pancreas to meet the increasing demands in insulin secretion occurring with pregnancy and obesity, or following partial pancreatectomy (Menge et al., 2012). Therefore, the fundamental question concerns the origin of insulin-secreting cells. The prevailing view is that the highly specialized, terminally-differentiated β-cells can reenter the cell cycle and self-duplicate, restoring the β-cell mass and normalizing the blood glucose level (Dirice et al., 2014; Dor et al., 2004; Mezza and Kulkarni, 2014).

The assumption that a terminally-differentiated cell can reenter the cell cycle and divide is per se a biological contradiction. Moreover, the notion that self-duplication is the mechanism of β-cell growth was derived from lineage tracing studies using reporter genes driven by the insulin promoter (Dor et al., 2004), which have inherent limitations. The major bias in this approach is that the presence of insulin is assumed to be restricted to functional β-cells. The hormone may be equally expressed in progenitor-precursor cells and amplifying cells, generated by activation and progressive lineage specification of an uncommitted, insulin-negative pancreatic stem cell (PSC). Insulin has been detected in developmentally heterogeneous cell populations, including Ngn3-positive and Pdx1-positive progenitor-precursor cells in the adult mouse and fetal human pancreas (Jiang and Morahan, 2012), suggesting that a more primitive cell may control β-cell growth and differentiation. However, the recognition of a unipotent or multipotent resident human PSC (hPSC) that regulates β-cell turnover and regeneration has been elusive.

The present disclosure shows that the adult human pancreas contains a pool of c-kit-positive cells, which are self-renewing, clonogenic and multipotent in vitro. Importantly, β-cells generated by commitment of c-kit-positive cells synthesize human insulin in response to glucose stimulation. Moreover, lineage tracing studies in mice support the notion that the endocrine and exocrine components of the pancreas derive in vivo from replication and differentiation of c-kit-positive cells. Together, these findings suggest that the mammalian pancreas is regulated by a compartment of resident stem cells which modulate organ homeostasis.

The Human Pancreas Contains c-Kit-Positive Cells

Figures 7A, 7B, 7C:
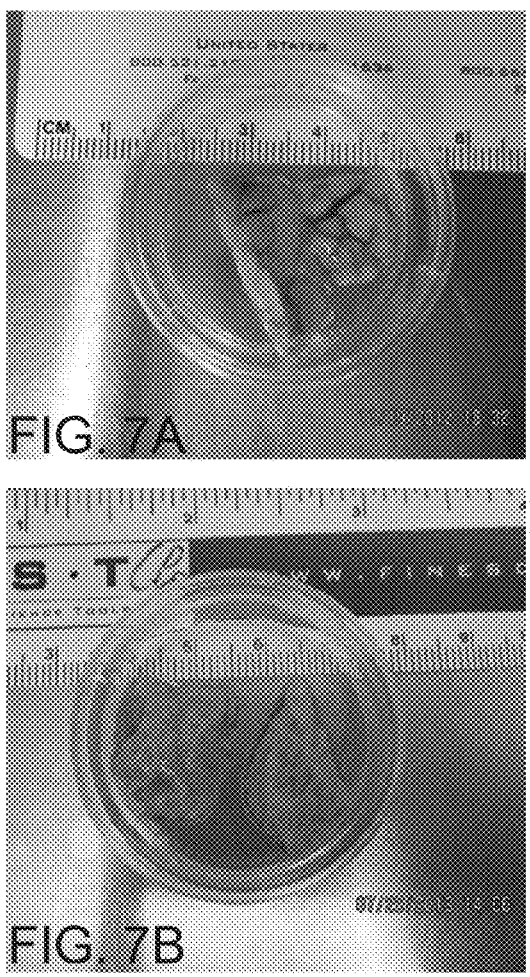
FIG. 7A-FIG. 7C show samples of human pancreas. Pancreatic specimens discarded at surgery are used for histology and isolation of c-kit-positive cells.

The c-kit epitope has been employed previously for the identification and characterization of hematopoietic, cardiac and lung stem cells (Beltrami et al., 2003; Ellison et al., 2013; Leri et al., 2015; Liu et al., 2015; Orlic et al., 1993), raising the possibility that this receptor tyrosine kinase may be expressed in other classes of tissue specific adult stem cells. The inventors tested whether the presence of c-kit would uncover a pool of hPSCs, which, by analogy to stem cells in other organs, are self-renewing, clonogenic and multipotent. Twenty-nine samples of normal appearing human pancreas discarded at surgery were included in this study (FIG. 7A-FIG. 7C). The c-kit receptor is highly expressed in the plasma membrane of mast-cells (Esposito et al., 2002) so that the absence and presence of tryptase was utilized to distinguish putative hPSCs and mast-cells, respectively.

Histologically, c-kit-positive tryptase-negative putative hPSCs were identified in all cases examined. They were located within the islets of Langerhans or in proximity of exocrine acinar-cells (FIG. 8A-FIG. 8R, and FIG. 9A-FIG. 9D); they were also found within the epithelial lining of small pancreatic ducts (FIG. 8S-FIG. 8V). The c-kit-positive tryptase-negative cells did not express C-peptide (FIG. 8A-FIG. 8G), amylase (FIG. 9A-FIG. 9D) and cytokeratin-19 (FIG. 8S-FIG. 8V), or were co-labeled by insulin (FIG. 8H-FIG. 8J) and glucagon (FIG. 8K-FIG. 8R).

Figure 8A:
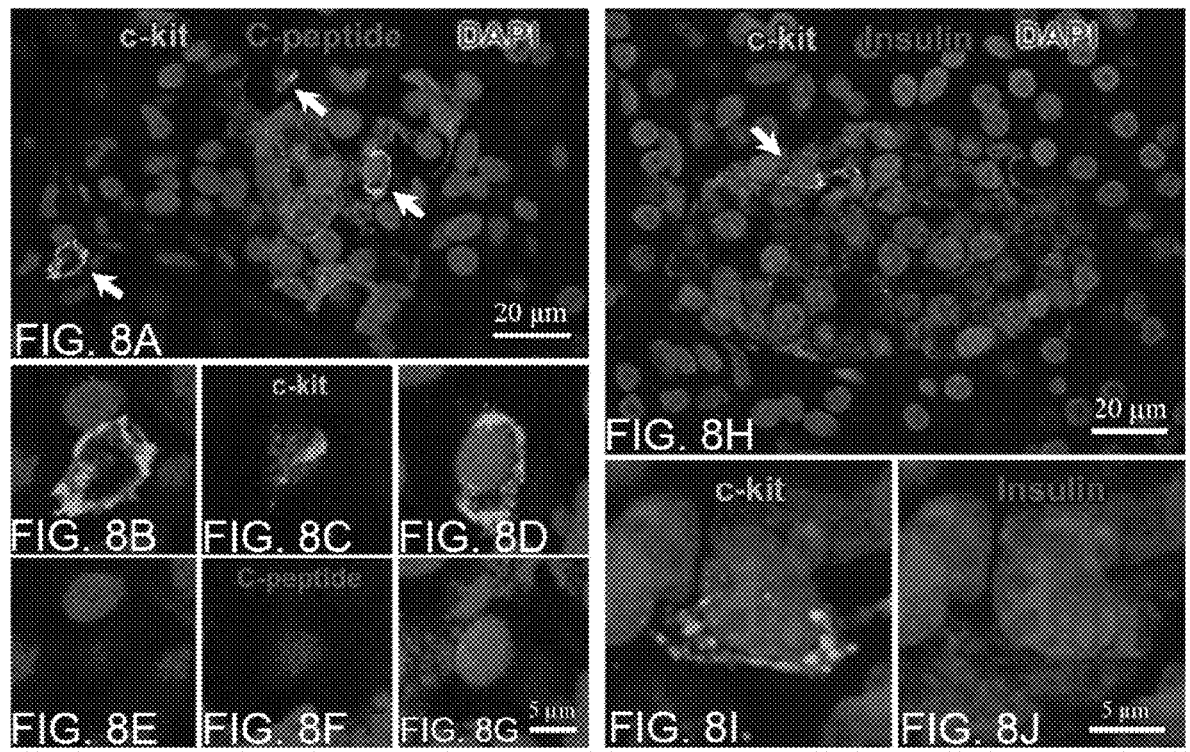
FIG. 8A-FIG. 8Y: c-kit-positive cells are present in the human pancreas.
Figure 8R:
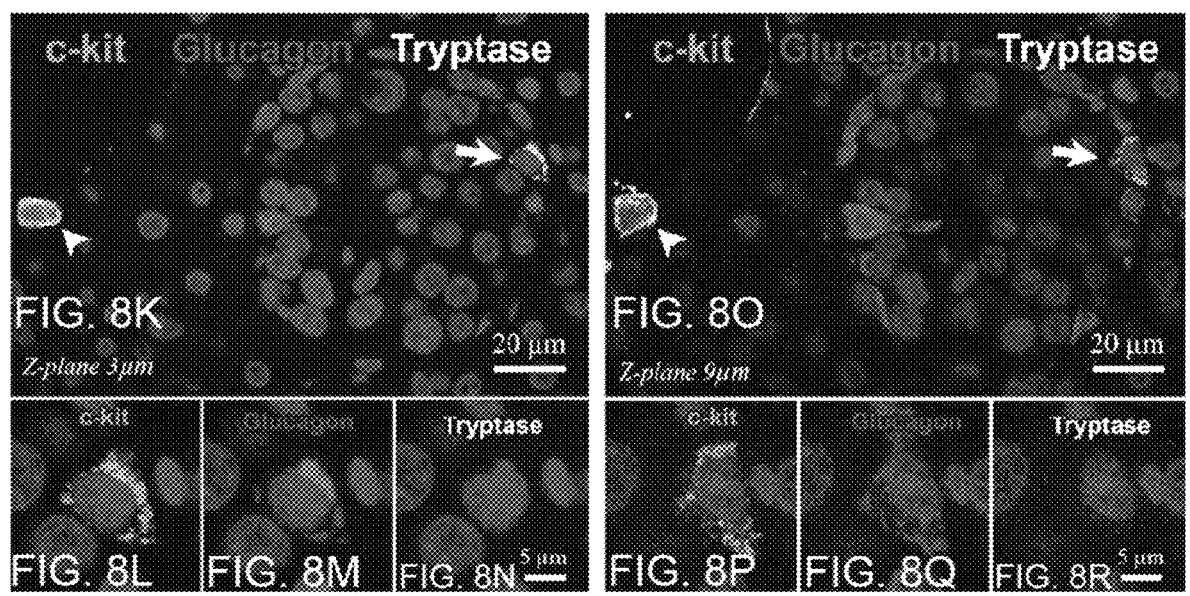
Figures 8S, 8T, 8U, 8V:
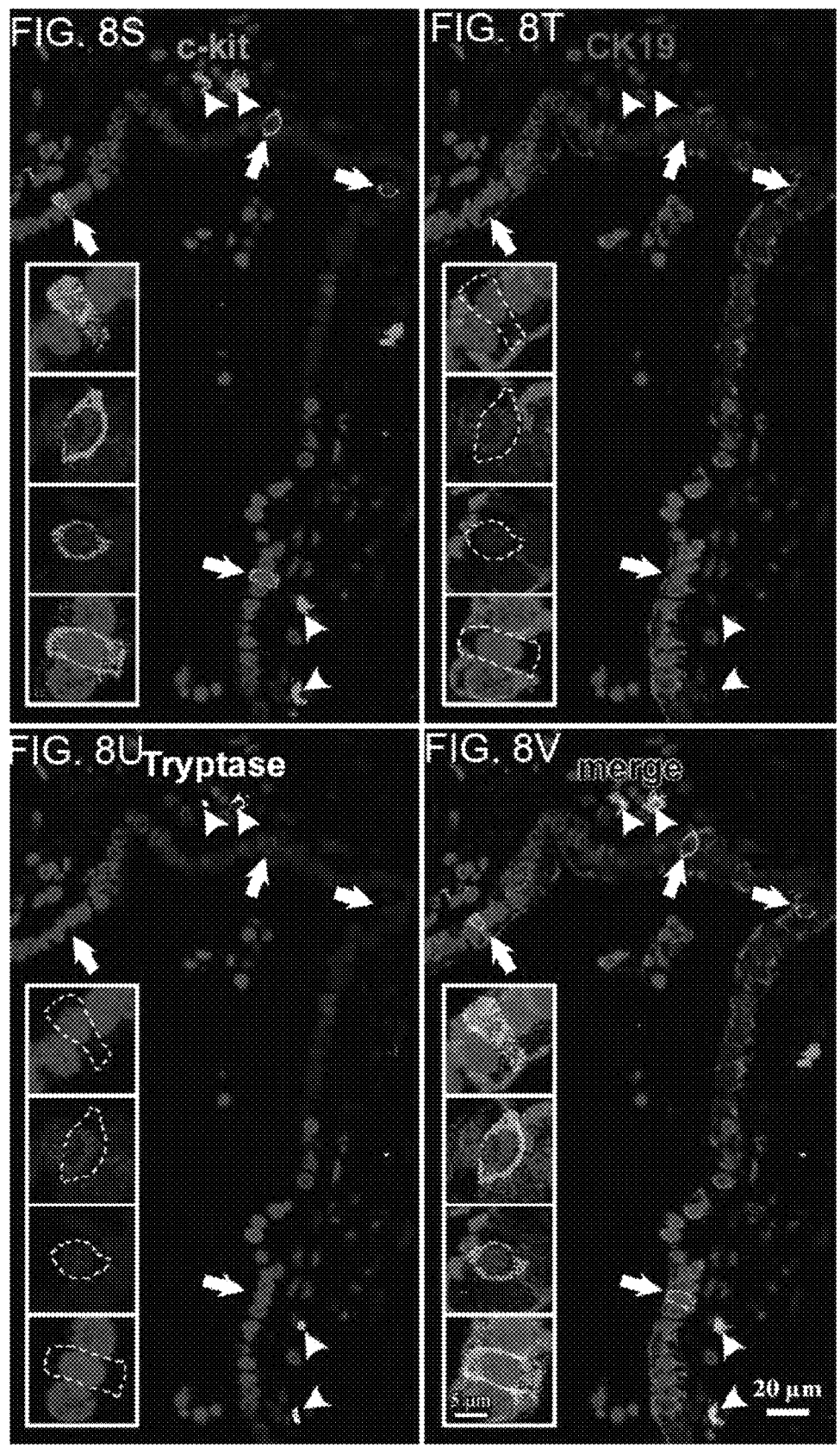
FIG. 8S-FIG. 8V: c-kit-positive cells (upper left panel, FIG. 8S; green) within the epithelium of a pancreatic duct stained by cytokeratin-19 (upper right panel, FIG. 8T; CK19, red). Arrows indicate 4 c-kit-positive (FIG. 8S), CK19-negative (FIG. 8T) and tryptase-negative (lower left panel, FIG. 8U; white) cells. Four mast-cells positive for c-kit and tryptase (arrowheads, FIG. 8S and FIG. 8U) are near the pancreatic duct. Insets: individual fluorescence channels. Dashed-lines define the c-kit-positive cells negative for tryptase and CK19. Right lower panel.
Figure 8W:
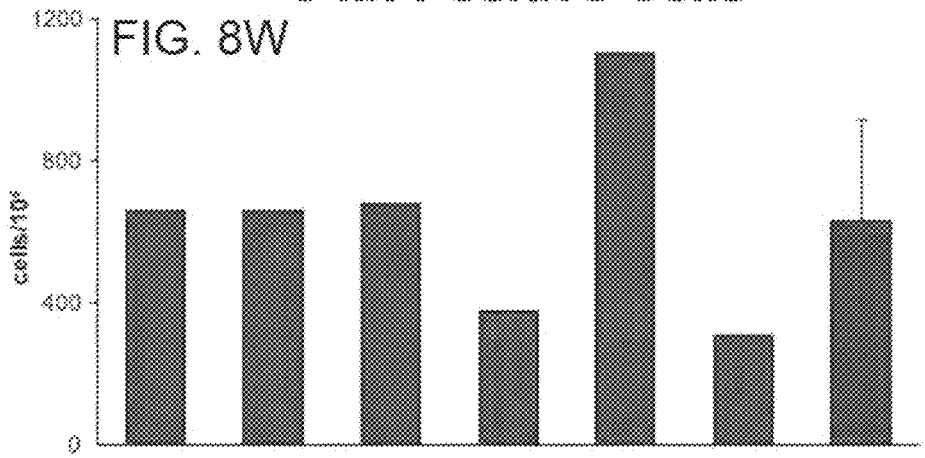
Figure 8X:
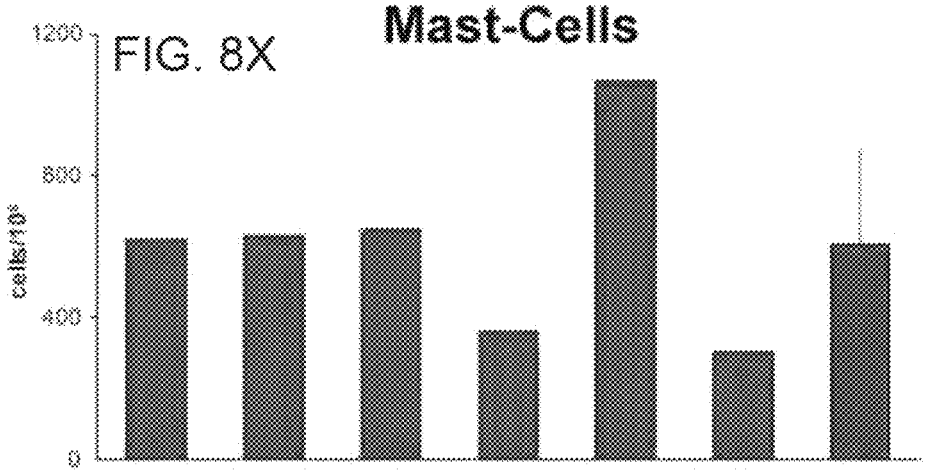
Figure 8Y:
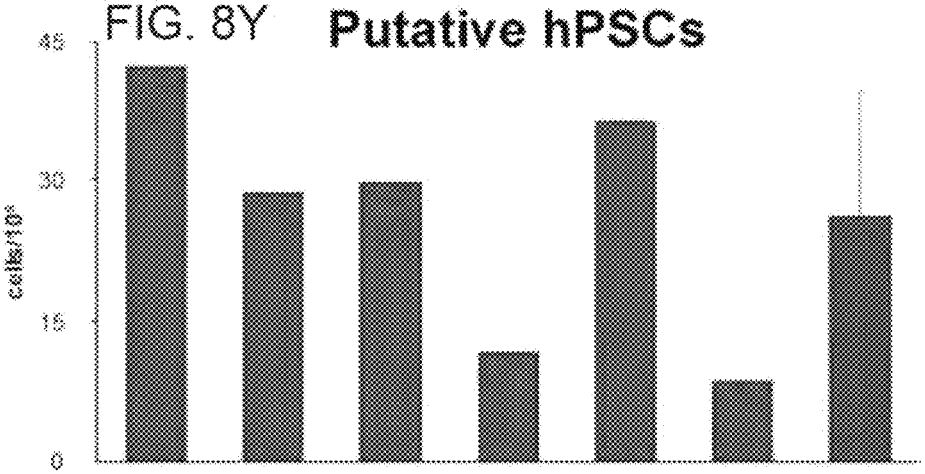
Figures 9A, 9B, 9C, 9D:
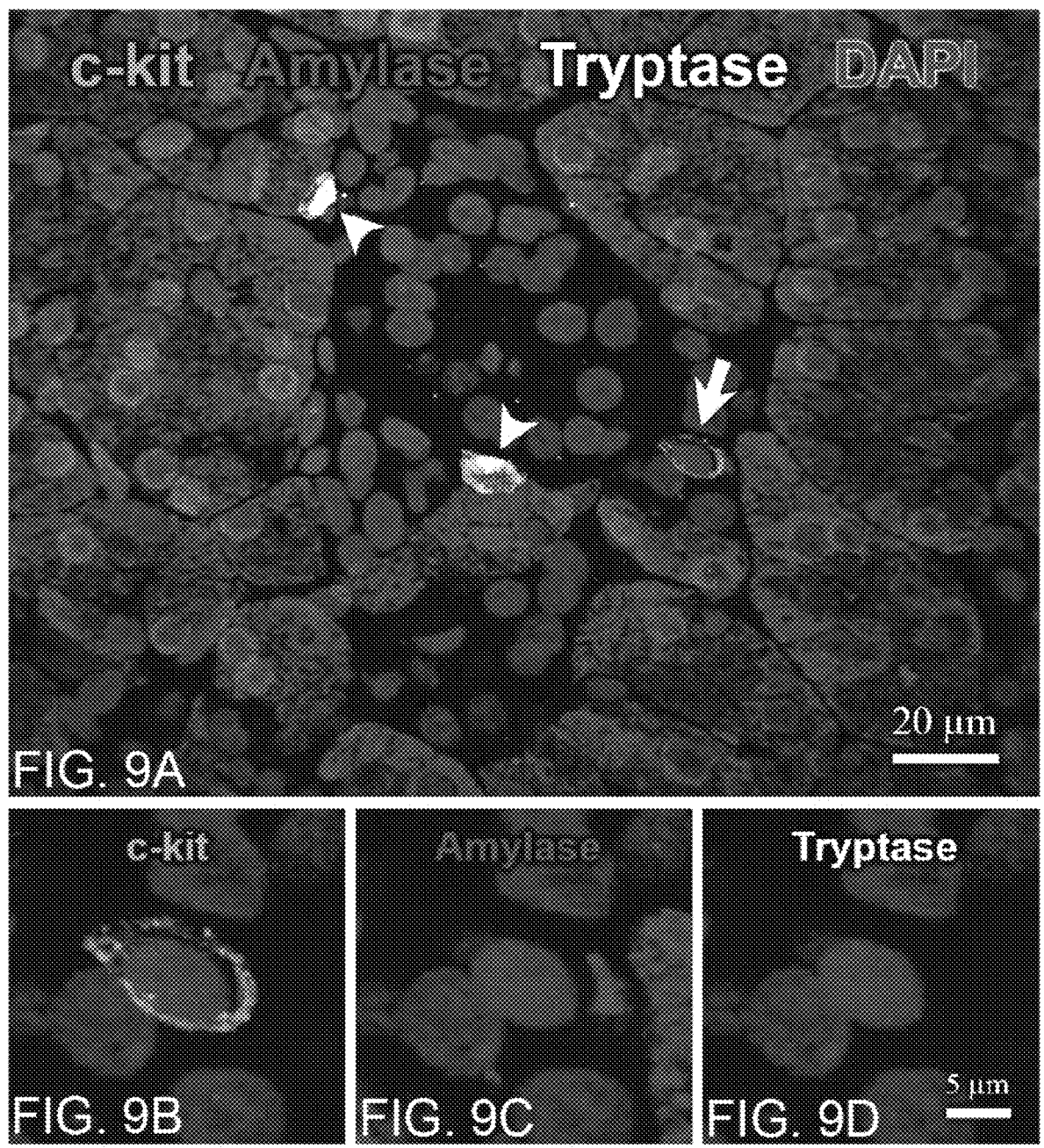
FIG. 9A-FIG. 9D: c-kit-positive cells are present in the human pancreas. Three c-kit-positive cells are in proximity of exocrine acinar-cells (amylase, red, FIG. 9A and FIG. 9B). Two are positive for c-kit and tryptase (white, FIG. 9A) representing mast-cells (arrowheads, FIG. 9A). The third c-kit-positive cell (FIG. 9B) is negative for tryptase and amylase (arrow, FIG. 9A, FIG. 9C and FIG. 9D). Insets: individual fluorescence channels (FIG. 9B-FIG. 9D); amylase is adjacent to, but not part of the c-kit-positive cell.

A quantitative analysis was performed to evaluate the number of c-kit-positive tryptase-negative and c-kit-positive tryptase-positive cells within the tissue (n=6). Mast-cells were identified throughout the parenchyma lacking a preferential anatomical localization. However, mast-cells were not detected within the epithelium of pancreatic ducts. There was an average of 631 c-kit-positive cells/$10^6$ pancreatic cells; c-kit-positive tryptase-negative putative hPSCs were present at a frequency of 26/$10^6$ pancreatic cells (FIG. 8Y), or 1 every 38,500 pancreatic cells. c-kit-positive tryptase-positive mast-cells comprised the large majority of c-kit-positive cells, 605/$10^6$ pancreatic cells (FIG. 8W-FIG. 8X). Putative hPSCs constituted 4% of the c-kit-positive cell pool, while mast-cells accounted for 96% of this cell compartment. Thus, the pancreas contains a rare population of c-kit-positive putative hPSCs which are uncommitted or co-express proteins indicative of lineage specification.

c-Kit-Positive Cells are Self-Renewing and Clonogenic

Figure 10A:
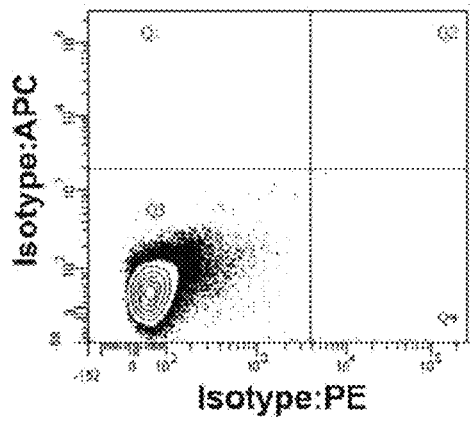
Figure 10B:
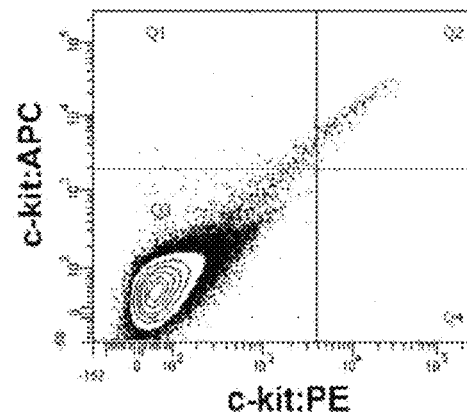
Figure 10C:
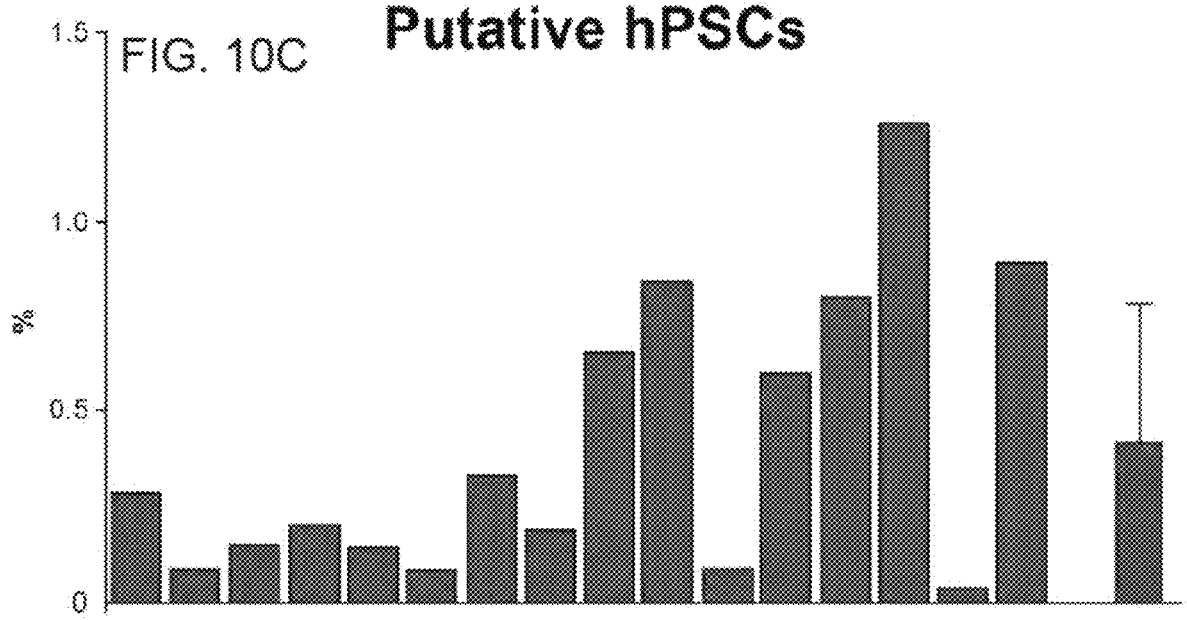
FIG. 10C: Quantitative data are shown individually (blue bars) and as mean±SD (red bar) (n=16).
Figures 10D, 10E, 10F, 10G, 10H, 10I, 10J, 10K:
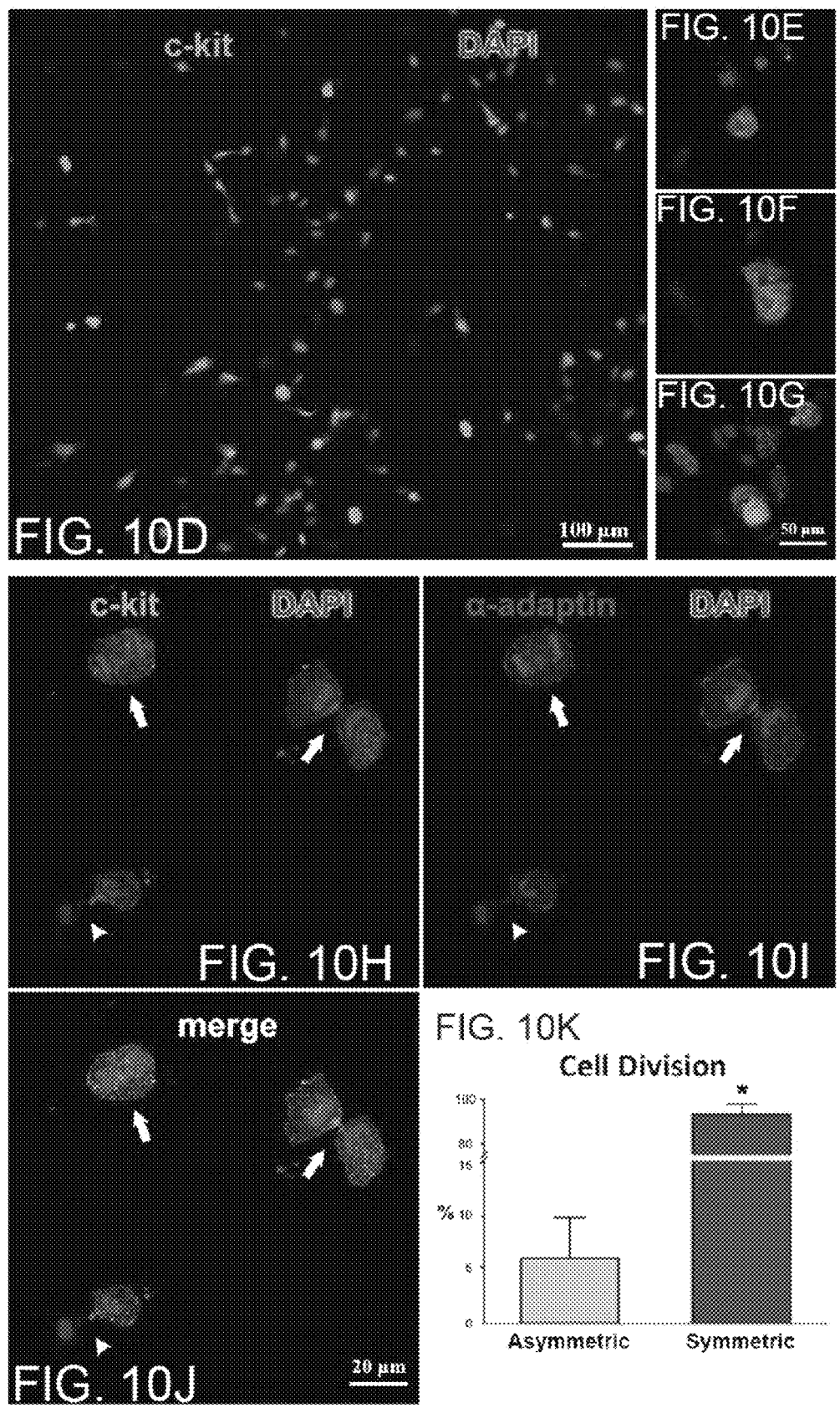
FIG. 10D-FIG. 10G: Culture of FACS-sorted c-kit-positive cells (green) illustrated at low (FIG. 10D) and higher magnification (FIG. 10E-FIG. 10G). Nuclei are stained by DAPI (blue). Most cells express c-kit.
FIG. 10H-FIG. 10K: Three dividing c-kit-positive cells (green, FIG. 10H) have chromosomes in late anaphase/telophase (upper left panel, FIG. 10H). Two of these mitotic cells (arrows) are dividing symmetrically; α-adaptin (red) is distributed in both daughter cells (upper right panel, FIG. 10I). The other c-kit-positive cell (arrowhead, FIG. 10H) is near the end of mitosis and is dividing asymmetrically; α-adaptin is restricted to one of the two daughter cells. Lower left panel (FIG. 10J), merge. Data are shown as mean±SD (n=5). *p<0.05 versus asymmetric cell division (FIG. 10K).

Tissue samples were employed for the isolation and in vitro propagation of c-kit-positive cells (n=16). Following enzymatic digestion and expansion of the un-fractionated cell compartment, cells were FACS-sorted with two monoclonal antibodies recognizing distinct epitopes of the c-kit receptor. Only cells reacting with both antibodies were collected to minimize unspecific binding (FIG. 10A-FIG. 10B). An average of 0.4% c-kit-positive cells were obtained from these preparations (FIG. 10C). Additionally, samples of the FACS-sorted c-kit-positive and c-kit-negative fractions were plated and stained with a third c-kit-antibody for specificity (FIG. 11A-FIG. 11B).

Subsequently, FACS-sorted c-kit-positive cells were plated for further expansion (FIG. 10D-FIG. 10G) and documentation of the pattern of cell division (n=5). The bipolar localization of the endocytic protein α-adaptin was employed to illustrate symmetric cell division, while the unipolar distribution of α-adaptin was used to document asymmetric cell division (Williams et al., 2011). Quantitatively, symmetric cell division predominated (FIG. 10H-FIG. 10K).

At P2-P4, c-kit-positive cells from 14 of the 29 tissue samples were FACS-sorted and seeded individually in single wells of 96-well-plates (FIG. 11C). Over a period of 3 weeks, multi-cellular clones were obtained and clonal efficiency determined (FIG. 10L-FIG. 10M, FIG. 10N-FIG. 10P, and FIG. 11D). Additionally, expanded c-kit-positive cells were negative for the hematopoietic cell lineages CD34 (FIG. 11F) and CD45 (FIG. 11G) and the epitope of mesenchymal stromal cells, CD90 (FIG. 11H). CD105 was detected in the majority of cells (FIG. 11I). Thus, the human pancreas possesses a pool of c-kit-positive cells which are self-renewing and clonogenic, and divide symmetrically and asymmetrically, all critical identifiers of tissue-specific adult stem cells.

The Molecular Signature of Individual hPSCs is Heterogeneous

To determine whether clonal hPSCs possess a transcriptional profile consistent with the undifferentiated and multipotent state of established pancreatic progenitors, qRT-PCR and NanoString® technology were employed. Separate clones derived from individual c-kit-positive cells were tested by qRT-PCR (n=4). Additionally, clonal hPSCs were treated with dexamethasone, $10^{-8}$ M, for a 7-day period to promote differentiation.

Clonal hPSCs expressed c-kit, together with Pdx1, Sox9 and Ngn3 (FIG. 12A), which are major determinants of progenitor cell fate (Arda et al., 2013; Jennings et al., 2015). All pancreatic cells derive from Pdx1 embryonic progenitors (Murtaugh and Melton, 2003), which give rise to exocrine acinar and ductal cells, and to the 4 endocrine cell types of the islets of Langerhans (Gu et al., 2002). The transcription factor Sox9 identifies in the embryonic pancreas a subset of mitotically active Pdx1-positive pluripotent progenitors (Gradwohl et al., 2000; Seymour, 2014). With dexamethasone, c-kit and Sox9 mRNA decreased significantly; however, the expression of Ngn3 and Pdx1 did not change (FIG. 12A). Thus, c-kit identifies a compartment of hPSCs that may comprise the other classes of previously recognized pancreatic progenitors.

The mRNA profiling of clonal hPSCs was obtained by employing the Nanostring® protocol (Manoranjan et al., 2013). This technology enables the digital quantification of target RNA molecules using color-coded molecular barcodes and single-molecule imaging. The Nanostring® system possesses a high level of specificity and sensitivity so that one transcript copy per cell can be measured. The raw data produced by the Nanostring® analysis are normalized based on the expression of the housekeeping genes, and the differential expression of genes among samples is shown as a heat-map.

A panel of 195 stem cell-related human genes was examined in single cell-derived clones of hPSCs (n=3). Gene expression was measured in untreated clonal cells and in clonal cells exposed to the differentiation inducer dexamethasone for a 7-day period. In each clone, gene expression is shown as percent difference with respect to the corresponding clonal cells not treated with dexamethasone and represented as a heat-map. The red color corresponds to a level of gene expression which is higher in the cells cultured in the presence of dexamethasone than in untreated cells. The blue color corresponds to a level of gene expression which is lower in the cells exposed to dexamethasone than in untreated cells.

The three sets of clonal cells showed distinct degrees of activation or repression of three signaling pathways: the Wnt/β-catenin pathway, the TGF-β/BMP pathway and the Notch pathway, which are important for stem cell maintenance and lineage determination. The Wnt/β-catenin pathway is required for the development of both the endocrine and exocrine compartments of the organ (Arda et al., 2013). The genes of the Wnt/β-catenin pathway were differentially regulated in the three sets of clonal cells (FIG. 12B), indicating a certain degree of molecular heterogeneity among clonal cells exposed to dexamethasone.

The TGF-β/BMP pathway is implicated in β-cell formation, and the inhibition of TGF-β promotes replication of β-cells, which, however, may be physiologically dysfunctional (Brown and Schneyer, 2010). In a manner similar to that observed for the Wnt/β-catenin pathway, gene transcripts of the TGF-β/BMP signaling axis were not equally modulated in the three samples (FIG. 12C), further suggesting that the cell clusters derived from replication of individual hPSCs reacted differently to dexamethasone.

Conversely, the components of the Notch pathway were similarly regulated in the three groups of clonal cells (FIG. 12D). Notch activation maintains the undifferentiated state of embryonic pancreatic progenitors, inhibiting endocrine and exocrine cell specification (Shih et al., 2012). Down-regulation of Notch and abrogation of the repressive function of Hes1 on Ngn3 is required for β-cell differentiation (Qu et al., 2013). The Delta-like ligand 1, the Jagged2 ligand, the Notch1, Notch2, Notch3 and Notch4 receptors, the transcription factor RBPjk, the zinc finger proteins GLI2 and GLI3, the transcriptional co-activators MAML2 and MAML3, and the cell fate determinant Numb were down-regulated by dexamethasone in the 3 sets of clonal hPSCs pointing to their acquisition of the β-cell lineage.

Collectively, Notch attenuation may favor the differentiation of clonal hPSCs towards the endocrine cell phenotype, although the inter-clonal variability in gene expression at baseline and after dexamethasone emphasizes their functional heterogeneity at the single cell level; this phenomenon is common to all classes of adult stem cells (Goodell et al., 2015).

Differentiating hPSCs Express C-Peptide, Glucagon, Amylase and Synthesize Human Insulin The molecular assays discussed above defined the mRNA profile of clonal c-kit-positive hPSCs at baseline and following exposure to dexamethasone. Subsequently, this analysis was complemented with the detection of specific cytoplasmic proteins to strengthen the multi-potentiality of this novel class of tissue-specific adult stem cells. FACS-sorted c-kit-positive hPSCs (n=4) were expanded and then cultured in differentiation medium containing dexamethasone; cells were examined one week later by immunolabeling and confocal microscopy.

Figures 12L, 12M, 12N, 12O, 12P, 12Q, 12R, 12S, 12T, 12U, 12V, 12W:
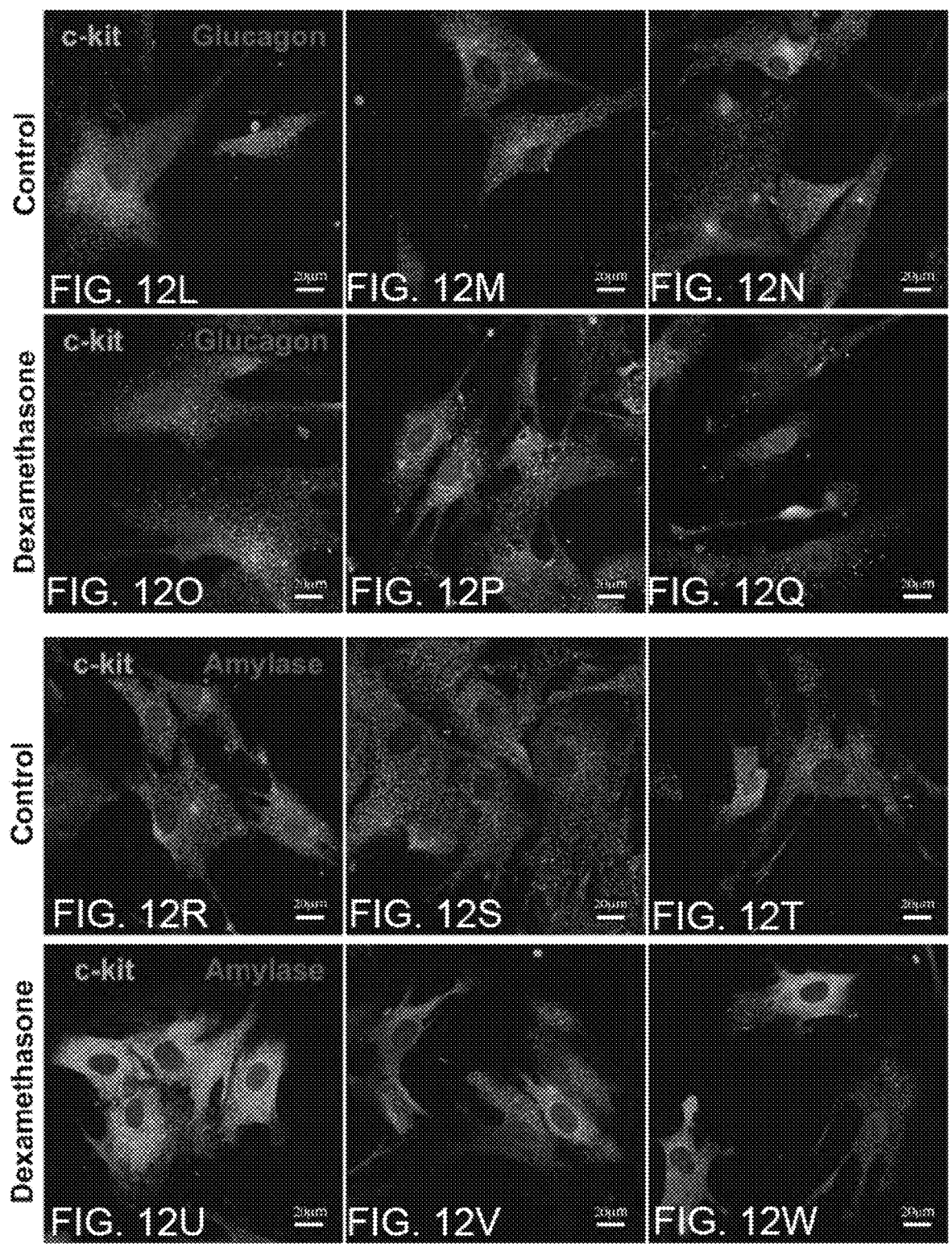
FIG. 12A-FIG. 12K: hPSCs express markers of pancreatic progenitors and commit to the endocrine and exocrine cell phenotypes.

The expression of c-kit in undifferentiated control cells was evident in all cases. In the presence of dexamethasone, the upregulation of the proinsulin C-peptide (FIG. 12E-FIG. 12J) was apparent; the glucose-stimulated insulin secretion (GSIS) protocol, based on the addition of glucose to the medium, led to the synthesis of human insulin, detected by the high sensitivity ELISA assay (FIG. 12K). Moreover, c-kit-positive hPSCs acquired the α-cell phenotype and displayed within the cytoplasm glucagon, or attained the properties of exocrine acinar-cells showing amylase (FIG. 12L-FIG. 12Q and FIG. 12R-FIG. 12W). The dexamethasone protocol, however, was not associated with a complete loss of c-kit expression. Thus, hPSCs have the ability to differentiate into specialized pancreatic cells, consistent with their multi-potentiality.

hPSCs Engraft and Differentiate in the Pancreas of Immunodeficient Mice

To test whether single cell-derived clonal hPSCs have the ability to colonize the pancreas, a cryoinjury was employed as a simplified form of damage in immuno-compromised mice. Shortly thereafter, PKH26- or GFP-positive cells were injected in proximity of the dead tissue (n=6). Histological sections of the cell-treated organs were examined 1-8 days later. This time interval was selected because in other systems stem cell homing occurs in ~24 hours and lineage specification is apparent in a few days (Quesenberry et al., 2005; Rota et al., 2007). Several individual and small groups of labeled hPSCs were detected in the preserved intact tissue (FIG. 13A-FIG. 13E, FIG. 13F, and FIG. 14A-FIG. 14D), while larger pools of tagged-hPSCs were identified within the areas of injury (FIG. 13G-FIG. 13J), indicating that hPSCs were capable of migrating and homing to the non-pathological and pathological portions of the pancreas.

Figures 13G, 13H, 13I, 13J:
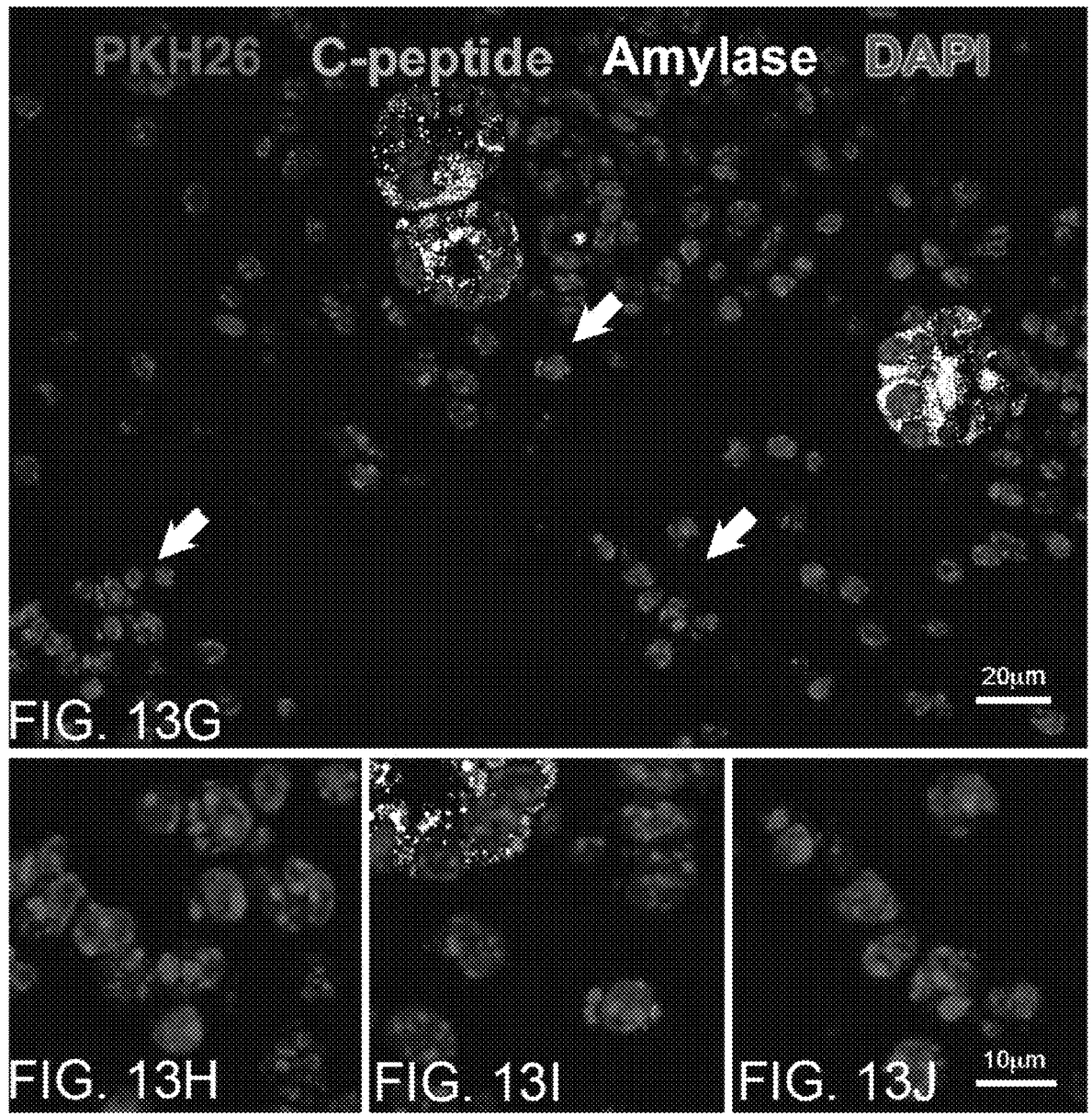
FIG. 13G-FIG. 13J: Clusters of PKH26-labeled hPSCs (red, arrows, FIG. 13G) in an area of damaged mouse pancreas. These hPSCs are negative for C-peptide (green) and amylase (white). These small groups of hPSCs are shown at higher magnification in the insets (FIG. 13H-FIG. 13J).
Figures 13K, 13L, 13M, 13N, 13O, 13P, 13Q:
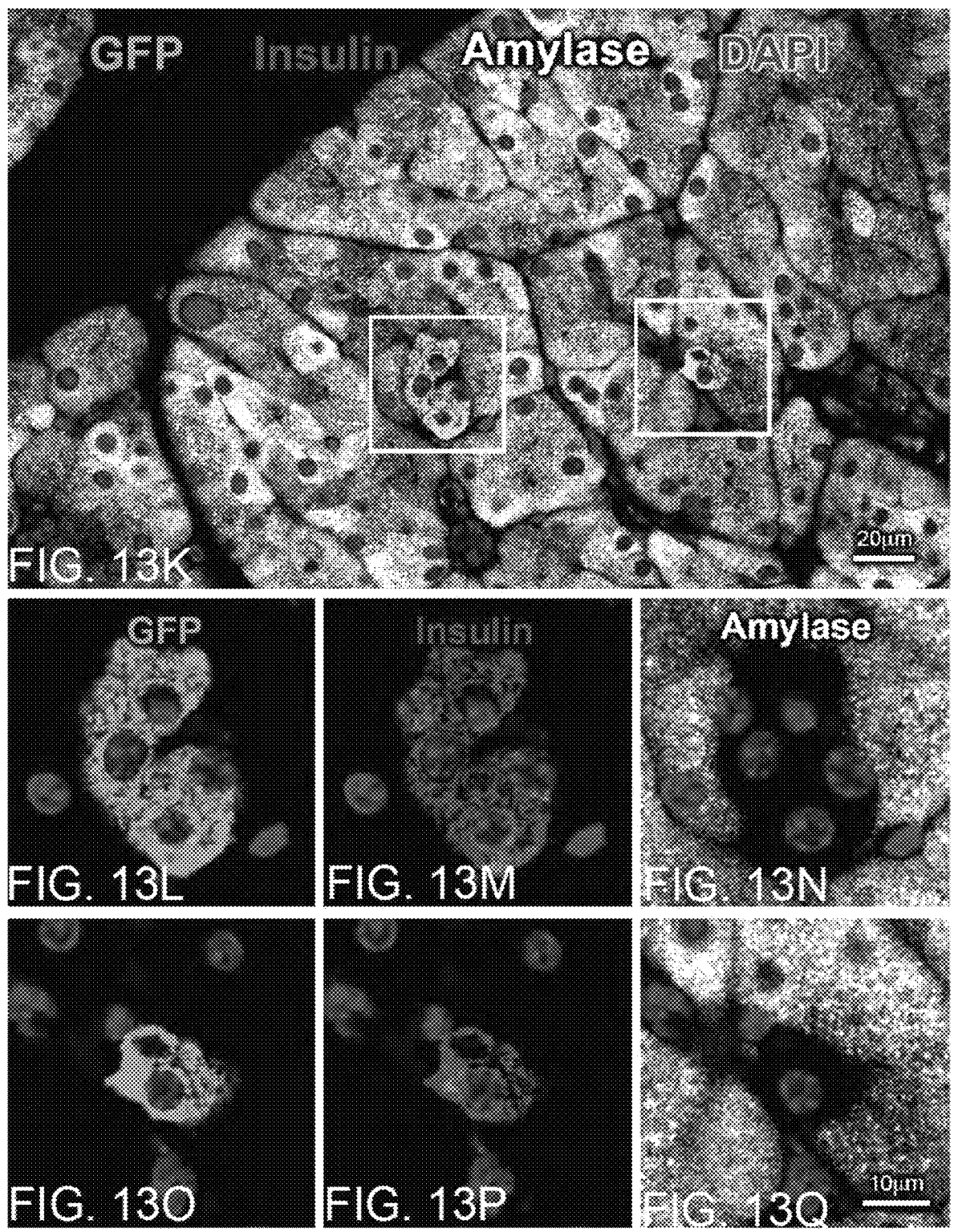
FIG. 13K-FIG. 13Q: Squares define GFP-positive hPSCs in the intact mouse pancreas (amylase, white, FIG. 13K). As illustrated at higher magnification in the insets (FIG. 13L-FIG. 13Q), these hPSCs show the intracellular localization of insulin (red, FIG. 13M and FIG. 13P).
Figures 13A, 13X:
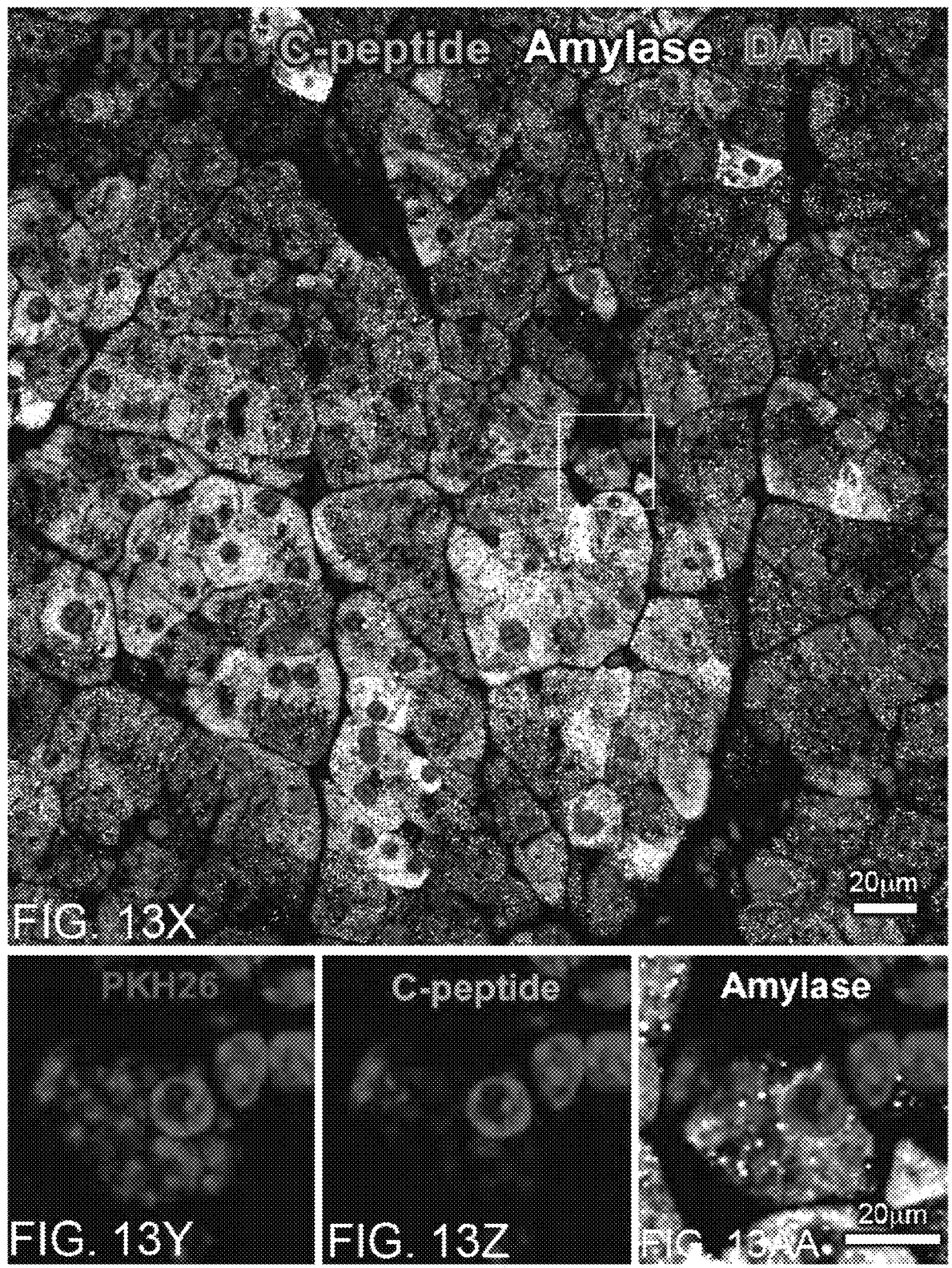
Figures 14A, 14B, 14C, 14D, 14E, 14F, 14G, 14H:
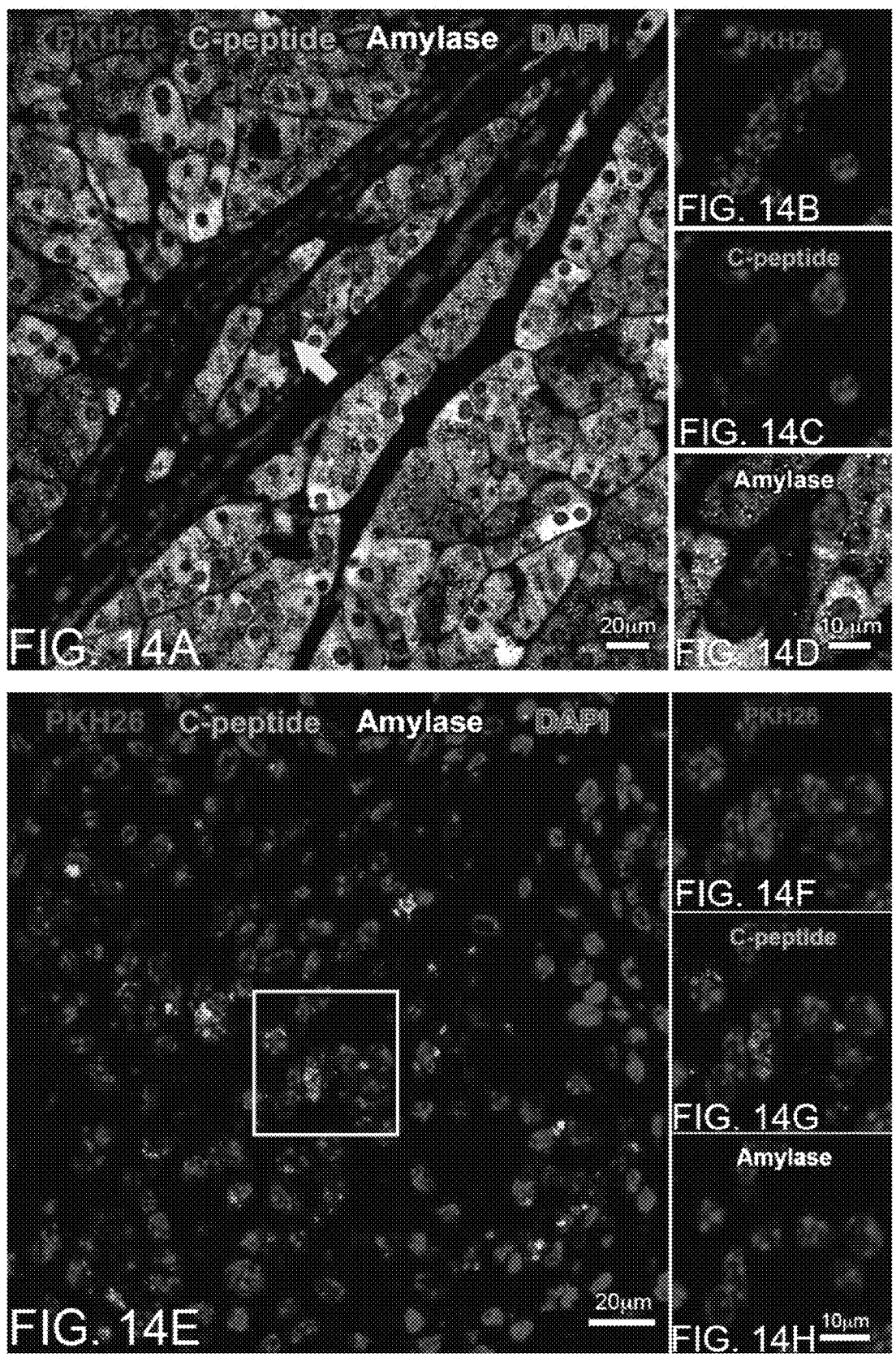
FIG. 14A-FIG. 14H: hPSCs home to the intact and damaged mouse pancreas.
Figures 15A, 15B, 15C, 15D:
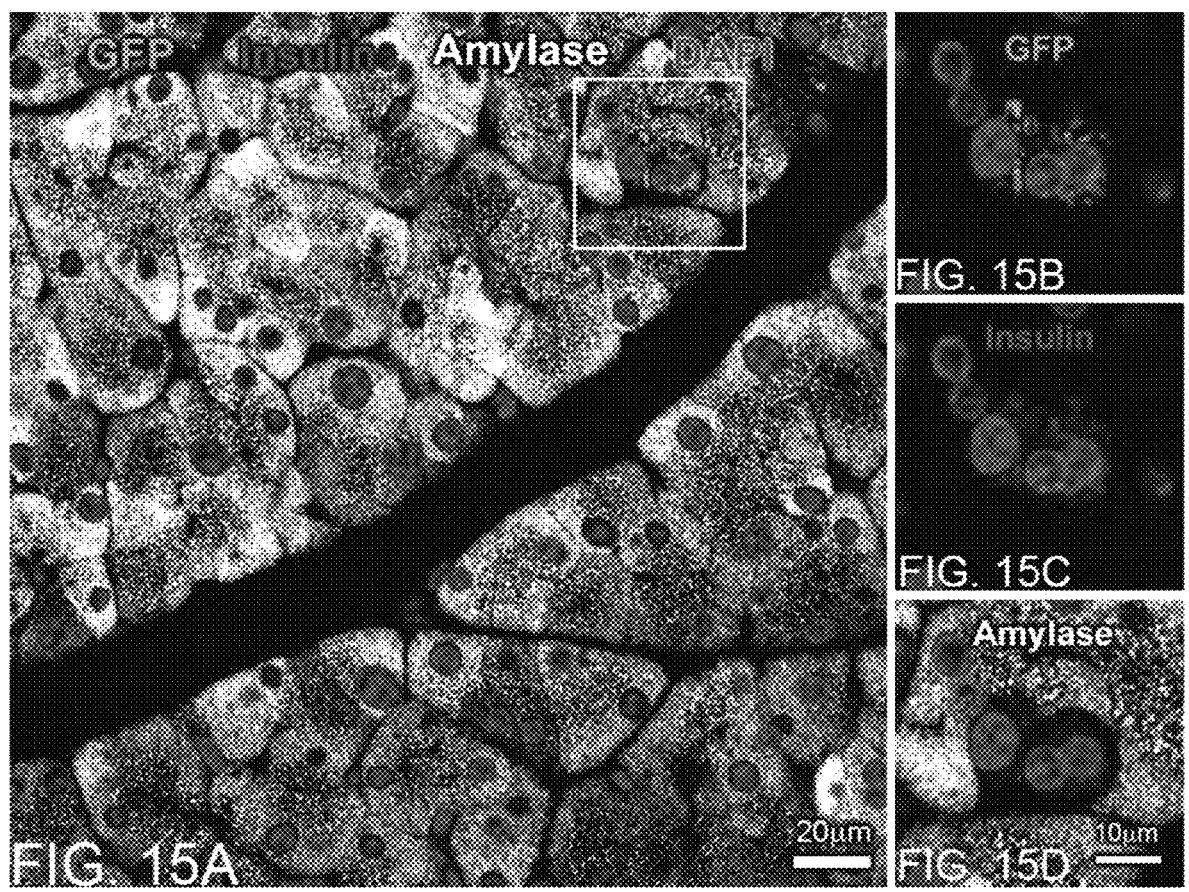
FIG. 15A-FIG. 15D: differentiating hPSCs express insulin. Two GFP-labeled hPSCs (green, FIG. 15B), defined by a square (FIG. 15A), are positive for insulin (red, FIG. 15C). The individual fluorescence channels for GFP (green, FIG. 15B), insulin (red, FIG. 15C) and amylase (white, FIG. 15D) are shown at higher magnification in the insets.

The integration and potential function of the administered hPSCs within the recipient mouse organ was documented by the fate acquisition of the injected cells. Single, small and large clusters of engrafted hPSCs acquired the β-cell phenotype and expressed insulin or C-peptide (FIG. 13K-FIG. 13W, and FIG. 14E-FIG. 14H). Additionally, individual β-cells positive for C-peptide or insulin were scattered throughout the tissue (FIG. 15A-FIG. 15D). The generation of exocrine acinar-cells forming amylase was also observed (FIG. 13X-FIG. 13AA). Clonal hPSCs which retained their original undifferentiated state were distributed in multiple sites of the organ in all 6 animals examined (not shown). Thus, hPSCs propagated in vitro retain their plasticity and can home in vivo to the preserved and injured portions of the pancreas, a finding highly relevant to the future implementation of stem cell therapy in type-1 and type-2 diabetes in humans.

Fate Mapping of c-Kit-Positive Pancreatic Cells Documents their Multipotentiality The recognition of a multipotent hPSC is in contrast with the general interpretation that specialized pancreatic cells derive from self-duplication of preexisting post-mitotic cells which dedifferentiate, reenter the cell cycle and divide (Dor et al., 2004). The possibility that a resident stem cell compartment regulates the homeostasis of the endocrine and exocrine cells of the adult organ has been raised previously (Jiang and Morahan, 2012; Xu et al., 2008).

Although information pointing to a potential role of ductal and differentiated islet cells positive for c-kit in experimental pancreas pathology has been proposed, none of these studies has shown the stem cell properties of these committed cells (Feng et al., 2015). Ligation of the pancreatic duct in the rat is associated with an upregulation of c-kit in duct and islet cells, suggesting their involvement in cell neogenesis (Peters et al., 2005). Similar observations have been made following streptozotocin-induced diabetes (Tiemann et al., 2007) and in a model of pancreatitis in rats (Gong et al., 2012). Based on the data above and these findings in rats, the results in the human pancreas have been complemented with lineage tracing studies in mice. This protocol represents a powerful tool with the potential to unravel the relationship between progenitor cells and their descendants (Kretzschmar and Watt, 2012).

The origin of pancreatic cells was determined first in a transgenic mouse model in which the tamoxifen-inducible mer-Cre-mer protein was targeted to the Kit locus (van Berlo et al., 2014). These mice were cross-bred with an R-GFP reporter line to irreversibly label with GFP any cell that expressed c-kit at the time of tamoxifen administration, i.e., $Kit^{+/MCM} \times$R-GFP mouse. The progeny of the c-kit-positive cells can be recognized by the presence of the fluorescent tag that persists in the cell cytoplasm after the loss of c-kit expression with cell differentiation.

Figures 16I, 16J, 16K, 16L, 16M, 16N, 16O:
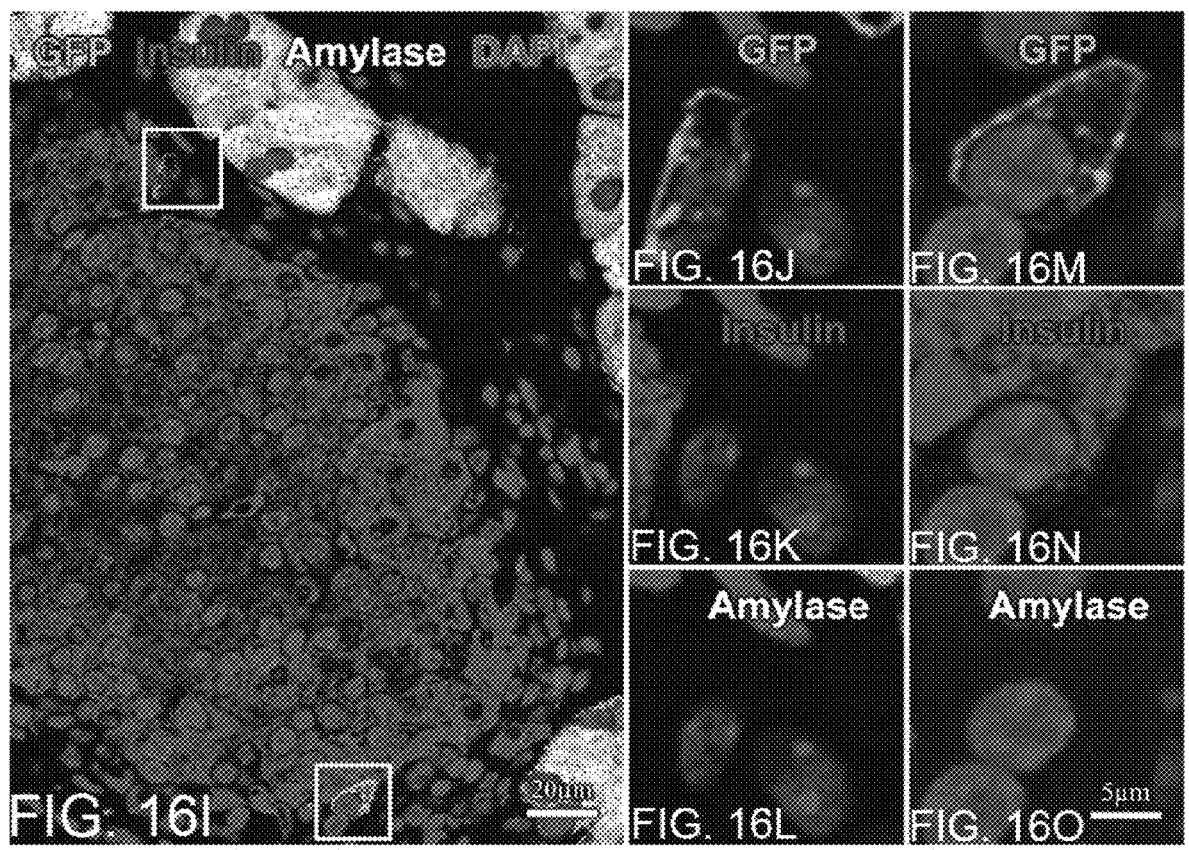
Figure 17:
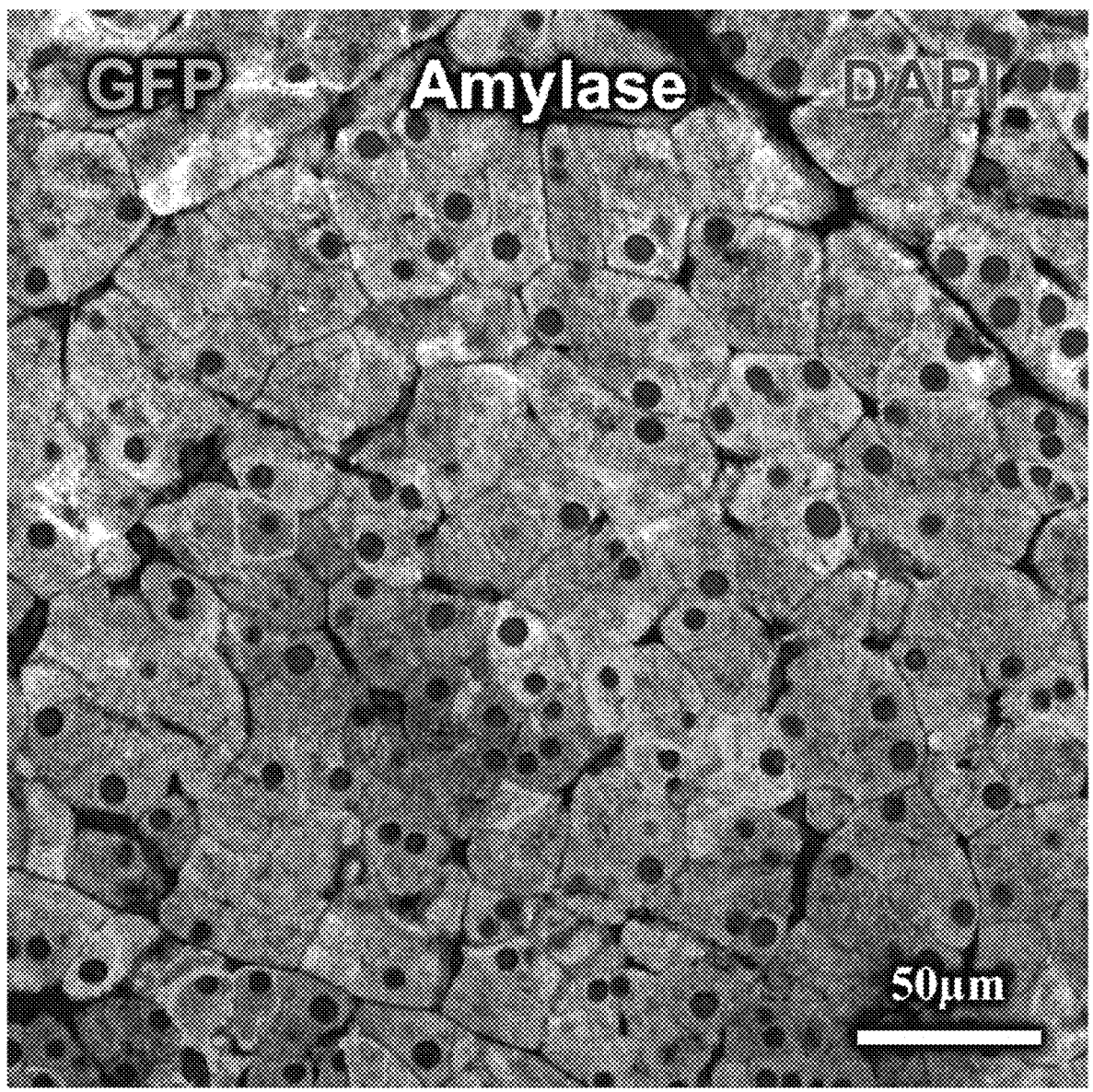
FIG. 17: GFP is expressed in the pancreas of $Kit^{+/MCM} \times mT/mG$ mice. GFP (green) is localized in the plasma membrane of exocrine acinar-cells labeled by amylase (white).
Figure 18A:
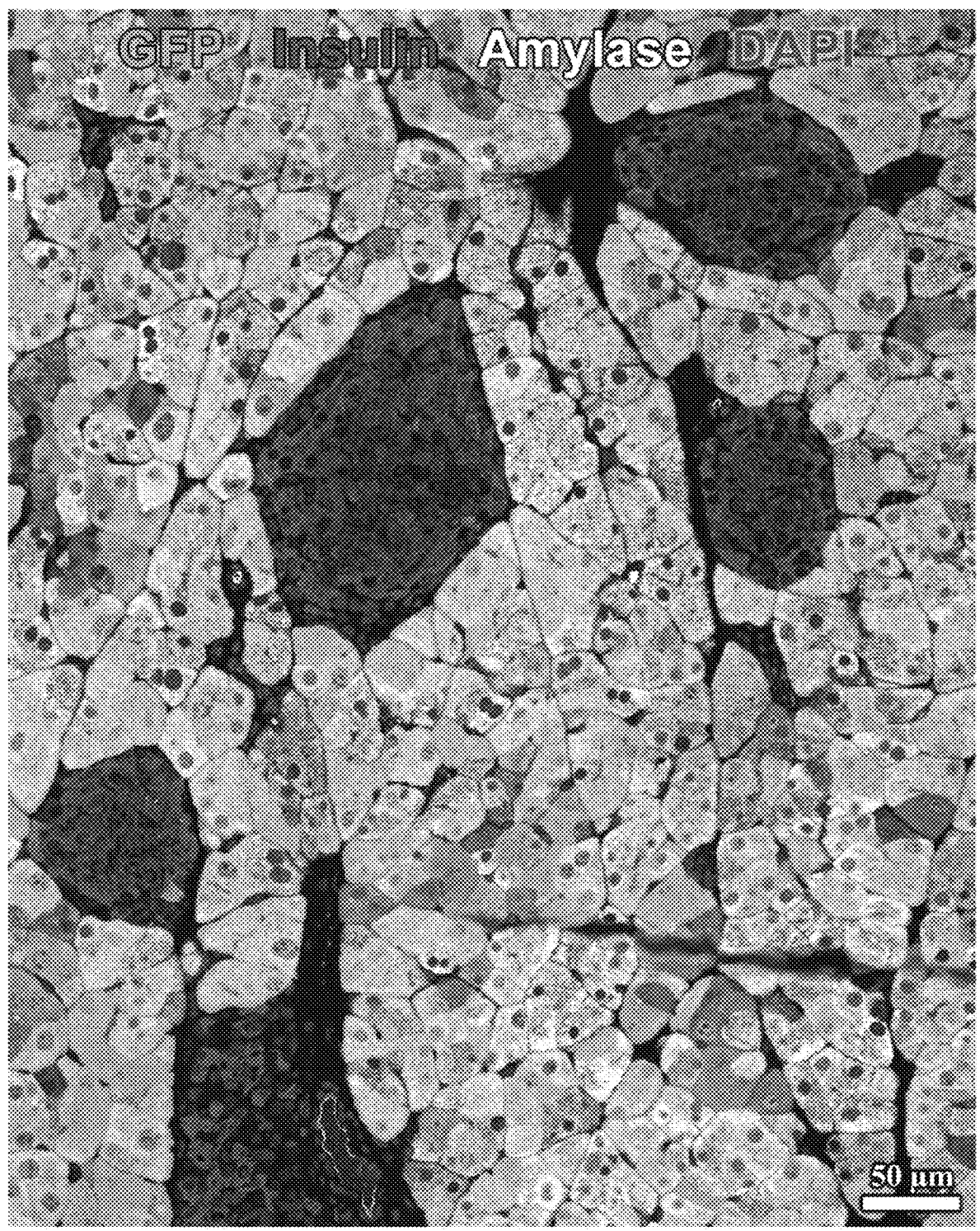
FIG. 18A-FIG. 18HH: $Kit^{CreERT2/+} \times IRG$ mouse: pancreatic cells are the progeny of c-kit-positive cells.
Figures 18B, 18C, 18D, 18E, 18F, 18G, 18H:
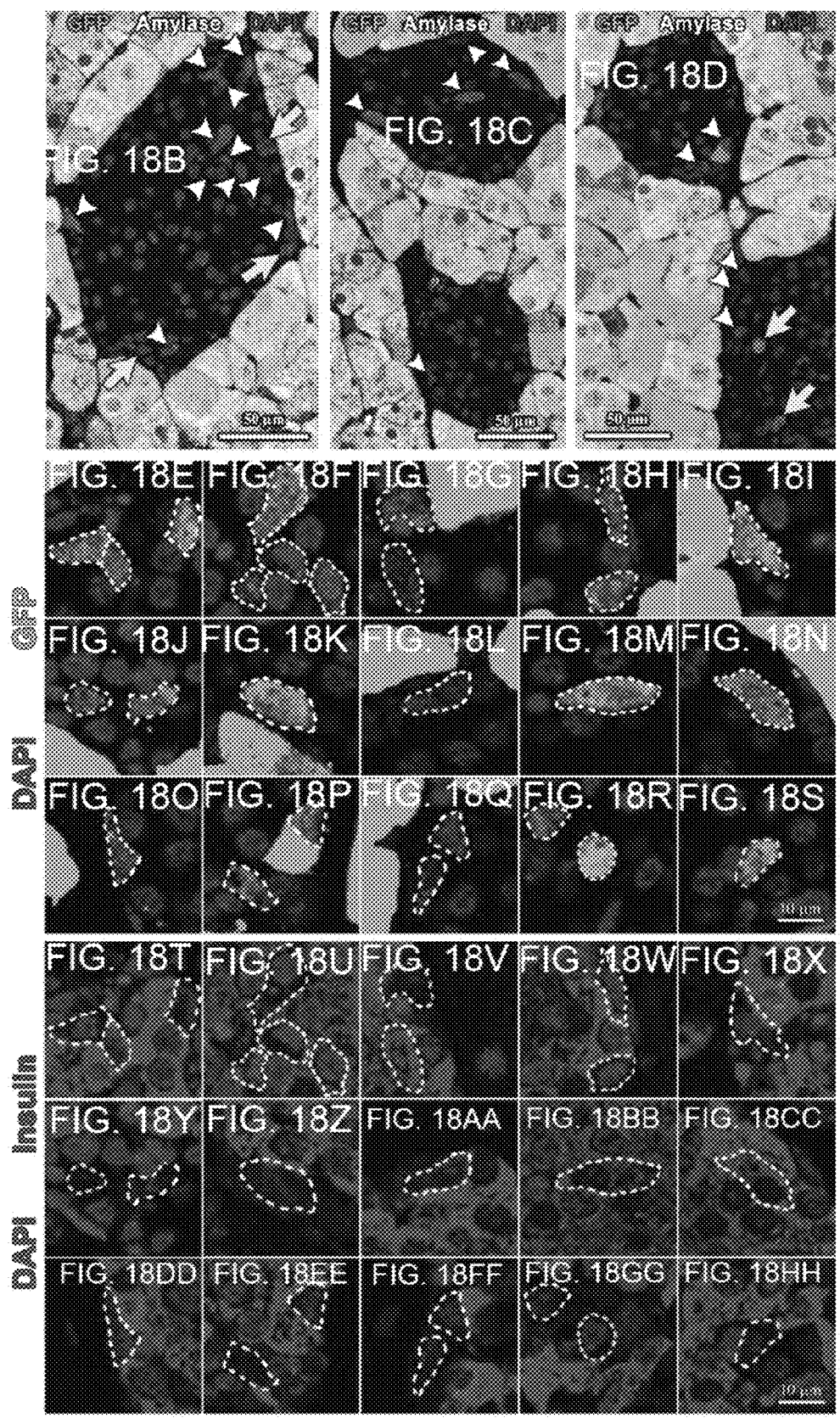

By this genetic strategy, it has been found that after tamoxifen treatment for 6-8 months (n=5), exocrine acinar-cells were intensely positive for GFP (FIG. 16A-FIG. 16C). Moreover, GFP-labeled β-cells were consistently found within the islets of Langerhans (FIG. 16A-FIG. 16C and FIG. 16D-FIG. 16H). A second reporter mouse, mT/mG, was then introduced (Muzumdar et al., 2007). In this dual-color Cre reporter mouse, membrane-targeted tdTomato (mT) is expressed prior to Cre-mediated recombination; the membrane-restricted green fluorescent protein (mG) becomes apparent only after excision of the stop codon. These mT/mG mice were cross-bred with $Kit^{+/MCM}$ animals to generate $Kit^{+/MCM} \times$mT/mG mice. Tamoxifen was injected intraperitoneally daily for 5 days and sacrificed 10 days later (n=6). This protocol was introduced to complement the significantly longer exposure to tamoxifen in the $Kit^{+/MCM} \times$R-GFP mouse. Areas of the pancreas were labeled by GFP; GFP was apparent and limited to the surface of amylase-positive exocrine cells and insulin-positive endocrine β-cells (FIG. 16I-FIG. 16O and FIG. 17).

The insertion of complex constructs in heavily regulated loci such as the c-kit gene can influence the expression of Cre-recombinase. The mer-Cre-mer construct in the $Kit^{+/MCM} \times$R-GFP mouse is in close proximity to one of these regulatory intronic sequences (Cairns et al., 2003; Nadal-Ginard et al, 2014), and this may affect Cre-recombinase. Because of this potential limitation, a second fate mapping model was tested, the $Kit^{CreERT2/+}$ mouse (Goss et al., 2016; Hatzistergos et al., 2015), in which a different region of the c-kit promoter was targeted. The Cre-ERT2 construct was inserted in the first exon of c-kit without affecting the proximal intronic regions (Goss et al., 2016; Hatzistergos et al., 2015). These mice were cross-bred with the two-color IRG reporter line so that, in the absence of Cre-mediated recombination, native red fluorescent protein (DsRed) is expressed in all organs. With tamoxifen administration and Cre-mediated recombination, c-kit-positive cells and their progeny are irreversibly labeled with GFP. Following tamoxifen treatment for 2-3 months (n=4), large regions of the mouse pancreas were positive for GFP, amylase and insulin (FIG. 18A and FIG. 18B-FIG. 18HH), indicating that these specialized cells derived from c-kit-positive cells. Thus, these results in transgenic mice confirm the human data strengthening the notion that c-kit-positive hPSCs are multipotent and may regulate organ homeostasis physiologically.

Native GFP is Co-Expressed with Lineage Specific Pancreatic Cell Proteins

The documentation of distinct intracellular proteins is needed for the identification of different pancreatic cell types and the recognition of whether specialized endocrine and exocrine cells derive from c-kit-positive cells. This information can be obtained following dissection of the organ, enzymatic digestion of the tissue, and fixation and immunolabeling of the isolated cells with specific antibodies. $Kit^{CreERT2/+} \times$IRG mice were exposed to tamoxifen every other week for a period of 6 weeks and the freshly isolated pancreas showed multiple tissue areas labeled by native GFP fluorescence (FIG. 19A-FIG. 19F). Initially, experiments were conducted to determine whether the presence of native GFP was affected by cell fixation and permeabilization. No difference was found in the pool of pancreatic cells positive for native GFP whether untreated or fixed and permeabilized. In both cases, nearly 8-9% of pancreatic cells expressed the reporter gene (FIG. 19G-FIG. 19K).

Figure 19V:
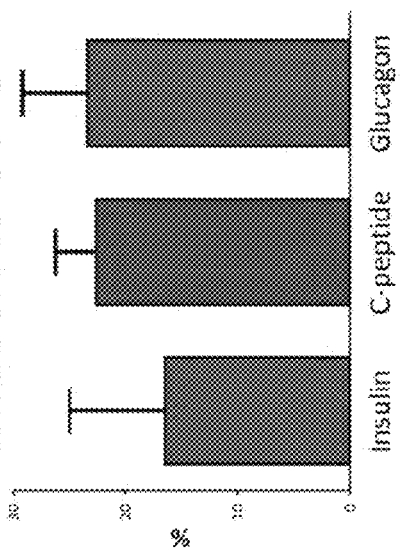
Figure 19H:
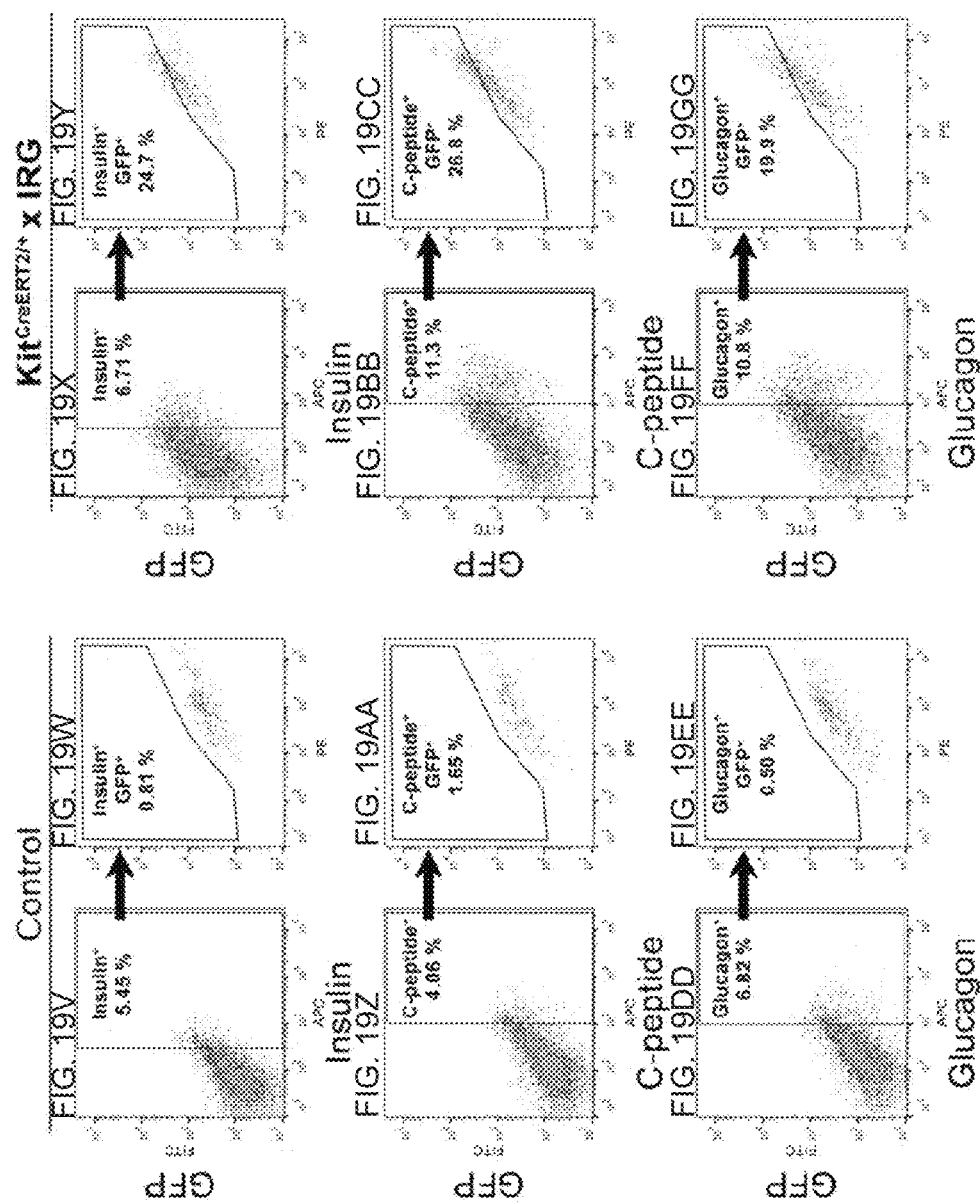

Based on this result, three intracellular proteins were considered, i.e., insulin (n=5), C-peptide (n=2), and glucagon (n=2). Within the entire compartment of isolated pancreatic cells, the percentage of insulin-positive, C-peptide-positive and glucagon-positive cells expressing native GFP comprised 6%, 20% and 14%, respectively (FIG. 19L-FIG. 19U). The significant fraction of non-endocrine cells expressing GFP may reflect mostly the large pool of exocrine cells synthesizing amylase. Subsequently, the frequency of insulin-positive, C-peptide-positive and glucagon-positive cells labeled by native GFP within each of these three cell categories was measured. The fraction of double positive cells was 16%, 23%, and 24% for insulin, C-peptide and glucagon, respectively (FIG. 19V-FIG. 19HH). Thus, the recognition that c-kit-positive cells in the human pancreas are self-renewing, clonogenic and multipotent in vitro, and mouse c-kit-positive cells differentiate in vivo into β-cells, α-cells and exocrine acinar-cells strengthens the notion that the mammalian pancreas is regulated by a class of resident stem cells.

The present disclosure prospects a shift in paradigm of pancreas biology with dramatic clinical implications. The hPSC identified here by the expression of the c-kit receptor is implicated in the growth of β-cells and the synthesis of insulin, α-cells and the generation of glucagon, and acinar cells and the formation of amylase. A series of in vitro and in vivo assays were performed in combination with fate mapping strategies to provide compelling evidence in favor of the recognition and functional role of c-kit-positive cells as bona fide tissue-specific adult stem cells. Thus, the human pancreas is regulated by a resident stem cell compartment which defines it as a self-renewing organ similar to the bone marrow, the skin, the intestine, the lung and the heart.

Over the years, effort has been made to understand the biological processes that lead to β-cell renewal. Self-duplication has been proposed as the process responsible for the expansion of the β-cell compartment physiologically and pathologically (Dor et al., 2004). In this regard, a six-fold increase in β-cell number has been reported in mice from 3 to 12 months of age (Dor et al., 2004). However, the generation of β-cells in the adult human pancreas is apparently extremely limited (Perl et al., 2010), and whether self-duplication actually occurs is open to question; it is difficult to envision how a highly specialized cell with a well-defined function can replicate DNA and divide. This process would involve dedifferentiation of post-mitotic β-cells that acquire a progenitor-like phenotype, reenter the cell cycle and proliferate (Dor and Glaser, 2013; Weinberg et al., 2007). Unfortunately, there are no morphological criteria able to define dedifferentiation of cells in vivo (Leri et al., 2015), challenging this potential source of new β-cells. Similarly, transdifferentiation or reprogramming of pre-existing exocrine cells that attain the ability to synthesize and secrete insulin is controversial (Gomez et al., 2015; Lemper et al., 2015). The hPSC characterized in the present disclosure offers a valid biological foundation for the understanding of the growth adaptation of β-cells with obesity, pregnancy and following partial pancreatectomy.

To prove or disprove that stem cells control β-cell formation in the adult pancreas, a clonal assay of single founder cells is required; stem cells are individual cellular entities characterized by the dual ability to self-renew and differentiate (Hsu and Fuchs, 2012; Leri and Anversa, 2016). Cell population-based studies fall short to define stem cell behavior in terms of clonality, self-renewal, and multipotentiality. This limitation is apparent in lineage tracing studies, in which a specific promoter-driving reporter gene is chosen a priori, introducing an artificial compartmentalization factor (Leri and Anversa, 2016); for example, the use of an insulin promoter will target only cell classes destined to become β-cells (Dor et al., 2004; Xiao et al., 2013), which are distal to undifferentiated, lineage negative stem cells. Moreover, the insulin-positive cell population is highly heterogeneous, including terminally-differentiated cells and cells that have the intermediate immature phenotype of progenitors/precursors. To avoid these confounding variables, the promoter of the stem cell antigen c-kit was targeted in the transgenic mice employed here (Hatzistergos et al., 2015; van Berlo et al., 2014).

A different intensity and distribution of GFP labeling in the exocrine and endocrine compartments of the pancreas was observed in these two transgenic mice, originally developed to determine the role of the c-kit receptor in the heart, intestine and mast cells (Hatzistergos et al., 2015; Heger et al., 2014; Klein et al., 2013; van Berlo et al., 2014). However, the GFP signal in endocrine and exocrine acinar-cells was stronger and more diffuse in the $Kit^{+/MCM} \times R\text{-}GFP$ mouse than in the $Kit^{CreERT2/+} \times IRG$ mouse. Moreover, in the $Kit^{CreERT2/+} \times IRG$ mouse, GFP labeling was more apparent in exocrine acinar-cells than in endocrine cells. This variability in the expression of the reporter protein cannot be explained easily.

The knock-in construct utilized in the generation of these genetic models (Hatzistergos et al., 2015; van Berlo et al., 2014) leads to the deletion of one of the c-kit alleles. The decrease in the expression of c-kit in PSCs may have affected more the endocrine than the exocrine component of the tissue, resulting in less intensively labeled GFP-positive β-cells than acinar cells. An analogous phenomenon has been observed in the heart where GFP has been found to be more prominent in endothelial cells than in cardiomyocytes (van Berlo et al., 2014), or in cardiomyocytes more than in vascular cells (Hatzistergos et al., 2015). The disruption of the c-kit locus in knock-in mice promotes phenotypical alterations similar to those observed in c-kit mutant mice (Geissler et al., 1988). In fact, all mice showed a white belly spot and had severe atrophy of the testis (FIG. 20A-FIG. 20B), both indicative of alterations in c-kit function as a result of Cre knock-in at the c-kit locus (Hatzistergos et al., 2015; Nadal-Ginard et al., 2014). The critical role of c-kit in the homeostatic control of the pancreas is consistent with the abnormalities present in some c-kit mutant mice in which the partial loss of receptor tyrosine kinase activity is coupled with defective insulin secretion, decreased β-cell mass, attenuated β-cell proliferation and the manifestations of a diabetic phenotype (Krishnamurthy et al., 2007).

The molecular identity of hPSCs in the adult organ mimics that of embryonic pancreatic progenitors during their transition to functional endocrine and exocrine cells. The gene regulatory network of embryonic progenitors involves the sequential activation and repression of transcription factors, typically found in precursor cells with increasingly restricted developmental options. The expression of c-kit has been found to be associated with Pdx1 and Sox9, two transcription factors that identify multipotent progenitors (Seymour, 2014). Additionally, the endocrine and exocrine fate determinants, Pdx1, Sox9 and Ngn3 are poised for expression in c-kit-positive hPSCs providing important evidence in favor of their plasticity and multipotentiality.

The transcriptional profile of clonal c-kit-positive hPSCs defined by qRT-PCR and NanoString® was complemented with the evaluation of the protein expression typical of pancreatic specialized cells. The detection of C-peptide, insulin, glucagon and amylase in differentiating hPSCs offers rather compelling proof that c-kit recognizes a compartment of resident primitive cells that regulate the renewal of pancreatic cells and may contribute to tissue repair following injury.

The old concept that cells with the properties of β-cells do not share a functional identity has been revisited recently (Dorrell et al., 2016). Four antigenically distinct β-cell subsets with diverse gene expression profile and response to glucose have been found in human islets (Bonner-Weir and Aguayo-Mazzucato, 2016; Dorrell et al., 2016). The contribution of each cell subset to the whole compartment of β-cells remains constant in healthy human islets but is highly variable with diabetes resulting in an increase in the proportion of β-cells less sensitive to glucose stimulation (Dorrell et al., 2016). In vivo analysis of the dynamics of β-cells has revealed that a restricted pool of β-cells actively proliferate during pregnancy leading to an increase in the mass of mature β-cells (Bader et al., 2016). Whether functionally distinct β-cells correspond to independent cell lineages or constitute interdependent entities remains to be defined (Bonner-Weir and Aguayo-Mazzucato, 2016). The co-existence of proliferating and post-mitotic β-cells suggests that the pancreas might be a hierarchically structured system (Smukler et al., 2011) in which differentiating stem cells progressively acquire the committed state and undergo maturation into amplifying dividing cells, which eventually reach terminal differentiation and growth arrest.

The unfavorable evolution of type-1 diabetes in humans correlates with the progressive loss of β-cells, while modest residual insulin secretion provides clinical benefits consisting of an improved glycemic control and a reduction in systemic complications (Oram et al., 2014; Sherr et al., 2014). Importantly, persistent insulin production and secretion has been documented in a large cohort of patients with a history of type-1 diabetes of 50 years or longer (Keenan et al., 2010). Intact non-apoptotic β-cells have been identified histologically in all pancreatic samples collected post-mortem from 9 diabetic subjects originally enrolled in the Joslin Medalist study (Keenan et al., 2010). Despite the long-term negative effects of diabetes, some β-cell function was maintained, suggesting that a pool of hPSCs may be involved in the replenishment of β-cells during the evolution of the disease.

A similar correlation between β-cell deterioration and severity of peripheral vasculopathy, neuropathy, nephropathy and cardiomyopathy has been found in type-2 diabetes (Boudina and Abel, 2007; Wajchenberg, 2007; Yagihashi et al., 2016). Decreases in the circulating level of C-peptide are proportional to the degree of vascular defects with loss in endothelial-dependent vasodilatation (Hadi and Suwaidi, 2007). Conversely, a more effective insulin secretion tends to preserve metabolic control and attenuate chronic complications (Saisho, 2014). These clinical findings emphasize the relevance to restore (3-cell mass and function in type-2 diabetes.

In conclusion, the human pancreas possesses a compartment of resident stem cells that differentiate in vitro and, equally important, in vivo into β-cells synthesizing insulin. Despite the presence of type-1 and type-2 diabetes, a pool of intact hPSCs may persist within the organ, and biopsy samples can be collected for stem cell isolation and amplification. The in vitro propagated hPSCs can be delivered back to the patient and, as demonstrated here experimentally, can engraft and acquire the β-cell phenotype, reconstituting the stem cell compartment and the β-cell mass; stem cell therapy may correct the diabetic state and interfere with its systemic consequences.

Human Pancreatic Samples

Twenty-nine specimens of normally appearing tissue discarded at surgery were included in the study. Samples were divided in two parts. One part was fixed in 10% formalin and embedded in paraffin to obtain sections, 4-6 μm in thickness, for immunolabeling and confocal microscopy. The other part of fresh tissue was washed in PBS and minced into small pieces for subsequent digestion. In some cases, a portion of the samples was frozen.

Immunolabeling and Confocal Microscopy of Human Pancreas

Tissue sections from the pancreatic samples were labeled overnight at 4° C. with rabbit polyclonal anti-human c-kit (1:100; Dako®) and mouse monoclonal anti-human tryptase (1:100; Abcam®), or goat polyclonal anti-human tryptase (1:100; R&D) to distinguish putative human pancreatic stem cells (hPSCs) from mast-cells (Sanada et al., 2014). Nuclei were stained by DAPI (Sigma). The number of c-kit-positive cells, and the number of c-kit-positive tryptase-negative putative hPSCs and c-kit-positive tryptase-positive mast-cells were measured quantitatively in six randomly chosen samples (n=6) (Anversa & Olivetti, 2002; Sanada et al., 2014). These parameters were collected by evaluating in tissue sections the number of nuclei pertaining to each of the three cell classes, together with the number of nuclei present in the other pancreatic cell populations. The lineage commitment of putative hPSCs was determined by co-labeling with mouse monoclonal anti-human C-peptide (1:100; Abcam®), mouse monoclonal or guinea pig polyclonal anti-human insulin (1:100; Abcam®), mouse monoclonal anti-human glucagon (1:100; Abcam®), mouse monoclonal or rabbit monoclonal anti-human amylase (1:100; Santa Cruz or Cell Signaling), and mouse monoclonal anti-human cytokeratin-19 (1:100; Dako®). The incubation time was in all cases, one hour at 37° C. Secondary antibodies carrying fluorescent proteins were employed. Images were collected with the Olympus® FV1000 confocal laser scanning microscope. During image acquisition the setting of all parameters were maintained constant.

Isolation and Expansion of Pancreatic Cells In Vitro

Tissue fragments were enzymatically dissociated at 37° C. in Ham's F12 medium (Lonza®) containing 25 μg/ml Liberase™ TL (Roche™) and 0.02% DNAse I (Sigma). The isolated unfractionated cells were then washed in medium containing fetal bovine serum (FBS) and subsequently plated on laminin-coated dishes (Invitrogen™). Cells were cultured in Ham's F12 medium supplemented with 10% FBS (HyClone®), 5 mU/ml recombinant human erythropoietin (Sigma), 10 ng/ml recombinant human fibroblast growth factor-basic (FGF-B) (Peprotech®), 1% penicillin-streptomycin (Sigma) and 0.2 mM L-Glutathione (Sigma) (Beltrami et al., 2003; Bearzi et al., 2007). The growth medium was changed every 2-3 days. At approximately 80% confluence, cells were dissociated using Accutase® (Innovative Cell Technologies) and passaged. This protocol was applied to 16 samples (n=16).

Flow-Cytometry and Sorting of Human Pancreatic Cells

The expanded pancreatic cells were immunolabeled and sorted for c-kit. To enhance the specificity of the process and avoid unspecific binding, two antibodies recognizing two distinct epitopes of the c-kit receptor (CD117) were utilized: APC-conjugated mouse anti-human CD117 (1:100; BD-Biosciences) and PE-conjugated mouse anti-human CD117 (1:100; Miltenyi Biotec®). APC-conjugated and PE-conjugated mouse IgG isotype controls (1:100) for the two antibodies were used (Liu et al., 2015). The labeling reaction was conducted at 4° C. Staining with DAPI was added to exclude dead cells from the analysis. Only cells positive for the two c-kit epitopes were sorted (BD FACSAria™ II; BD-Biosciences), plated and studied 1-3 days later. For immunolabeling of the sorted and plated cells a third c-kit antibody was used (1:100; Dako®).

Symmetric and Asymmetric Cell Division

The modality of cell division was determined by labeling sorted and plated cells, for c-kit (see above) and α-adaptin (n=5). For α-adaptin, a mouse monoclonal anti-human (1:100; Santa Cruz) was employed (Ferreira-Martins et al., 2012); the reaction was performed at 37° C. for one hour. Nuclei were stained by DAPI. The uniform and non-uniform localization of α-adaptin was evaluated together with c-kit to distinguish symmetric and asymmetric stem cell division, respectively.

Clonal Assay

FACS-sorted c-kit-positive cells from 14 patients were seeded individually in single wells of 96-well-plates (n=14). Over a period of 2-3 weeks, multicellular clones were obtained (Bearzi et al., 2007; Beltrami et al., 2003; Liu et al., 2015). Clonal efficiency was measured by identifying the presence of cell clusters with a phase contrast microscope and following fixation and staining with 5% Methylene Blue (Sigma) dissolved in ethanol. Clonal cells were amplified and employed for molecular assays, including qRT-PCR and Nanostring® methodology.

Quantitative RT-PCR

Total RNA was extracted with TRIzol™ from clonal hPSC preparations (n=4) for the detection of transcripts of c-kit, Pdx1, Sox9, Ngn3 and Nkx6.1. cDNA was generated from 1 µg of total RNA incubated with oligo(dT)15 primers for 2 hours at 37° C. and then diluted 1:10. RT-PCR was performed on StepOnePlus® Real Time PCR Systems (Applied Biosystems) using 1/200th of the cDNA per reaction. Cycling conditions were as follows: 95° C. for 10 minutes followed by 35 cycles of amplification (95° C. denaturation for 15 seconds, and 60° C. combined annealing/extension for 1 minute). Human-specific primers (see below) were downloaded from the NIH primer database qPrimerDepot or were designed with the Vector NTI software (Invitrogen™). Quantified values were normalized against the input determined by the housekeeping gene β2-microglobulin. PCR products were run on 2% agarose/1×TBE gel and DNA bands with the expected molecular size were obtained.

Nanostring® Protocol

The expression of a panel of 194 stem cell-related genes was evaluated in hPSC clones (n=3). Cells cultured in the absence or presence of 10-8 M dexamethasone (Sigma) for a period of one week were analyzed. All procedures related to mRNA quantification, including sample preparation, hybridization, detection, and scanning were carried out as recommended by NanoString Technologies® (Geiss et al., 2008; Talhouk et al., 2016; Veldman-Jones et al., 2015).

Briefly, total RNA was extracted from hPSCs using the Trizol™ method (Invitrogen™) according to the manufacturer's instructions. RNA concentration was measured using a Nanodrop® 1000 instrument (ThermoFisher Scientific™). The probe sets for each gene contained in the nCounter® Stem Cell Codeset were designed and synthesized at NanoString Technologies®. Internal reference genes and three housekeeping genes (ACTB, GAPDH and LDHA) were included in the CodeSet for normalization purposes. The code set contained a 3' biotinylated capture probe, a 5' reporter probe tagged with a fluorescent barcode and two sequence-specific probes for each of the 194 transcripts. Probes were hybridized to 100 ng of total RNA for 16 hours at 65° C., after which the excess capture and reporter probes were removed and transcript-specific ternary complexes were immobilized on a streptavidin-coated cartridge.

Data collection was carried out with the nCounter® Digital Analyzer to count individual fluorescent barcodes and quantify target RNA molecules present in each sample. Raw NanoString® counts for each gene within each experiment were subjected to technical normalization using the counts obtained for the positive control probes. Subsequently, a biological normalization was done using the three housekeeping genes included in the panel. Normalized data were log 2-transformed. All mRNAs which had fewer than mean background±2 standard deviations were considered to be below the limits of detection. Paired t-test was utilized to identify differentially expressed genes in untreated clonal hPSCs and the corresponding dexamethasone-treated clonal hPSCs. Results were expressed as percent difference with respect to untreated clonal hPSCs and were represented as a heat-map.

Differentiation of c-Kit-Positive Cells c-kit-positive cells from distinct preparations were treated with $10^{-8}$ M dexamethasone (Sigma) for one week to induce lineage commitment (n=4). Cells were then fixed with 4% paraformaldehyde, blocked in 10% donkey serum and co-stained for c-kit and C-peptide, amylase or glucagon. The following experimental conditions were implemented: rabbit polyclonal anti-human c-kit (Dako®) at a concentration of 1:100, overnight at 4° C.; mouse monoclonal anti-human C-peptide (Abcam®) at a concentration of 1:100, for one hour at 37° C.; mouse monoclonal anti-human glucagon (Abcam®) at a concentration of 1:100, for one hour at 37° C.; and mouse monoclonal anti-human amylase (Santa Cruz) at a concentration of 1:100, for one hour at 37° C. The expression of c-kit and lineage markers was determined by confocal microscopy.

Glucose Stimulated Insulin Secretion (GSIS)

Clonal c-kit-positive hPSCs cultured in individual wells were washed with $Ca^{2+}$ and $Mg^{2+}$ free PBS and then starved for 1 hour in Krebs-Ringer buffer (KRB) containing 0.1% BSA and 2.8-3.3 mM glucose for 1 hour at 37° C. For glucose stimulation, cells were transferred to fresh KRB supplemented with 0.1% BSA and 16.7 mM glucose for 1 hour at 37° C. Cells were then washed with PBS and treated with 500 µl acid-ethanol. Cells were scraped from the wells, collected in Eppendorf Tubes® and sonicated for 1 minute. Cells were kept overnight at 4° C. to complete the lysis process. Lysates were centrifuged at 7000 rpm for 10 minutes at 4° C. and supernatants analyzed by the high sensitive human insulin-specific ELISA assay. Pellets were further concentrated with SpeedVac® (Thermo Scientifics) and re-suspended for the collection of DNA. The concentration of DNA was measured by Nanodrop®. Insulin values were normalized for DNA content (Dirice et al., 2014).

Injury of the Pancreas

Animals received humane care in compliance with the Guide for the Care and Use of Laboratory Animals as described by the Institute of Laboratory Animal Research Resources, Commission on Life Sciences, National Research Council. Under isoflurane (1.5%) anesthesia, the abdomen of NOD-Scid mice (n=6) was opened and a cryoinjury, 3 mm³ in volume, was induced in the pancreas with a stainless steel probe pre-cooled in liquid nitrogen. The area of damage was identified by the pale color of the affected tissue. Shortly thereafter, 3-4 injections of clonal hPSCs infected with a lentivirus carrying GFP (Hosoda et al., 2009) or labeled with PKH26 dye (Liu et al., 2015), were administered in the region adjacent to the damaged parenchyma. The injected clonal hPSCs were at most 200,000. Animals were euthanized by isoflurane overdose and dissection of the heart 1-8 days later. The pancreas was fixed with 10% phosphate-buffered formalin and embedded in paraffin.

Lineage Tracing

Two distinct c-kit knock-in mouse lines were studied: $Kit^{+/MCM}$ and $Kit^{CreERT2/+}$ mice (Hatzistergos et al., 2015; Goss et al., 2016; van Berlo et al., 2014). $Kit^{+/MCM}$ mice were bred to LoxP site-dependent Rosa26-CAG-loxP-STOP-loxP-eGFP (R-GFP) reporter mice to irreversibly label with GFP any cell that expressed c-kit at the time of tamoxifen administration (van Berlo et al., 2014).

$Kit^{+/MCM}$×R-GFP mice were fed with 200-400 mg/kg tamoxifen for a period of 6-8 months (n=5). Wild-type mice and mice not exposed to Tamoxifen were used as controls (n=2). Additionally, a second reporter mouse, mT/mG, was introduced (Muzumdar et al., 2007). In this double-fluorescent Cre reporter mouse, membrane-targeted tandem dimer Tomato (mT) is expressed prior to Cre-mediated recombination, while the membrane-targeted green fluorescent protein (mG) is expressed after excision of the stop codon, i.e., $Kit^{+/MCM}$×mT/mG. The $Kit^{+/MCM}$×mT/mG mice (n=6); these mice were injected i.p. daily for 5 days with tamoxifen, 2 mg/kg b.w., and sacrificed 10 days later.

To confirm the results obtained with the $Kit^{+/MCM}$ mouse, we studied another c-kit knock-in mouse, in which a different region of the c-kit promoter was targeted i.e., the $Kit^{CreERT2}$ mouse line. The $Kit^{CreERT2/+}$ mice were crossbred with the two-color IRG reporter line (De Gasperis et al., 2008; Goss et al., 2016; Hatzistergos et al., 2015) so that, in the absence of Cre-mediated recombination, native red fluorescent protein (DsRed) is expressed in all organs. $Kit^{CreERT2/+}$×IRG mice were treated with tamoxifen, 400 mg/kg, for 2-3 months (n=3). The $Kit^{+/MCM}$×R-GFP, $Kit^{+/MCM}$×mT/mG, and $Kit^{CreERT2/+}$×IRG mice were used for histology and immunolabeling and confocal microscopy. For the analysis of pancreatic cells by flow cytometry (Liu et al., 2015; Sanada et al., 2014), $Kit^{CreERT2/+}$×IRG mice were fed with tamoxifen, 200 mg/kg every other week for a period of 6 weeks, prior to cell isolation and characterization; for insulin n=5, and for C-peptide and glucagon n=2.

Immunolabeling and Confocal Microscopy of Mouse Pancreas

After deparaffinization and rehydration, tissue sections were blocked with 10% normal donkey serum (Jackson Immuno Research) in PBS for 30 minutes and incubated overnight at 4° C. or for 2 hours at 37° C. with goat polyclonal anti-GFP (1:40; Molecular Probes®). Mouse monoclonal anti-insulin (Abeam®) or guinea pig anti-insulin (Abcam®), and rabbit monoclonal anti-amylase (Cell Signaling) diluted 1:100 in PBS were utilized to label β-cells and acinar cells, respectively. After washing with PBS, tissue sections were exposed for 1 hour at 37° C. to FITC- or TRITC-conjugated secondary antibodies (Jackson Immuno Research) diluted 1:100 in PBS. To avoid the autofluorescence of paraffin-embedded formalin-fixed tissue sections, slides were treated with 1% Sudan Black in 70% ethanol for 30 minutes. Sections were mounted with Vectashield® hard set mounting medium (Vector® Labs).

Images were acquired with Olympus® FV1000 and Nikon™ C2plus confocal laser scanning microscopes. During image acquisition the setting of all parameters were maintained constant.

Flow-Cytometry of Mouse Pancreatic Cells

The freshly dissected pancreas was photographed, and the tissue was enzymatically dissociated to obtain pancreatic cells as described above for human samples. Initially, the percentage of live, unfixed pancreatic cells expressing native GFP fluorescence was determined, together with the fraction of immunolabeled fixed GFP-positive cells (FITC-conjugated rabbit polyclonal anti-GFP; 1:100). In the latter case, cells were washed in PBS and fixed at room temperature for 30 minutes with fixation buffer containing 2% formaldehyde (eBioscience®). Cells were then permeabilized with permeabilization buffer (eBioscience®) and blocked with donkey serum. For the characterization of β-cells and α-cells, cell suspensions were pre-incubated with rat IgG2b anti-mouse CD16/CD32 monoclonal antibody (BD Bioscience) at room temperature for 15 minutes prior to staining with specific antibodies or isotype-matched control antibodies. Cells were incubated with primary antibodies at room temperature for 30 minutes: rabbit polyclonal anti-GFP (1:100; Invitrogen™), guinea pig polyclonal anti-insulin (1:200; Abcam®), mouse monoclonal anti-C-peptide (1:200; Abcam®), and mouse monoclonal anti-glucagon (1:200; Abcam®). Stained cells were washed with PBS, exposed to secondary antibodies conjugated with Alexa Fluor® 488 (GFP) or with Alexa Fluor® 647 (lineage markers) and analyzed using a BD FACSCanto™ II. At least 10,000 events were collected and data were analyzed using FlowJo® software (Liu et al., 2015; Sanada et al., 2014).

Statistical Analysis

Data are shown as mean±SD. Statistical differences were evaluated by Student's t test; p<0.05 was considered significant (McDonald, 2014).

REFERENCES

Arda, H. E., Benitez, C. M., and Kim, S. K. (2013). Gene regulatory networks governing pancreas development. Dev. Cell 25, 5-13.

Bader, E., Migliorini, A., Gegg, M., Moruzzi, N., Gerdes, J., Roscioni, S. S., Bakhti, M., Brandi, E., Irmler, M., Beckers, J., et al. (2016). Identification of proliferative and mature β-cells in the islets of Langerhans. Nature 535, 430-434.

Beltrami, A. P., Barlucchi, L., Torella, D., Baker, M., Limana, F., Chimenti, S., Kasahara, H., Rota, M., Musso, E., Urbanek, K., et al. (2003). Adult cardiac stem cells are multipotent and support myocardial regeneration. Cell 114, 763-776.

Bonner-Weir, S., and Aguayo-Mazzucato, C. (2016). Physiology: pancreatic β-cell heterogeneity revisited. Nature 535, 365-366.

Boudina, S., and Abel, E. D. (2007). Diabetic cardiomyopathy revisited. Circulation 115, 3213-3223.

Brown, M. L., and Schneyer, A. L. (2010). Emerging roles for the TGFbeta family in pancreatic beta-cell homeostasis. Trends Endocrinol. Metab. 21, 441-448.

Cairns, L. A., Moroni, E., Levantini, E., Giorgetti, A., Klinger, F. G., Ronzoni, S., Tatangelo, L., Tiveron, C., De Felici, M., Dolci, S., et al. (2003). Kit regulatory elements required for expression in developing hematopoietic and germ cell lineages. Blood 102, 3954-3962.

Dirice, E., Kahraman, S., Jiang, W., El Ouaamari, A., De Jesus, D. F., Teo, A. K., Hu, J., Kawamori, D., Gaglia, J.

L., Mathis, D., et al. (2014). Soluble factors secreted by T cells promote β-cell proliferation. Diabetes 63, 188-202.

Dor, Y, Brown, J., Martinez, O. I., and Melton, D. A. (2004). Adult pancreatic beta-cells are formed by self-duplication rather than stem-cell differentiation. Nature 429, 1-6.

Dor, Y., and Glaser, B. (2013). β-cell dedifferentiation and type 2 diabetes. N. Engl. J. Med. 368, 572-573.

Dorrell, C., Schug, J., Canaday, P. S., Russ, H. A., Tarlow, B. D., Grompe, M. T., Horton, T., Hebrok, M., Streeter, P. R., and Kaestner K. H. (2016). Human islets contain four distinct subtypes of β cells. Nat. Commun. 7, 11756.

Ellison, G. M., Vicinanza, C., Smith, A. J., Aquila, I., Leone, A., Waring, C. D., Henning, B. J., Stirparo, G. G., Papait, R., Scarfò, M., et al. (2013). Adult c-kit(pos) cardiac stem cells are necessary and sufficient for functional cardiac regeneration and repair. Cell 154, 827-842.

Esposito, I., Kleeff, J., Bischoff, S. C., Fischer, L., Collecchi, P., Iorio, M., Bevilacqua. G., Bitchier, M. W., and Friess, H. (2002). The stem cell factor-c-kit system and mast cells in human pancreatic cancer. Lab. Invest. 82, 1481-1492.

Geissler, E. N., Ryan, M. A., and Housman D. E. (1988). The dominant-white spotting (W) locus of the mouse encodes the c-kit proto-oncogene. Cell 55, 185-192.

Gomez, D. L., O'Driscoll, M., Sheets, T. P., Hruban, R. H., Oberholzer, J., McGarrigle, J. J., and Shamblott, M. J. (2015). Neurogenin 3 expressing cells in the human exocrine pancreas have the capacity for endocrine cell fate. PLoS One 10, e0133862.

Goodell, M. A., Nguyen, H., and Shroyer, N. (2015). Somatic stem cell heterogeneity: diversity in the blood, skin and intestinal stem cell compartments. Nat. Rev. Mol. Cell. Biol. 16, 299-309.

Goss, G. M., Chaudhari, N., Hare, J. M., Nwojo, R., Seidler, B., Saur, D., and Goldstein, B. J. (2016). Differentiation potential of individual olfactory c-Kit+ progenitors determined via multicolor lineage tracing. Dev. Neurobiol. 76, 241-251.

Gradwohl, G., Dierich, A., LeMeur, M., and Guillemot, F. (2000). Neurogenin3 is required for the development of the four endocrine cell lineages of the pancreas. Proc. Natl. Acad. Sci. USA 97, 1607-1611.

Gu, G., Dubauskaite, J., and Melton, D. A. (2002). Direct evidence for the pancreatic lineage: NGN3+ cells are islet progenitors and are distinct from duct progenitors. Development 129, 2447-2457.

Hadi H. A., and Suwaidi J A. (2007). Endothelial dysfunction in diabetes mellitus. Vasc. Health Risk Manag. 3, 853-876.

Hatzistergos, K. E., Takeuchi, L. M., Saur, D., Seidler, B., Dymecki, S. M., Mai, J. J., White, I. A., Balkan, W., Kanashiro-Takeuchi, R. M., Schally, A. V. et al. (2015). cKit+ cardiac progenitors of neural crest origin. Proc. Natl. Acad. Sci. USA 112, 13051-13056.

Heger, K., Seidler, B., Vahl, J. C., Schwartz, C., Kober, M., Klein, S., Voehringer, D., Saur, D., and Schmidt-Supprian, M. (2014). CreER(T2) expression from within the c-Kit gene locus allows efficient inducible gene targeting in and ablation of mast cells. Eur. J. Immunol. 44, 296-306.

Hsu, Y. C., and Fuchs, E. (2012). A family business: stem cell progeny join the niche to regulate homeostasis. Nat. Rev. Mol. Cell. Biol. 13, 103-114.

Jennings, R. E., Berry, A. A., Strutt, J. P., Gerrard, D. T., and Hanley, N. A. (2015). Human pancreas development. Development 142, 126-317.

Jiang, F. X., and Morahan, G. (2012). Pancreatic stem cells: from possible to probable. Stem Cell Rev. 8, 647-657.

Keenan, H. A., Sun, J. K., Levine, J., Doria, A., Aiello, L. P., Eisenbarth, G., Bonner-Weir, S., and King, G. L. (2010). Residual insulin production and pancreatic β-cell turnover after 50 years of diabetes: Joslin Medalist. Diabetes 59, 2846-2853.

Klein, S., Seidler, B., Kettenberger, A., Sibaev, A., Rohn, M., Feil, R., Allescher, H. D., Vanderwinden, J. M., Hofmann, F., Schemann, M., et al. (2013). Interstitial cells of Cajal integrate excitatory and inhibitory neurotransmission with intestinal slow-wave activity. Nat. Commun. 4, 1630.

Kretzschmar, K., and Watt, F. M. (2012). Lineage tracing. Cell 148, 33-45.

Krishnamurthy, M., Ayazi, F., Li, J., Lyttle, A. W., Woods, M., Wu, Y., Yee, S. P., and Wang, R. (2007). c-Kit in early onset of diabetes: a morphological and functional analysis of pancreatic beta-cells in c-KitW-v mutant mice. Endocrinology 148, 5520-5530.

Lemper M, Leuckx G, Heremans Y, German M S, Heimberg H, Bouwens L, and Baeyens L. (2015). Reprogramming of human pancreatic exocrine cells to β-like cells. Cell Death Differ. 22, 1117-1130.

Leri, A., and Anversa, P. (2016). Complexity of tracking the fate of adult progenitor cells. Circ. Res. 119, 1067-1070

Leri, A., Rota, M., Pasqualini, F. S., Goichberg, P., and Anversa, P. (2015). Origin of cardiomyocytes in the adult heart. Circ. Res. 116, 150-166.

Liu, Q., Huang, X., Zhang, H., Tian, X., He, L., Yang, R., Yan, Y., Wang, Q. D., Gillich, A., and Zhou, B. (2015). c-kit(+) cells adopt vascular endothelial but not epithelial cell fates during lung maintenance and repair. Nat. Med. 21, 866-868.

Manoranjan, B., Wang, X., Hallett, R. M., Venugopal, C., Mack, S. C., McFarlane, N., Nolte, S. M., Scheinemann, K., Gunnarsson T, Hassell, J. A., et al. (2013). FoxG1 interacts with Bmi1 to regulate self-renewal and tumorigenicity of medulloblastoma stem cells. Stem Cells 31, 1266-1277.

Menge, B. A., Breuer, T. G., Ritter, P. R., Uhl, W., Schmidt, W. E., and Meier, J. J. (2012). Long-term recovery of β-cell function after partial pancreatectomy in humans. Metabolism 61, 20-24.

Mezza, T., and Kulkarni, R. N. (2014). The regulation of pre- and post-maturational plasticity of mammalian islet cell mass. Diabetologia 57, 1291-1303.

Murtaugh, L. C., and Melton, D. A. (2003). Genes, signals, and lineages in pancreas development. Annu. Rev. Cell Dev. Biol. 19, 71-89.

Muzumdar, M. D., Tasic, B., Miyamichi, K., Li, L., and Luo, L. (2007). A global double-fluorescent Cre reporter mouse. Genesis 45, 593-605.

Nadal-Ginard, B., Ellison, G. M., and Torella, D. (2014). The absence of evidence is not evidence of absence: the pitfalls of Cre knock-ins in the c-kit locus. Circ. Res. 115, 415-418.

Oram, R. A., Jones, A. G., Besser, R. E., Knight, B. A., Shields, B. M., Brown, R. J., Hattersley, A. T., and McDonald, T. J. (2014). The majority of patients with long-duration type 1 diabetes are insulin microsecretors and have functioning beta cells. Diabetologia 57, 187-191.

Orlic, D., Fischer, R., Nishikawa, S., Nienhuis, A. W., and Bodine, D. M. (1993). Purification and characterization of heterogeneous pluripotent hematopoietic stem cell populations expressing high levels of c-kit receptor. Blood 82, 762-770.

Perl, S., Kushner, J. A., Buchholz, B. A., Meeker, A. K., Stein, G. M., Hsieh, M., Kirby, M., Pechhold, S., Liu, E.

H., Harlan, D. M., et al. (2010). Significant human beta-cell turnover is limited to the first three decades of life as determined by in vivo thymidine analog incorporation and radiocarbon dating. J. Clin. Endocrinol. Metab. 95, E234-239.

Quesenberry, P. J., Colvin, G., and Abedi, M. (2005). Perspective: Fundamental and clinical concepts on stem cell homing and engraftment: A journey to niches and beyond. Exp. Hematol. 33, 9-19.

Qu, X., Afelik, S., Jensen, J. N., Bukys, M. A., Kobberup, S., Schmerr, M., Xiao, F., Nyeng, P., Veronica Albertoni, M., Grapin-Botton, A., et al. (2013). Notch-mediated post-translational control of Ngn3 protein stability regulates pancreatic patterning and cell fate commitment. Dev. Biol. 376, 1-12.

Rota, M., Kajstura, J., Hosoda, T., Bearzi, C., Vitale, S., Esposito, G., Iaffaldano, G., Padin-Iruegas, M. E., Gonzalez, A., Rizzi, R., et al. (2007). Bone marrow cells adopt the cardiomyogenic fate in vivo. Proc. Natl. Acad. Sci. USA 104, 17783-17788.

Saisho Y. (2014). Importance of beta cell function for the treatment of type 2 diabetes. J. Clin. Med. 3, 923-43.

Seymour, P. A. (2014). Sox9: a master regulator of the pancreatic program. Rev. Diabet. Stud. 11, 51-83.

Sherr, J. L., Ghazi, T., Wurtz, A., Rink, L., and Herold, K. C. (2014). Characterization of residual β cell function in long-standing type 1 diabetes. Diabetes Metab. Res. Rev. 30, 154-162.

Shih, H. P., Kopp, J. L., Sandhu, M., Dubois, C. L., Seymour, P. A., Grapin-Botton, A., and Sander, M. A. (2012). A Notch-dependent molecular circuitry initiates pancreatic endocrine and ductal cell differentiation. Development 139, 2488-2499.

Smukler, S. R., Arntfield, M. E., Razavi, R., Bikopoulos, G., Karpowicz, P., Seaberg, R., Dai, F., Lee, S., Ahrens, R., Fraser, P. E. et al. (2011). The adult mouse and human pancreas contain rare multipotent stem cells that express insulin. Cell Stem Cell 8, 281-293.

Soyer, J., Flasse, L., Raffelsberger, W., Beucher, A., Orvain, C, Peers B, Ravassard P, Vermot J, Voz M L, Mellitzer G., et al. (2010). Rfx6 is an Ngn3-dependent winged helix transcription factor required for pancreatic islet cell development. Development 137, 203-122.

van Berlo, J. H., Kanisicak, O., Maillet, M., Vagnozzi, R. J., Karch, J., Lin, S. C., Middleton, R. C., Marban, E., and Molkentin, J. D. (2014). c-kit+ cells minimally contribute cardiomyocytes to the heart. Nature 509, 337-341.

Wajchenberg B L. (2007). Beta-cell failure in diabetes and preservation by clinical treatment. Endocr. Rev. 28, 187-218.

Weinberg, N., Ouziel-Yahalom, L., Knoller, S., Efrat, S., and Dor, Y. (2007). Lineage tracing evidence for in vitro dedifferentiation but rare proliferation of mouse pancreatic beta-cells. Diabetes 56, 1299-1304.

Williams, S. E., Beronja, S., Pasolli, H. A., and Fuchs, E. (2011). Asymmetric cell divisions promote Notch-dependent epidermal differentiation. Nature 470, 353-358.

Xiao, X., Chen, Z., Shiota, C., Prasadan, K., Guo, P., El-Gohary, Y., Paredes, J., Welsh, C., Wiersch, J., and Gittes, G. K. (2013). No evidence for 13 cell neogenesis in murine adult pancreas. J. Clin. Invest. 123, 2207-2217.

Xu, X., D'Hoker, J., Stange, G., Bonne, S., De Leu, N., Xiao, X., Van de Casteele, M., Mellitzer, G., Ling, Z., Pipeleers, D., et al. (2008). Beta cells can be generated from endogenous progenitors in injured adult mouse pancreas. Cell 132, 197-207.

Yagihashi, S., Inaba, W., and Mizukami, H. (2016). Dynamic pathology of islet endocrine cells in type 2 diabetes: β-cell growth, death, regeneration and their clinical implications. J. Diabetes Investig. 7, 155-165.

Anversa, P., and Olivetti, G. (2002). Cellular Basis of Physiological and Pathological Myocardial Growth. In: Handbook of physiology. Section 2: The Cardiovascular System, The Heart, E Page, H. A. Fozzard, R. J. Solaro, eds. (New York Oxford University Press), pp. 75-144.

Beltrami, A. P., Barlucchi, L., Torella, D., Baker, M., Limana, F., Chimenti, S., Kasahara, H., Rota, M., Musso, E., Urbanek, K., et al. (2003). Adult cardiac stem cells are multipotent and support myocardial regeneration. Cell 114, 763-776.

Bearzi, C., Rota, M., Hosoda, T., Tillmanns, J., Nascimbene, A., De Angelis, A., Yasuzawa-Amano, S., Trofimova, I., Siggins, R. W., LeCapitaine, N., et al. (2007). Human cardiac stem cells. Proc. Natl. Acad. Sci. USA. 104, 14068-14073.

De Gasperi, R., Rocher, A. B., Sosa, M. A., Wearne, S. L., Perez, G. M., Friedrich, V. L. Jr., Hof, P. R., and Elder, G. A. (2008). The IRG mouse: a two-color fluorescent reporter for assessing Cre-mediated recombination and imaging complex cellular relationships in situ. Genesis 46, 308-317.

Dirice, E., Kahraman, S., Jiang, W., El Ouaamari, A., De Jesus, D. F., Teo, A. K., Hu, J., Kawamori, D., Gaglia, J. L., Mathis, D., et al. (2014). Soluble factors secreted by T cells promote β-cell proliferation. Diabetes 63, 188-202.

Feng, Z-C., Riopel, M., Popell, A., and Wang, R. (2015). A survival Kit for pancreatic beta cells: stem cell factor and c-Kit receptor tyrosine kinase. Diabetologia 58, 654-665.

Ferreira-Martins, J., Ogorek, B., Cappetta, D., Matsuda, A., Signore, S., D'Amario, D., Kostyla, J., Steadman, E., Ide-Iwata, N., Sanada, F., et al. (2012). Cardiomyogenesis in the developing heart is regulated by c-kit-positive cardiac stem cells. Circ. Res. 110, 701-715.

Geiss, G. K., Bumgarner, R. E., Birditt, B., Dahl, T., Dowidar, N., Dunaway, D. L., Fell, H. P., Ferree, S. George, R., Grogan, T., et al., (2008). Direct multiplexed measurement of gene expression with color-coded probe pairs. Nat. Biotech. 26, 317-325.

Gong, J., Zhang, G., Tian, F., and Wang, Y. (2012). Islet-derived stem cells from adult rats participate in the repair of islet damage. J. Mol. Histol. 43, 745-750.

Goss, G. M., Chaudhari, N., Hare, J. M., Nwojo, R., Seidler, B., Saur, D., and Goldstein, B. J. (2016). Differentiation potential of individual olfactory c-Kit+ progenitors determined via multicolor lineage tracing. Dev. Neurobiol. 76, 241-251.

Hatzistergos, K. E., Takeuchi, L. M., Saur, D., Seidler, B., Dymecki, S. M., Mai, J. J., White, I. A., Balkan, W., Kanashiro-Takeuchi, R. M., Schally, A. V. et al. (2015). cKit+ cardiac progenitors of neural crest origin. Proc. Natl. Acad. Sci. USA 112, 13051-13056.

Hosoda T, D'Amario D, Cabral-Da-Silva M C, Zheng H, Padin-Iruegas M E, Ogorek B, Ferreira-Martins J, Yasuzawa-Amano S, Amano K, Ide-Iwata N., et al. (2009). Clonality of mouse and human cardiomyogenesis in vivo. Proc. Natl. Acad. Sci. USA. 106, 17169-17174.

Liu, X., Hall, S. R., Wang, Z., Huang, H., Ghanta, S., Di Sante, M., Len, A., Anversa, P., and Perrella, M. A. (2015). Rescue of neonatal cardiac dysfunction in mice by administration of cardiac progenitor cells in utero. Nat Commun 6, 8825.

McDonald, J. H. (2014). Handbook of Biological Statistics (Sparky House Publishing, Baltimore, Md.).

Muzumdar, M. D., Tasic, B., Miyamichi, K., Li, L., and Luo, L. (2007). A global double-fluorescent Cre reporter mouse. Genesis 45, 593-605.

Peters, K., Panienka, R., Li, J., Kloppel G., and Wang, R. (2005). Expression of stem cell markers and transcription factors during the remodeling of the rat pancreas after duct ligation. Virchows Arch. 446, 56-63.

Sanada, F., Kim, J., Czarna, A., Chan, N. Y., Signore, S., Ogorek, B., Isobe, K., Wybieralska, E., Borghetti, G., Pesapane, A., et al. (2014). c-kit-positive cardiac stem cells nested in hypoxic niches are activated by stem cell factor reversing the aging myopathy. Circ. Res. 114, 41-55.

Talhouk, A., Kommoss, S., Mackenzie, R., Cheung, M., Leung, S., Chiu, D. S., Kalloger, S. E., Huntsman, D. G., Chen, S., Intermaggio, M., et al. (2016). Single-patient molecular testing with NanoString nCounter Data using a reference-based strategy for batch effect correction. PLoS ONE 11, e0153844.

Tiemann K., Panienka, R., and Kloppel G. (2007). Expression of transcription factors and precursor cell markers during regeneration of beta cells in pancreas of rats treated with streptozotocin. Virchows Arch. 450, 261-266.

van Berlo, J. H., Kanisicak, O., Maillet, M., Vagnozzi, R. J., Karch, J., Lin, S. C., Middleton, R. C., Marban, E., and Molkentin, J. D. (2014). c-kit+ cells minimally contribute cardiomyocytes to the heart. Nature 509, 337-341.

Veldman-Jones, M. H., Brant, R., Rooney, C., Geh, C., Emery, H., Harbron, C. G., Wappett, M., Sharpe, A., Dymond, M., Barrett, J. C., et al. (2015). Evaluating robustness and sensitivity of the NanoString Technologies nCounter Platform to enable multiplexed gene expression analysis of clinical samples. Cancer Res. 75, 2587-2593.

The invention claimed is:

1. A pharmaceutical composition comprising:
a therapeutically effective amount of isolated and in vitro expanded adult pancreatic stem cells and a pharmaceutically acceptable carrier for repairing and/or regenerating damaged tissue of a pancreas;
wherein said isolated and expanded pancreatic stem cells are c-kit positive, negative for hematopoietic cell lineage marker CD45, negative for mesenchymal stromal cell epitope CD90, clonogenic, multipotent, and self-renewing;
wherein said isolated and expanded adult pancreatic stem cells migrate to non-pathological and pathological portions of the pancreas, generate beta cells and produce insulin in vivo; and
wherein said pharmaceutical composition does not comprise a majority of cells that are both c-kit positive and tryptase-positive.

2. The pharmaceutical composition of claim 1, wherein the isolated pancreatic stem cells are capable of generating one or more pancreatic cell types selected from an exocrine cell, an endocrine cell, an alpha cell and a beta cell.

3. The pharmaceutical composition of claim 1, wherein the isolated pancreatic stem cells are cultured and expanded in vitro.

4. The pharmaceutical composition of claim 1, further comprising one or more cytokines and/or growth factors.

5. The pharmaceutical composition of claim 1, further comprising Stem Cell Factor (SCF), IGF-1, and/or HGF.

6. The pharmaceutical composition of claim 1, wherein the composition is formulated for catheter-mediated or direct injection.

7. The pharmaceutical composition of claim 1, wherein the composition comprises the isolated adult pancreatic stem cells in an encapsulating device.

8. The pharmaceutical composition of claim 1, wherein the insulin is human insulin.

9. The pharmaceutical composition of claim 1, wherein the in vitro expanded adult pancreatic stem cells are expanded in the presence of dexamethasone.

10. The pharmaceutical composition of claim 1, wherein the isolated and in vitro expanded adult pancreatic stem cells are negative for amylase.

11. The pharmaceutical composition of claim 1, wherein the isolated adult pancreatic stem cells are dissociated with a proteolytic and collagenolytic enzyme mixture without trypsin prior to passaging.

\* \* \* \* \*

```
                         SEQUENCE LISTING

<160> NUMBER OF SEQ ID NOS: 12

<210> SEQ ID NO 1
<211> LENGTH: 26
<212> TYPE: DNA
<213> ORGANISM: artificial
<220> FEATURE:
<223> OTHER INFORMATION: forward primer for amplification of c-kit

<400> SEQUENCE: 1
gcacctgctg aaatgtatga cataat                                            26

<210> SEQ ID NO 2
<211> LENGTH: 26
<212> TYPE: DNA
<213> ORGANISM: artificial
<220> FEATURE:
<223> OTHER INFORMATION: reverse primer for amplification of c-kit

<400> SEQUENCE: 2
ctgcagtttg ctaagttgga gtaaat                                            26

<210> SEQ ID NO 3
<211> LENGTH: 15
<212> TYPE: DNA
<213> ORGANISM: artificial
<220> FEATURE:
<223> OTHER INFORMATION: forward primer for amplification of Pdx1

<400> SEQUENCE: 3
cagtgggcag gcggc                                                        15

<210> SEQ ID NO 4
<211> LENGTH: 21
<212> TYPE: DNA
<213> ORGANISM: artificial
<220> FEATURE:
<223> OTHER INFORMATION: reverse primer for amplification of Pdx1

<400> SEQUENCE: 4
cggccgtgag atgtacttgt t                                                 21

<210> SEQ ID NO 5
<211> LENGTH: 21
<212> TYPE: DNA
<213> ORGANISM: artificial
<220> FEATURE:
```

<223> OTHER INFORMATION: forward primer for amplification of Sox9

<400> SEQUENCE: 5
gctctggaga cttctgaacg a                                        21

<210> SEQ ID NO 6
<211> LENGTH: 17
<212> TYPE: DNA
<213> ORGANISM: artificial
<220> FEATURE:
<223> OTHER INFORMATION: reverse primer for amplification of Sox9

<400> SEQUENCE: 6
tggcctcctc tgcctcc                                             17

<210> SEQ ID NO 7
<211> LENGTH: 20
<212> TYPE: DNA
<213> ORGANISM: artificial
<220> FEATURE:
<223> OTHER INFORMATION: forward primer for amplification of Ngn3

<400> SEQUENCE: 7
ttttctcctt tggggctggg                                          20

<210> SEQ ID NO 8
<211> LENGTH: 20
<212> TYPE: DNA
<213> ORGANISM: artificial
<220> FEATURE:
<223> OTHER INFORMATION: reverse primer for amplification of Ngn3

<400> SEQUENCE: 8
aggcgtcatc ctttctaccg                                          20

<210> SEQ ID NO 9
<211> LENGTH: 20
<212> TYPE: DNA
<213> ORGANISM: artificial
<220> FEATURE:
<223> OTHER INFORMATION: forward primer for amplification of Nkx6.1

<400> SEQUENCE: 9
agggctcgtt tggcctattc                                          20

<210> SEQ ID NO 10
<211> LENGTH: 20
<212> TYPE: DNA
<213> ORGANISM: artificial
<220> FEATURE:
<223> OTHER INFORMATION: reverse primer for amplification of Nkx6.1

<400> SEQUENCE: 10
cgtcgtcctc ttcctcgttc                                          20

<210> SEQ ID NO 11
<211> LENGTH: 25
<212> TYPE: DNA
<213> ORGANISM: artificial
<220> FEATURE:
<223> OTHER INFORMATION: forward primer for amplification of B2M

<400> SEQUENCE: 11
caaggactgg tctttctatc tcttg                                    25

```
<210> SEQ ID NO 12
<211> LENGTH: 20
<212> TYPE: DNA
<213> ORGANISM: artificial
<220> FEATURE:
<223> OTHER INFORMATION: reverse primer for amplification of B2M

<400> SEQUENCE: 12
attcatccaa tccaaatgcg                                                  20
```